(12) United States Patent
Vervoordeldonk et al.

(10) Patent No.: US 11,738,196 B2
(45) Date of Patent: *Aug. 29, 2023

(54) TREATMENT OF DISORDERS ASSOCIATED WITH INFLAMMATION

(71) Applicant: Galvani Bioelectronics Limited, Middlesex (GB)

(72) Inventors: Margarita J. Vervoordeldonk, Maarssen (NL); Eric Irwin, Collegeville, PA (US); Daniel John Chew, Middlesex (GB); Matteo Donega, Middlesex (GB); Cindy Cleypool, Middlesex (GB); Isha Gupta, Middlesex (GB)

(73) Assignee: Galvani Bioelectronics Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,432

(22) Filed: Jul. 25, 2022

(65) Prior Publication Data
US 2022/0409895 A1 Dec. 29, 2022

Related U.S. Application Data

(63) Continuation of application No. 16/955,393, filed as application No. PCT/GB2018/053731 on Dec. 20, 2018, now Pat. No. 11,446,496.
(Continued)

(51) Int. Cl.
*A61N 1/00* (2006.01)
*A61N 1/36* (2006.01)
(Continued)

(52) U.S. Cl.
CPC ......... *A61N 1/3606* (2013.01); *A61N 1/0556* (2013.01); *A61N 1/3614* (2017.08);
(Continued)

(58) Field of Classification Search
None
See application file for complete search history.

(56) References Cited

U.S. PATENT DOCUMENTS 6,442,431 B1 * 8/2002 Veraart ............... A61N 1/0543
607/54
8,831,739 B2 * 9/2014 McCreery ............. A61N 1/05
607/116
(Continued)

FOREIGN PATENT DOCUMENTS

EP   1 897 586 A1   3/2008
WO   2012 083259 A2   6/2012
(Continued)

OTHER PUBLICATIONS

Cogan et al., Tissue damage threshold during therapeutic electrical stimulation, J Neural Eng. Apr. 2016; 13(2): 021001. Doi: 10.1088/1741-2560/13/2/021001 (Year: 2016).*
(Continued)

*Primary Examiner* — Erica S Lee
(74) *Attorney, Agent, or Firm* — Banner & Witcoff, Ltd.

(57) ABSTRACT

Stimulation of neural activity in a nerve supplying the spleen, wherein the nerve is adjacent to the splenic artery at a position where the splenic artery is not in direct contact with the pancreas, can modulate pro- and anti-inflammatory molecules levels, thereby reducing inflammation and providing ways of treating disorders, such as disorders associated with inflammation. The invention provides improved ways of reducing inflammation with minimized off-target effects, in particular surgical trauma.

16 Claims, 49 Drawing Sheets

Related U.S. Application Data

(60) Provisional application No. 62/608,412, filed on Dec. 20, 2017.

(51) Int. Cl.
*A61N 1/05* (2006.01)
*A61N 1/08* (2006.01)

(52) U.S. Cl.
CPC ..... *A61N 1/36135* (2013.01); *A61N 1/36139* (2013.01); *A61N 1/36171* (2013.01); *A61N 1/36178* (2013.01); *A61N 2001/083* (2013.01)

(56) References Cited

U.S. PATENT DOCUMENTS

| | | | |
|---|---|---|---|
| 10,363,420 B2* | 7/2019 | Fried | A61B 5/4836 |
| 2004/0236382 A1 | 11/2004 | Dinsmoor et al. | |
| 2005/0075701 A1* | 4/2005 | Shafer | A61N 1/36017 607/72 |
| 2005/0075702 A1 | 4/2005 | Shafer | |
| 2006/0217707 A1* | 9/2006 | Daniel | A61B 18/1477 606/50 |
| 2009/0054955 A1* | 2/2009 | Kopell | A61N 5/0622 607/88 |
| 2009/0118780 A1* | 5/2009 | DiLorenzo | A61N 1/36007 607/2 |
| 2010/0125304 A1 | 5/2010 | Faltys | |
| 2011/0106208 A1 | 5/2011 | Faltys et al. | |
| 2011/0190849 A1 | 8/2011 | Faltys et al. | |
| 2011/0313488 A1 | 12/2011 | Hincapie Ordonez et al. | |
| 2013/0085537 A1 | 4/2013 | Mashiach | |
| 2014/0288551 A1 | 9/2014 | Bharmi et al. | |
| 2015/0174397 A1 | 6/2015 | Bhadra et al. | |
| 2015/0258341 A1* | 9/2015 | Ternes | A61N 1/36142 607/59 |
| 2016/0015978 A1* | 1/2016 | Cakmak | A61N 1/36031 607/62 |
| 2016/0015988 A1 | 1/2016 | Perryman et al. | |
| 2016/0067497 A1 | 3/2016 | Levine et al. | |
| 2017/0095679 A1 | 4/2017 | Sobotka et al. | |
| 2017/0113046 A1 | 4/2017 | Fried et al. | |
| 2017/0165480 A1* | 6/2017 | O'Mahony | A61M 16/024 |
| 2018/0161577 A1 | 6/2018 | Goedeke et al. | |
| 2019/0290913 A1 | 9/2019 | Blancou et al. | |

FOREIGN PATENT DOCUMENTS

| | | |
|---|---|---|
| WO | 2013086461 A1 | 6/2013 |
| WO | 2014 153223 A1 | 9/2014 |
| WO | 2014 197625 A1 | 12/2014 |
| WO | 2016 170510 A1 | 10/2016 |

OTHER PUBLICATIONS

Douglas B. McCreery et al., "Charge Density and Charge Per Phase as Cofactors in Neural Injury Induced by Electrical Stimulation," in IEEE Transactions on Biomedical Engineering, vol. 37, No. 10, pp. 996-1001, Oct. 1990, DOI: 10.1109/10.102812.

Modin A. et al., "Repeated Renal and Splenic Sympathetic Nerve Stimulation in Anaesthetized Pigs: Maintained Overflow of Neuropeptide Y in Controls but not After Reserpine," Journal of the Autonomic Nervous Systems, Elsevier, Amsterdamn, NL, vol. 49, No. 2, Oct. 1, 1994, pp. 123-134, XP024325768, ISSN: 0165-1838, DOI: 10.1016/0165-1838(94)90132-5.

Modin A. et al., "Comparison of the Acute Influence of Neuropeptide Y and Sympathetic Stimulation on the Composition of Blood Cells in the Splenic Vein in Vivo," Regulatory Peptides, Elsevier Science Bv, NL, vol. 47, No. 2, Sep. 3, 1993, pp. 159-169, XP025209233, ISSN: 0167-0115, DOI: 10.1016/0167-0115(93)90420-D.

William M Reichert, "Indwelling Neural Implants: Strategies for Contending with the In Vivo Environment," Frontiers in Neuroengineering, Boca Raton (FL): CRC Press/Taylor & Francis <http://www.crcpress.com/>; 2008, ISBN-13: 978-0-8493-9362-4.

"Important Safety Instructions" for the St. Jude Medical Infinity™ DBS System—<https://www.neuromodulation.abbott/us/en/products/dbs-therapy-movement-disorders/st-jude-medical-infinity-dbs-system.html#isi <https://www.neuromodulation.abbott/us/en/products/dbs-therapymovement-disorders/st-jude-medical-infinity-dbs-system.html>, accessed Jan. 27, 2022.

Stuart F. Cogan et al., "Tissue damage thresholds during therapeutic electrical stimulation," Journal of Neural Engineering, Apr. 2016 ; 13(2): 021001. doi:10.1088/1741-2560/13/2/021001.

* cited by examiner

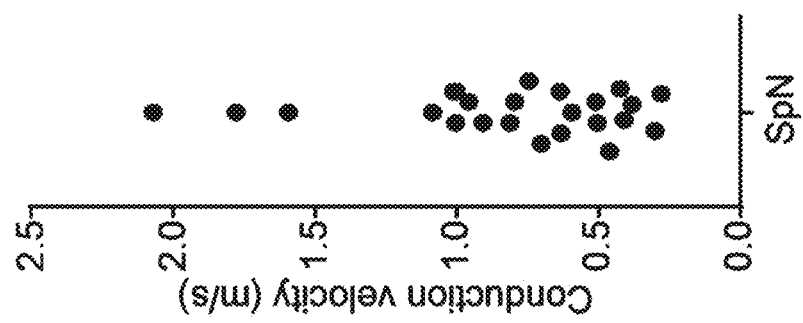
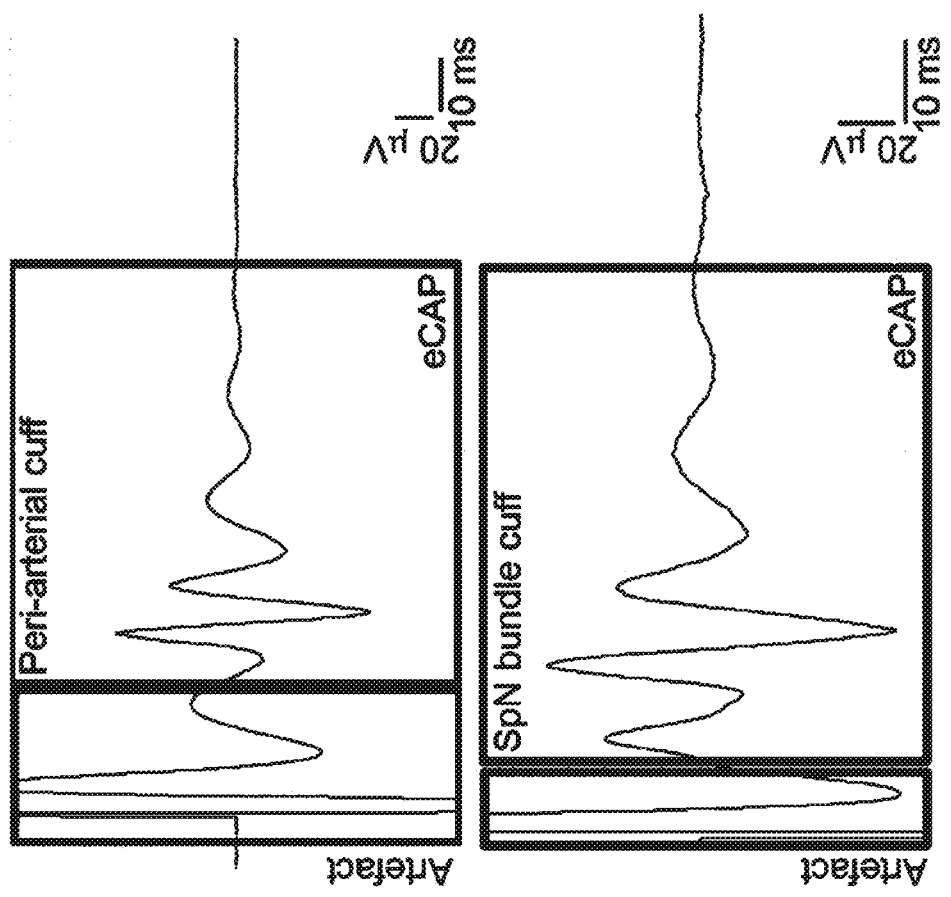

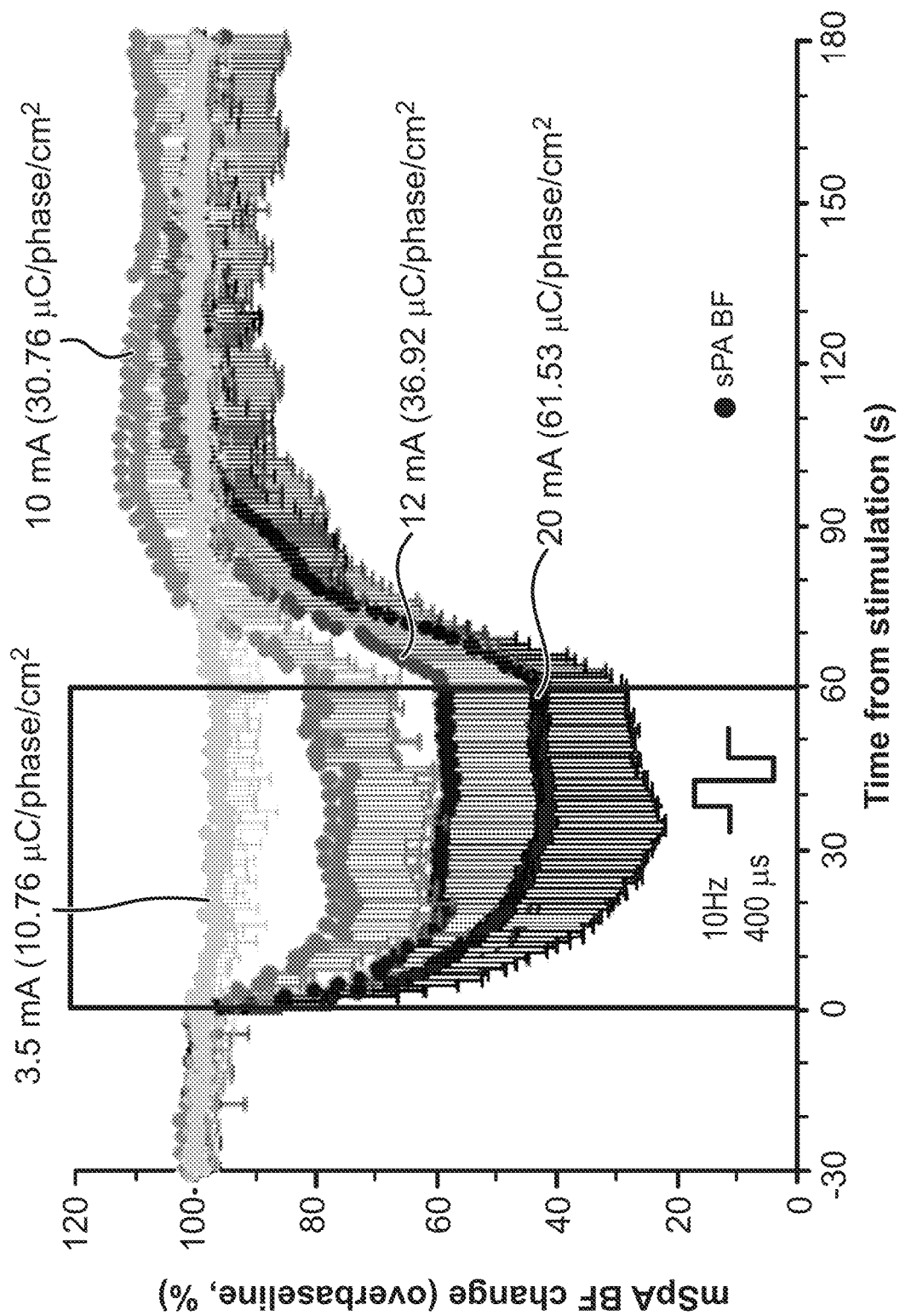

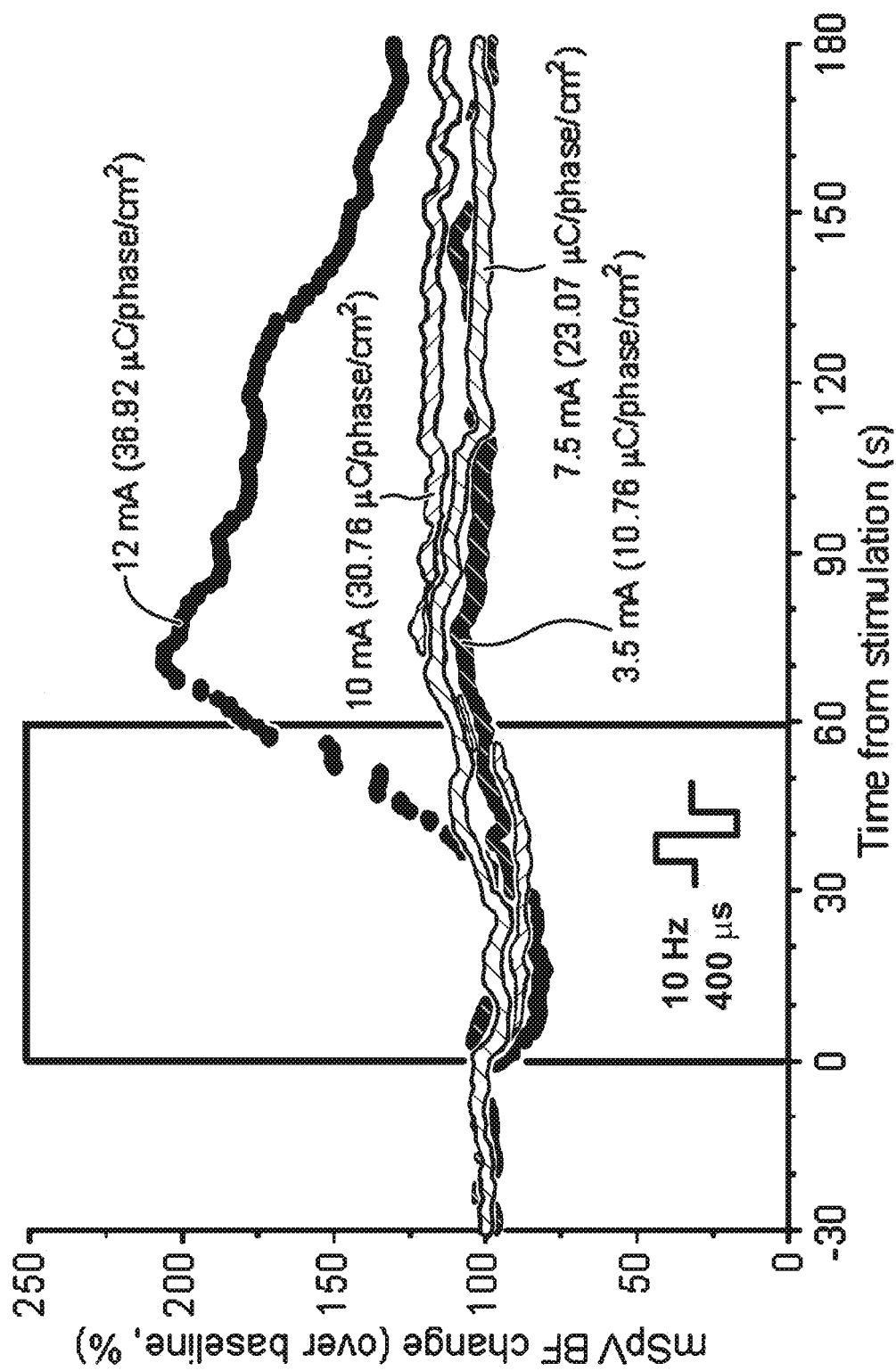

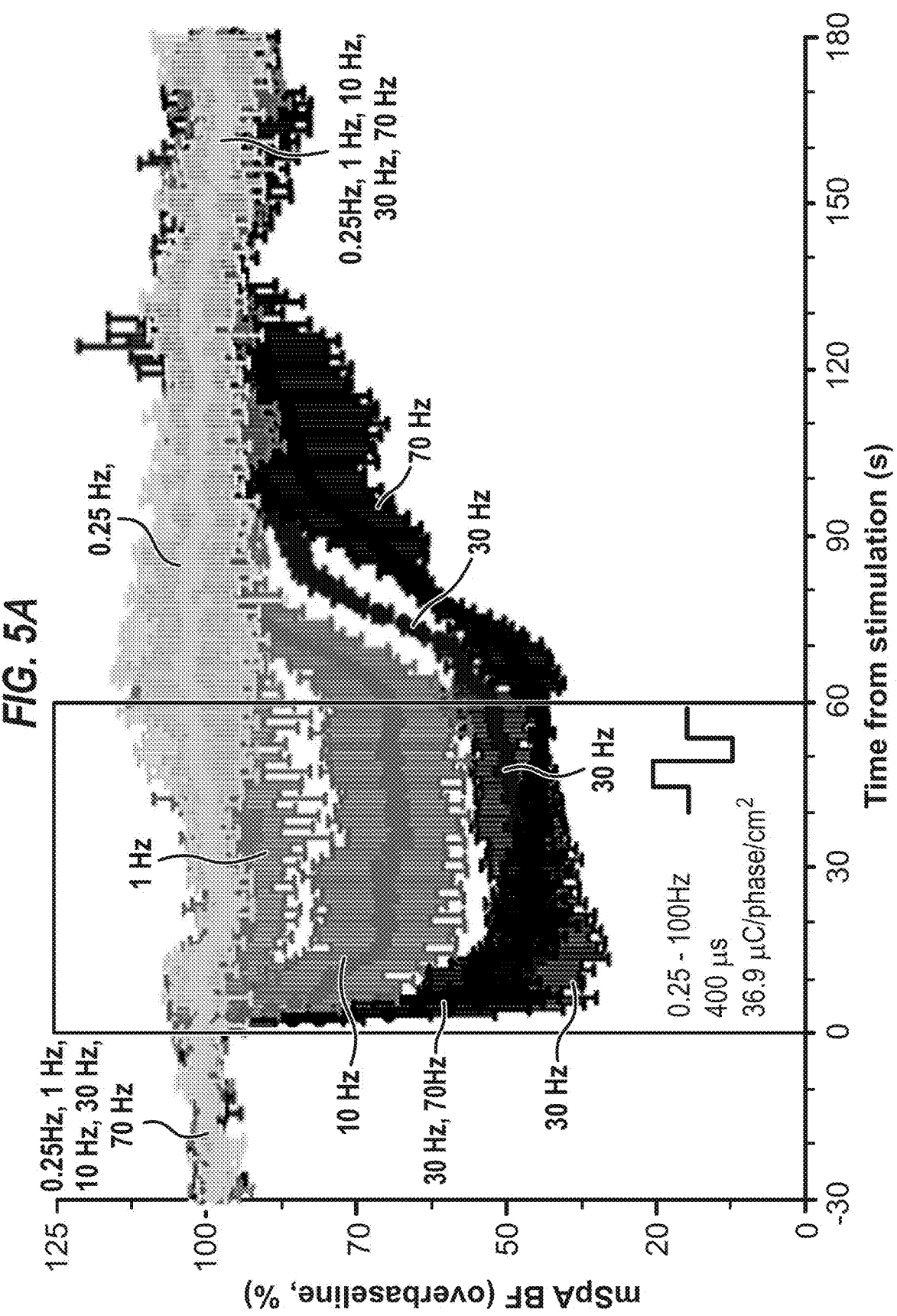

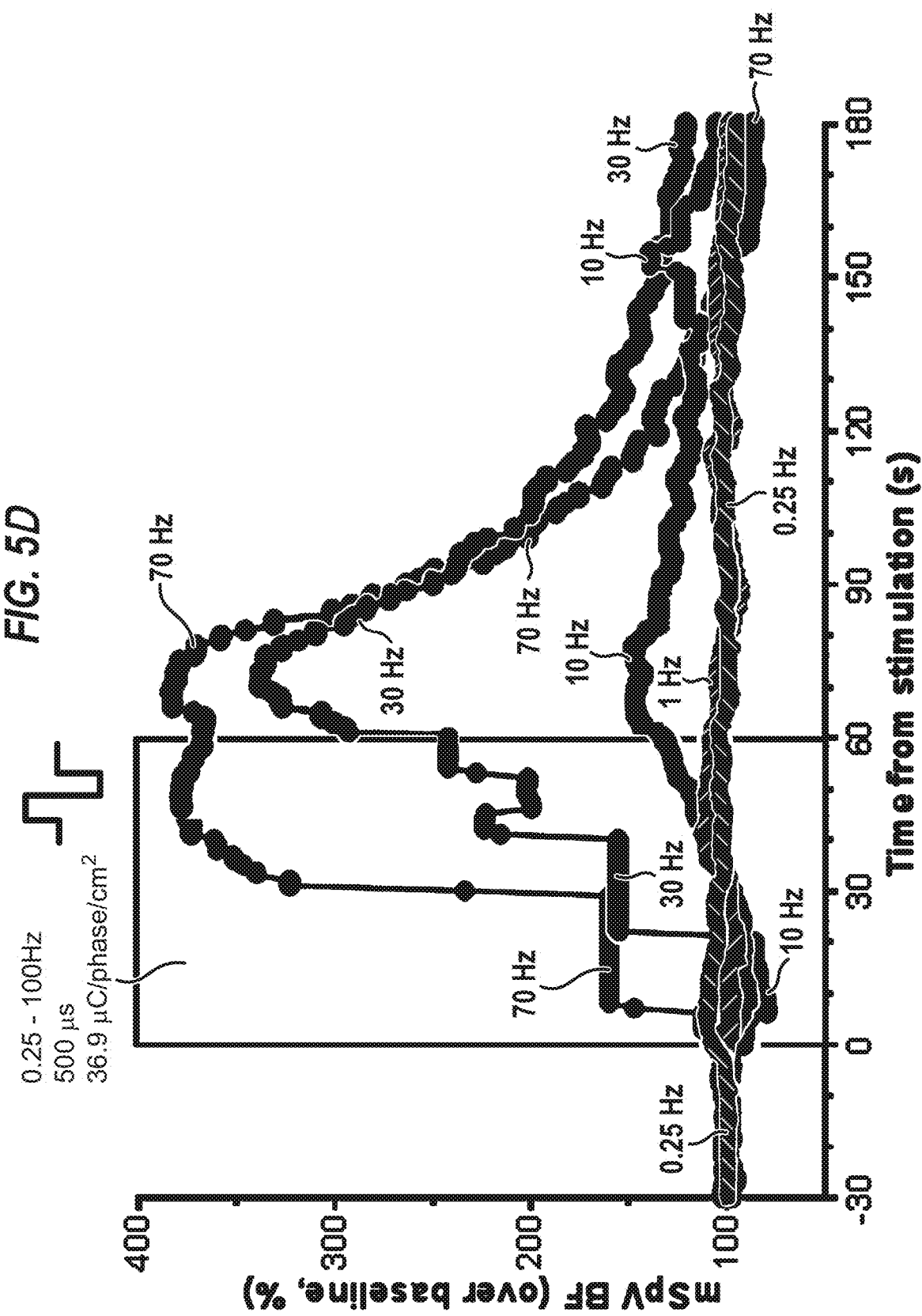

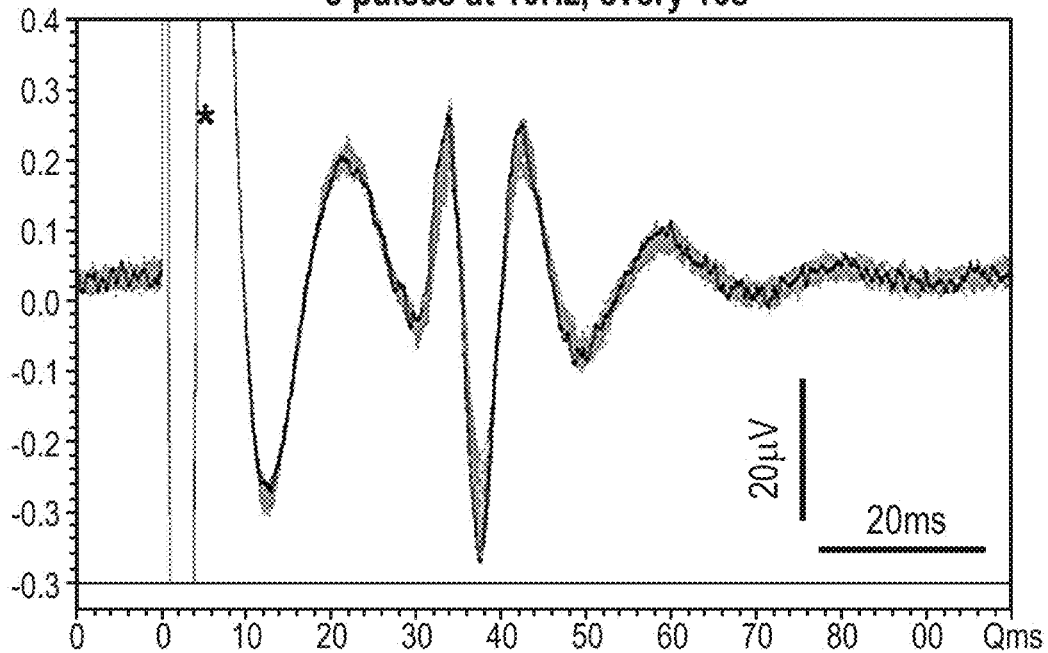
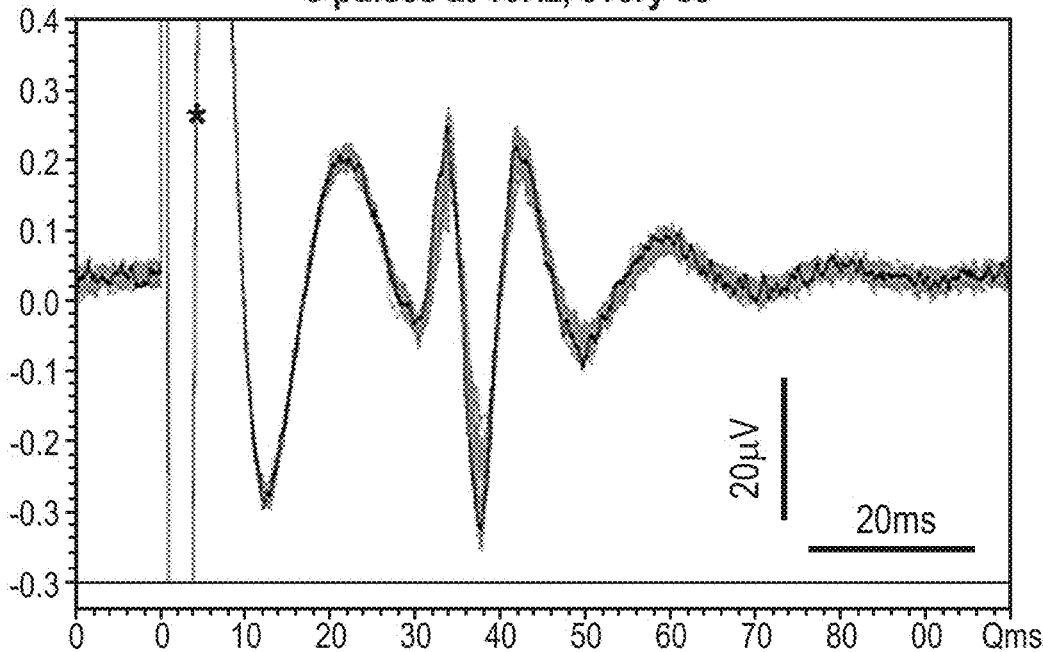

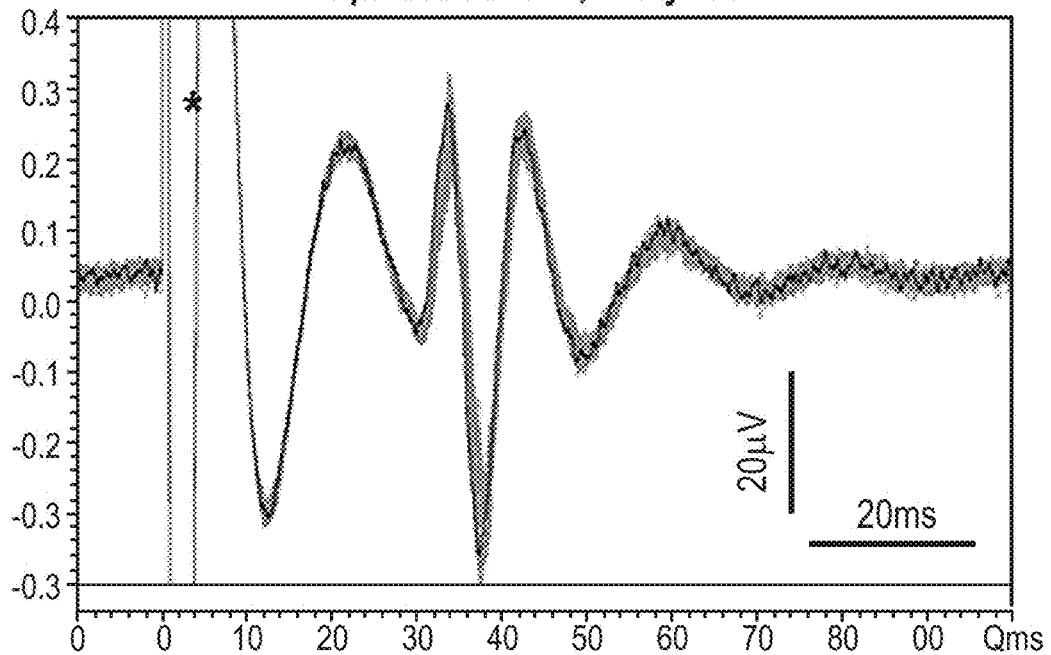

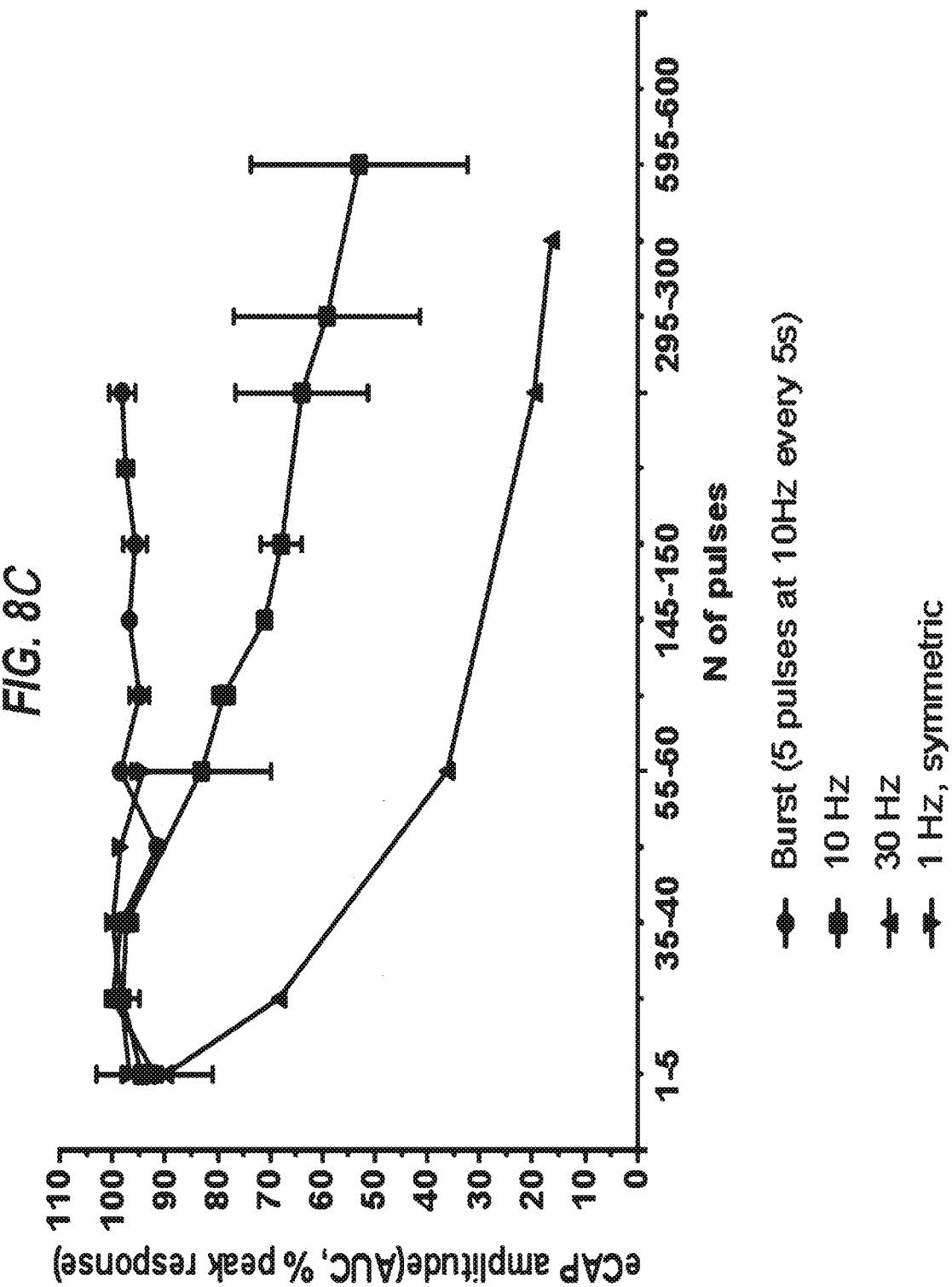

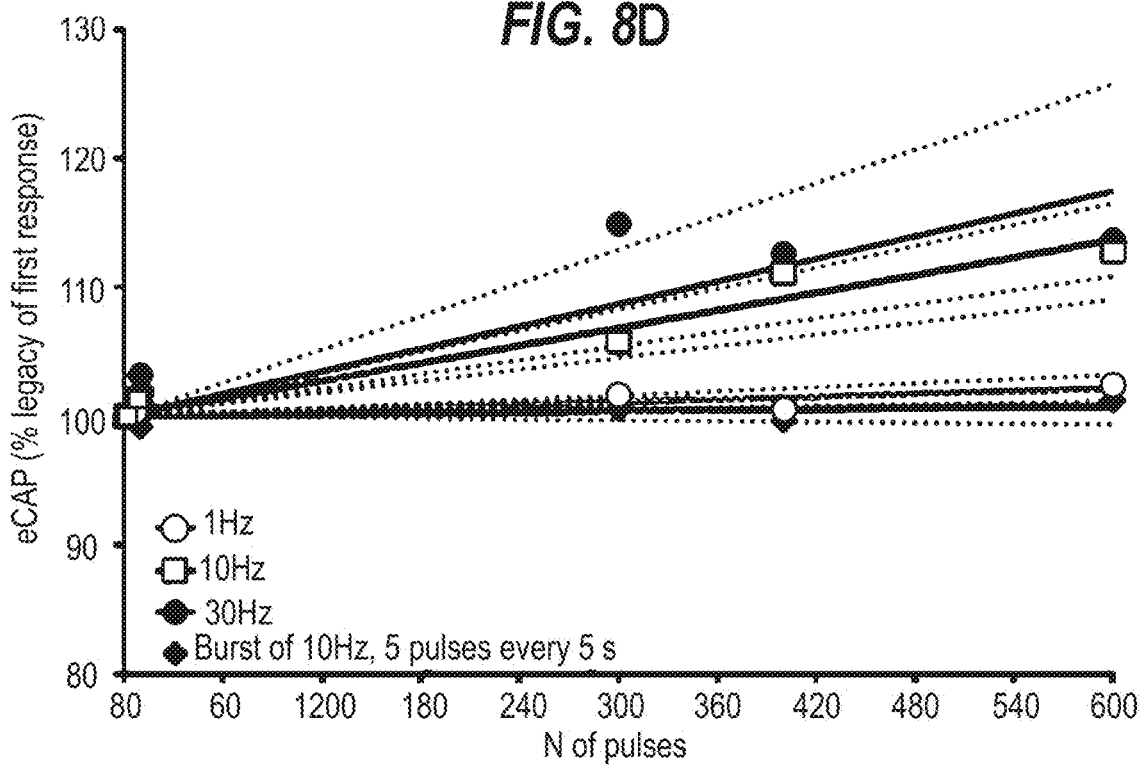
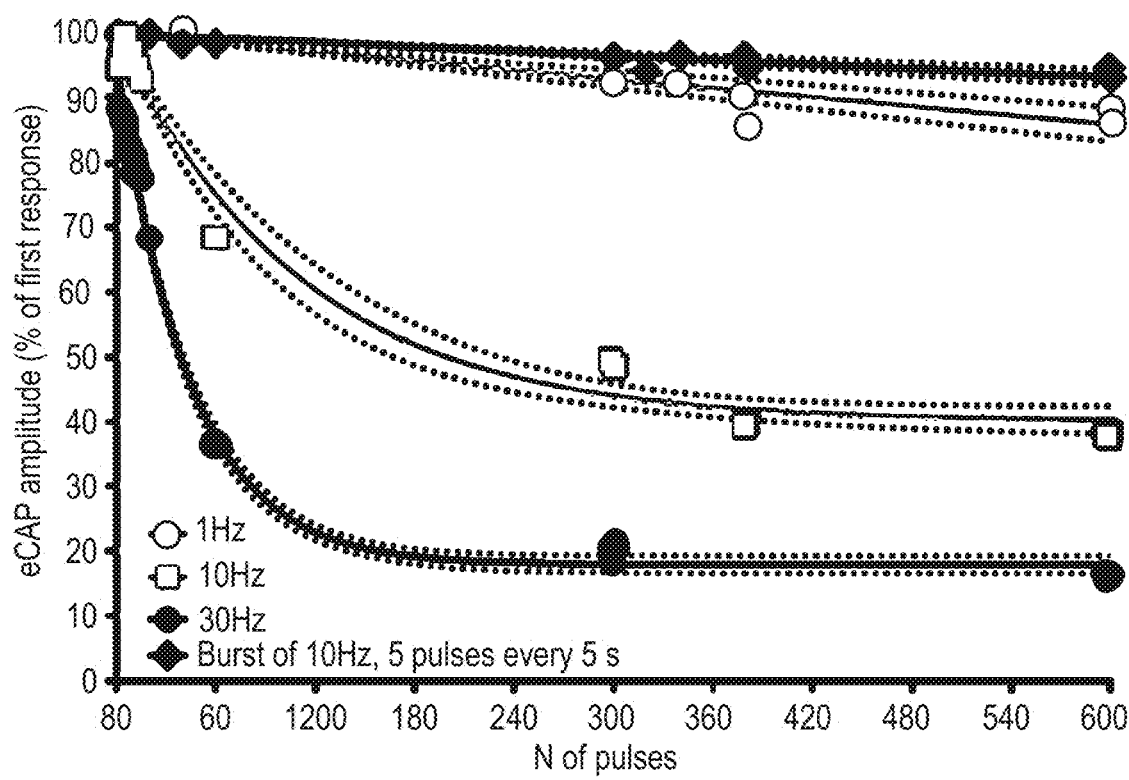

Cadaver III

Cadaver III

Cadaver III

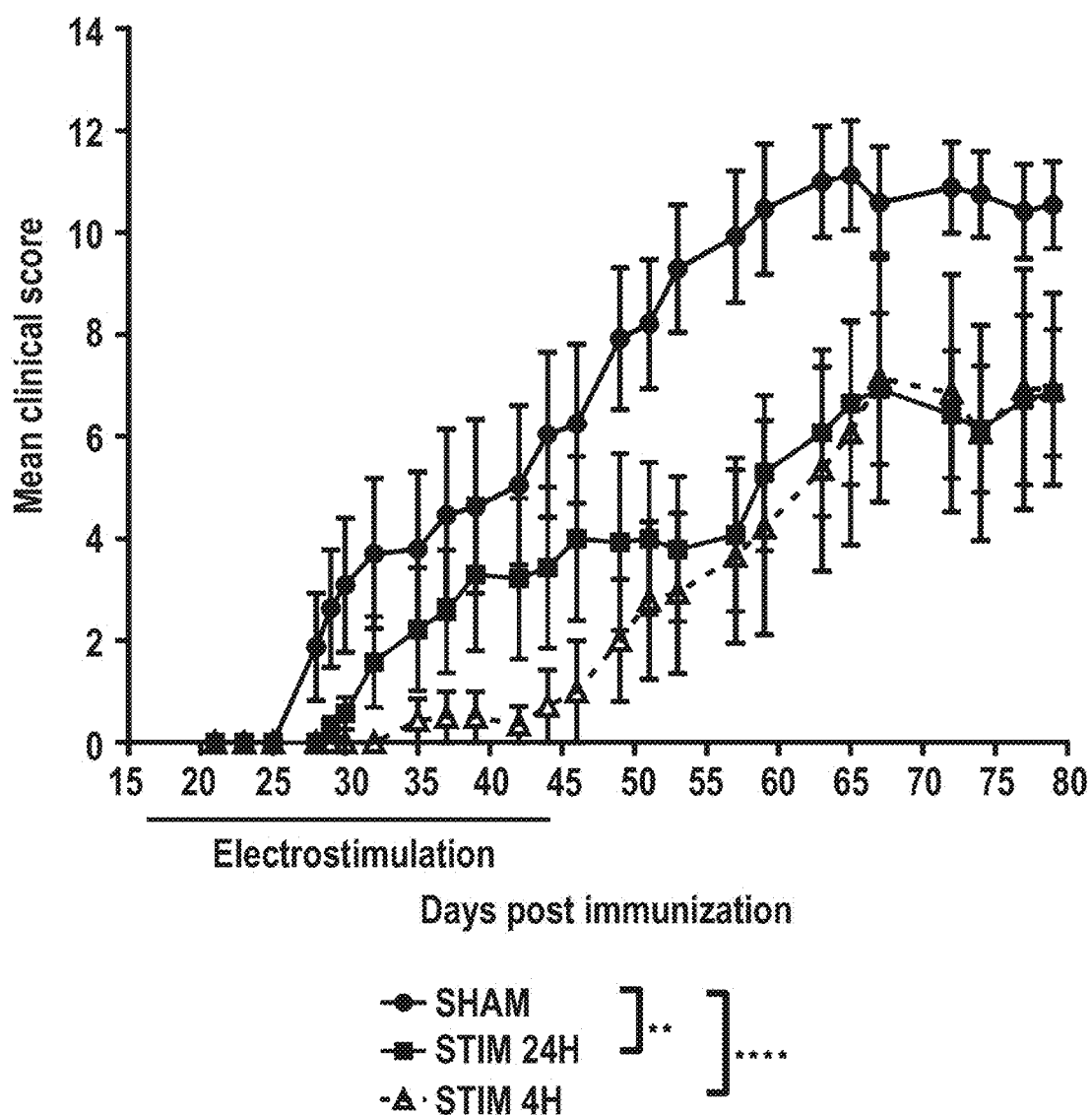

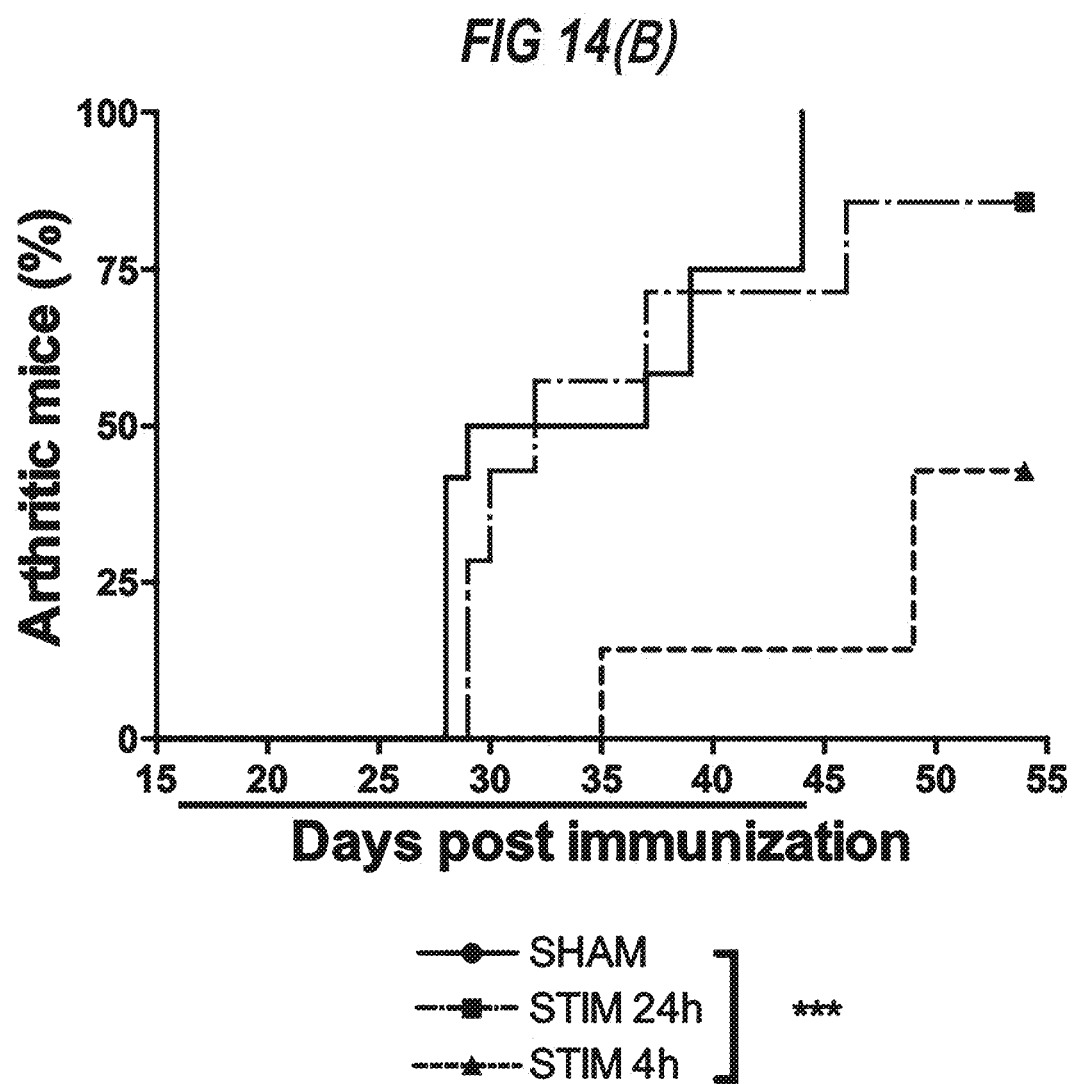

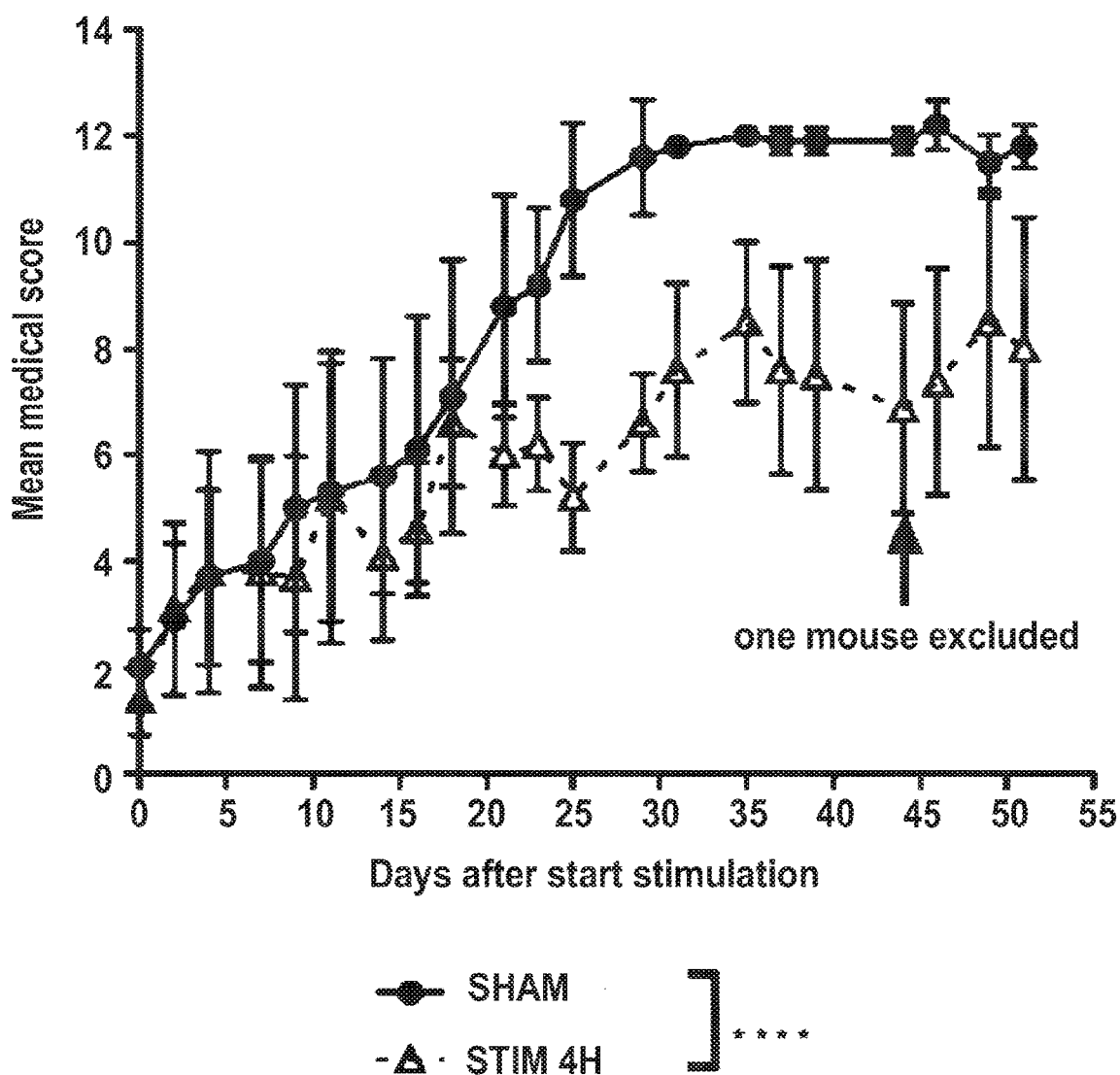

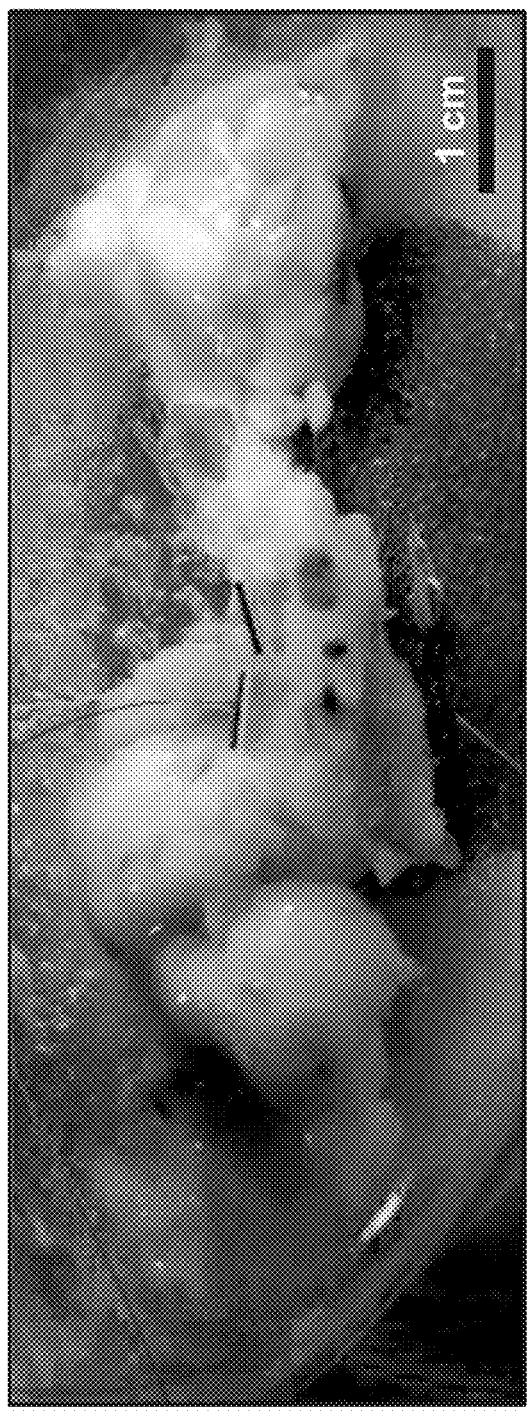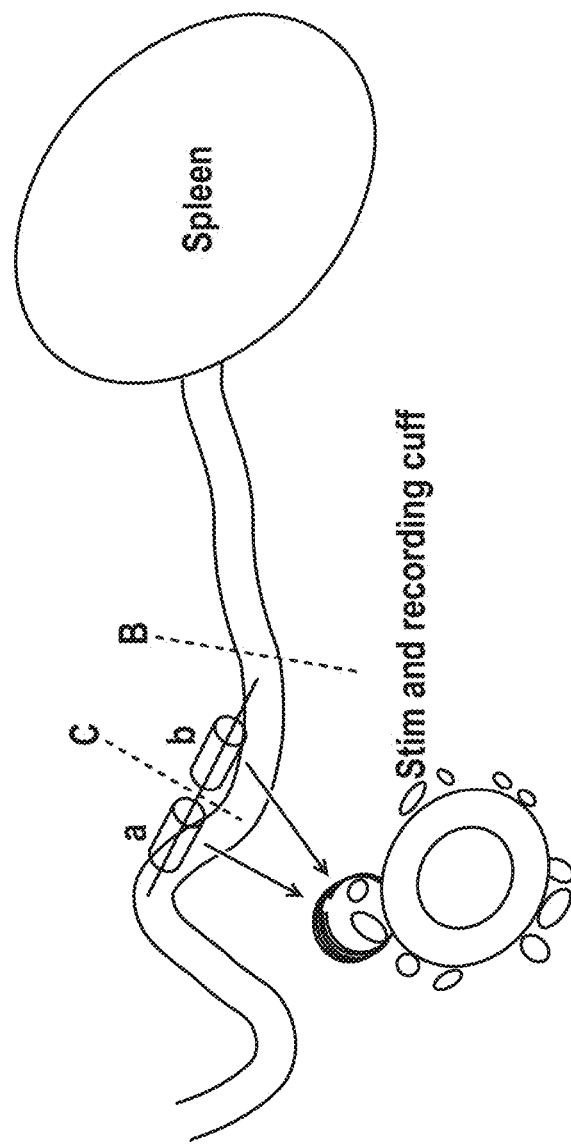
FIG. 16A

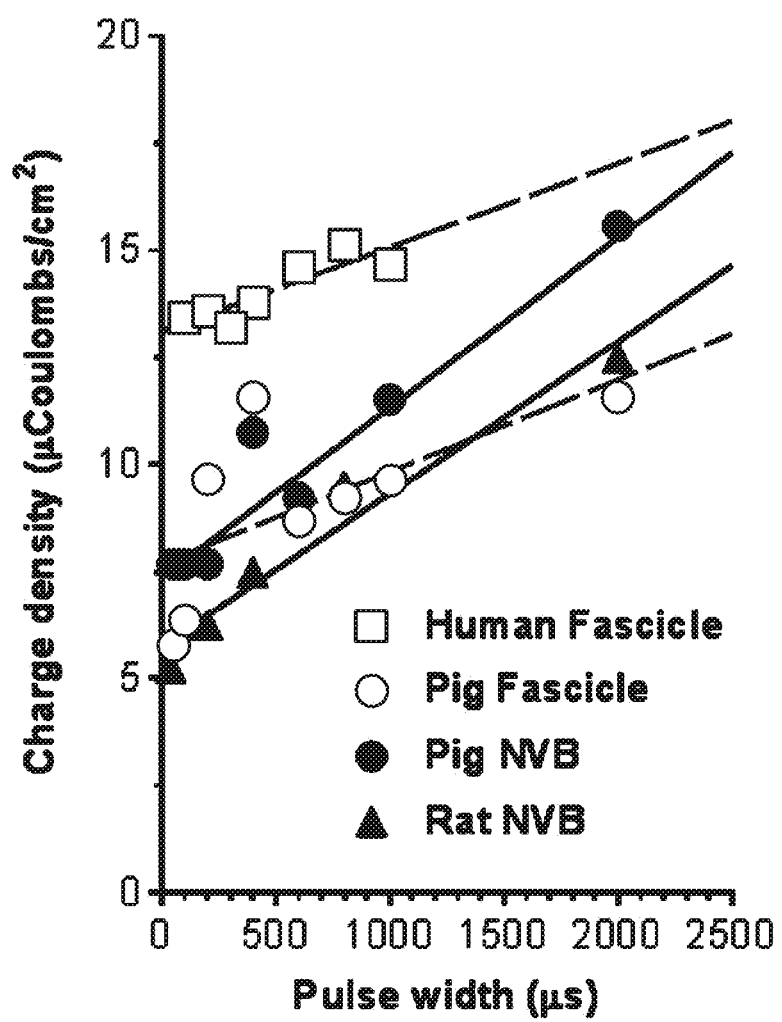

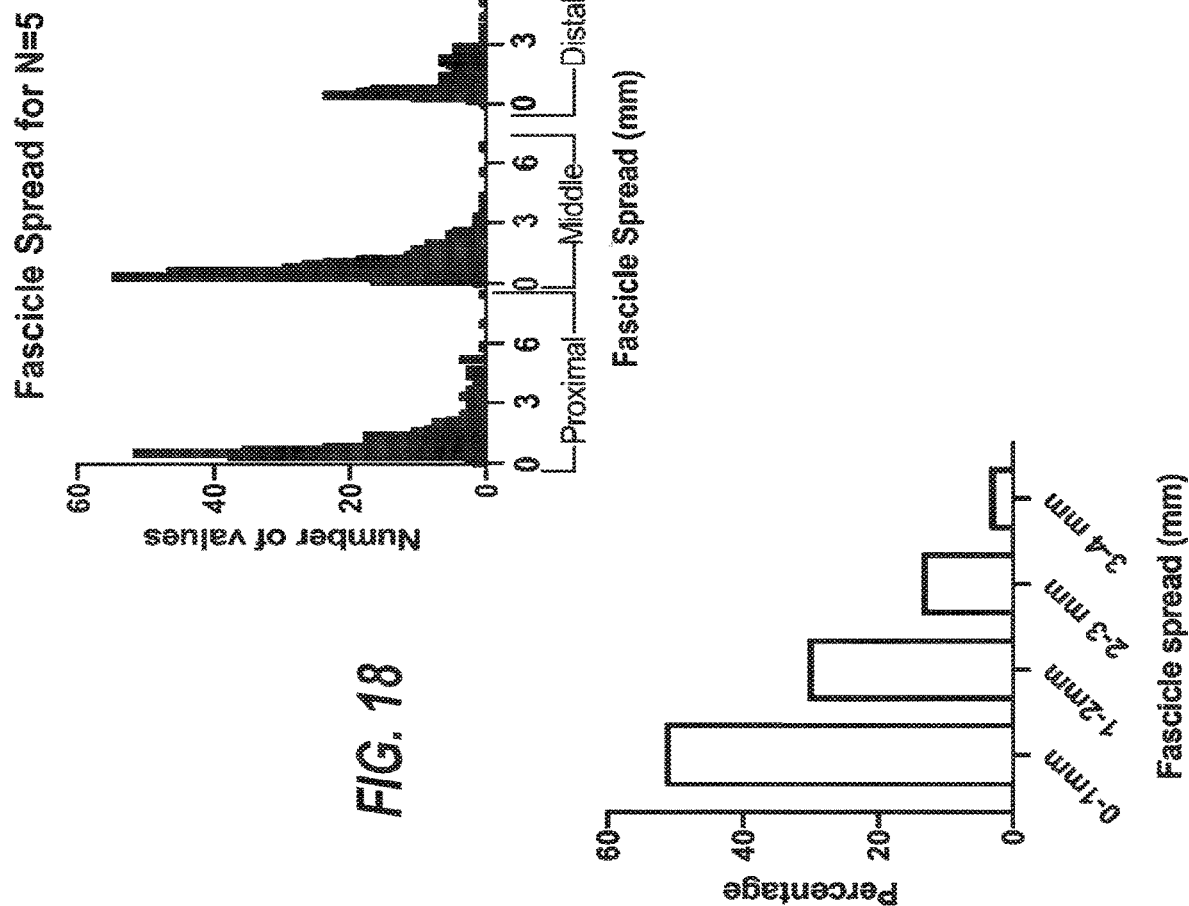
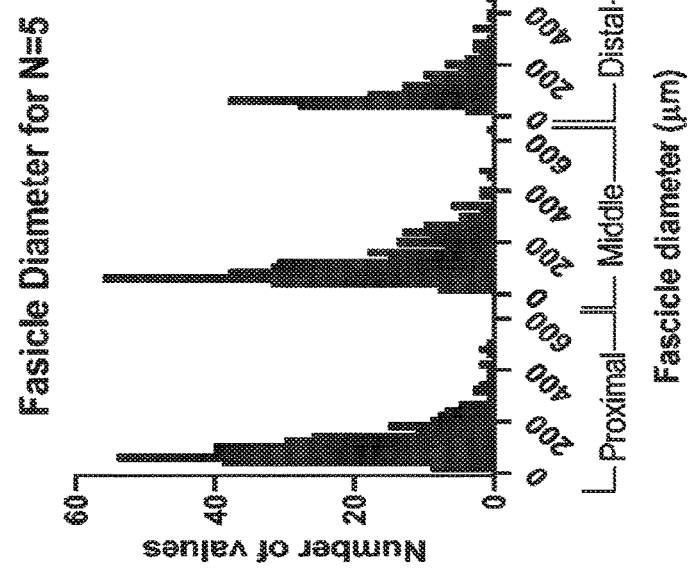
FIG. 18

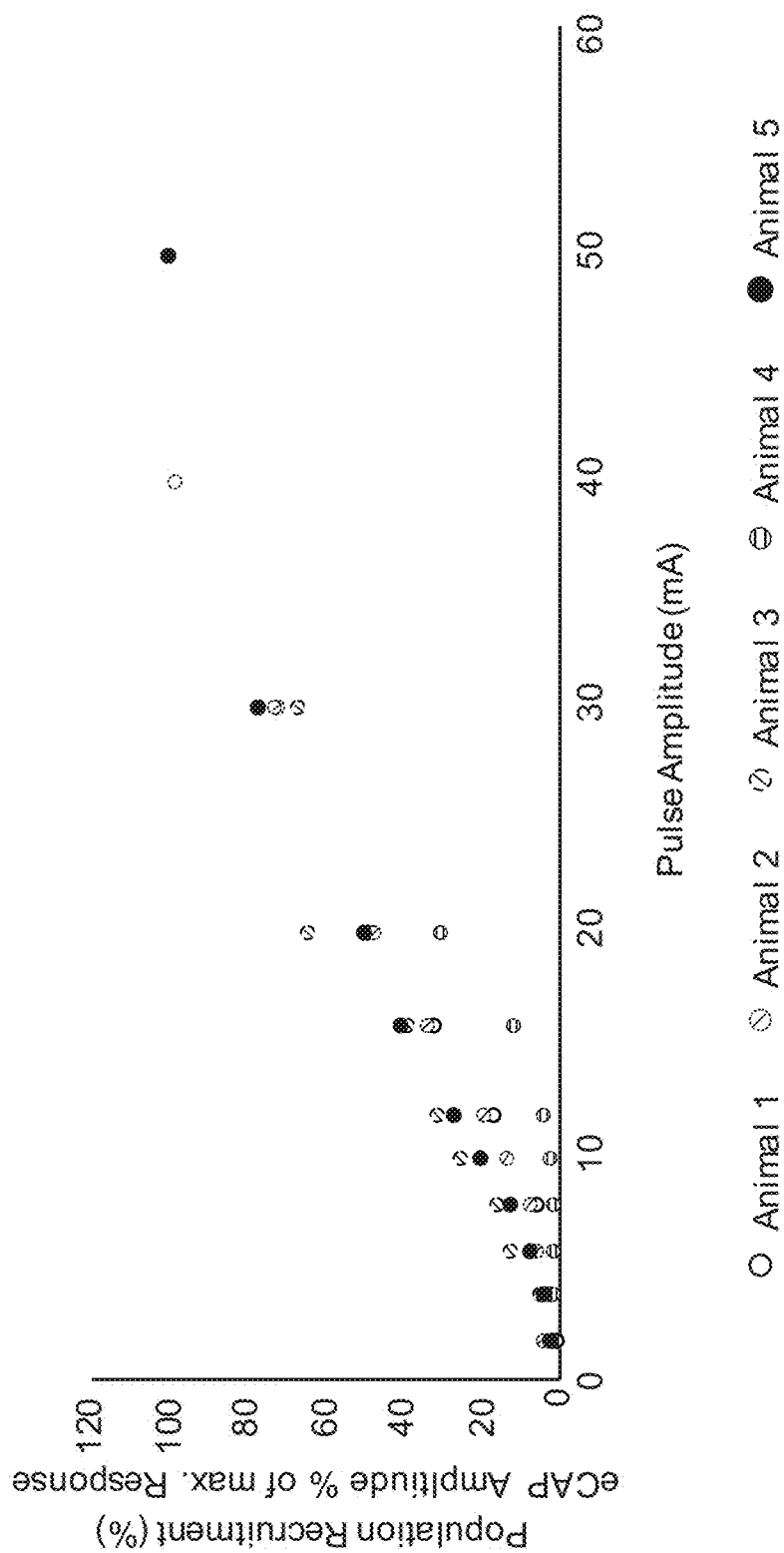

Acute Stimulation on splenic neurovascular bundle
Strength – duration curve

*in-silico* data from porcine models

*in-silico* data from porcine models

*in-silico* data from human models

*in-silico* data from human models

TREATMENT OF DISORDERS ASSOCIATED WITH INFLAMMATION

CROSS-REFERENCE TO RELATED APPLICATION

This application is a continuation of U.S. patent application Ser. No. 16/955,393 filed Jun. 18, 2018, which is a U.S. National Stage application under 35 U.S.C. § 371 of International Application PCT/GB2018/053731 (published as WO 2019/122908) filed Dec. 20, 2018 which claims the benefit of priority to U.S. provisional Application No. 62/608,412 filed Dec. 20, 2017. Each of these prior applications are hereby incorporated by reference in their entirety.

TECHNICAL FIELD

The invention relates to neuromodulation of a nerve adjacent to the splenic artery, more particularly to devices, systems and methods that stimulate neural activity in the nerve, and even more particularly to signal parameters and electrode design. The invention also relates to devices, systems and methods that stimulate neural activity in the nerve for treating disorders associated with inflammation.

BACKGROUND ART

Inflammation plays a fundamental role in host defenses and the progression of immune-mediated diseases (reviewed in [1]). The inflammatory response is initiated in response to an injury and/or an infection by chemical mediators (e.g. cytokines and prostaglandins) and inflammatory cells (e.g. leukocytes). A controlled inflammatory response is beneficial, for example, in the elimination of harmful agents and the initiation of the repair of damaged tissue providing protection against infection.

However, the inflammatory response can become detrimental if dysregulated, leading to a variety of inflammatory disorders such as rheumatoid arthritis, osteoarthritis, asthma, allergies, septic shock syndrome, atherosclerosis, and inflammatory bowel disease, Crohn's disease, ulcerative colitis, and other clinical conditions mediated by chronic inflammation.

The spleen contains half of the body's monocyte population making this organ the main contributor in inflammation, in particular in response to endotoxemic shock [2]. This organ is known to be innervated by different nervous branches (reviewed in [3]). The parasympathetic innervation of the spleen is a matter of debate since Dale's isolation of acetylcholine (ACh) from the spleen [3]. Buij and co-workers have suggested a parasympathetic innervation of the spleen in rodents [4,5], but human correlation to this nerve is not known. The traditional view of splenic innervation is proposed to be 98% sympathetic as demonstrated by neuroanatomical and neurochemical evidences [3].

From a functional point of view, vagus nerve stimulation (reviewed in [6]) as well as the nerve plexus surrounding the splenic artery, referred to herein as the splenic arterial nerve, inhibit LPS-induced TNF release in mice [7]. According to Tracey and coworkers, the splenic arterial nerve activity is directly controlled by the cholinergic anti-inflammatory pathway (CAP) originating from the efferent branch of the vagus [6]. While vagal regulation of inflammatory tone and inflammatory reflex has received much attention, others have disputed the connections between vagus and splenic arterial nerve. Some authors have shown that denervation of the splenic arterial nerve in mice led to the inhibition of the CAP [7]. However, Martelli et al. have challenged this view by showing that the splenic arterial nerve was not directly connected to the vagus [8] but rather emerged as an independent branch of the greater splanchic nerve which controls splenic arterial nerve activity [9,10]. These authors also counter the view that neural sensing of inflammatory markers is humoral and not neural [11]. Furthermore, it is disputed whether the efferent arm of the inflammatory reflex response is sympathetic or parasympathetic.

Electrostimulation of the vagus nerve has been shown to relieve symptoms of rheumatoid arthritis in a clinical trial [12]. However, there are concerns that stimulation of the vagus nerve can produce undesired, non-specific CNS effects because the vagus nerve is comprised predominantly of afferent fibers and innervates other tissues in addition to the spleen, including the heart, liver and gastrointestinal tract.

Electrical stimulation of the splenic nerves is associated with vascular responses of the spleen [13]. References [7,14,15,16] describe electrical stimulation of the splenic arterial nerves for the treatment of inflammatory disorders. However, these approaches are not ideal. This is because the splenic artery runs along the pancreas and is generally in direct contact with the pancreas, and the nerve plexus surrounding the splenic artery also innervates the pancreas and other structures, so stimulation of the splenic arterial nerve may be associated with surgical injury or damage to the pancreas and off-target effects. Moreover, the proximity of the pancreas and other structures to the splenic artery limits the available space in which an implantable device for electrical stimulation can be provided, and thus constrains the design of any such implantable device.

Thus, there is a need for further and improved ways of stimulating neural activity in nerves associated with the splenic artery for the treatment of disorders, such as disorders associated with inflammation.

SUMMARY OF THE INVENTION

The inventors have found a new way of stimulating splenic arterial nerves with minimized surgical injury or damage to organs, such as the pancreas. This new way involves applying electrical signals to splenic arterial nerves at sites where the splenic artery is not in direct contact with the pancreas. For example, the splenic artery, which runs along the surface of the pancreas, is generally in direct contact with the pancreas, but separates at certain positions from the surface of the pancreas in loop-like structures (herein referred to as splenic arterial loops). The splenic arterial loops are therefore particularly advantageous sites for applying electrical signal to modulate the neural activity of the splenic arterial nerves. The inventors also found that stimulation of the neural activity of the splenic arterial nerve is capable of modulating the level of inflammatory cytokines (e.g. TNFα) and increasing survival of animals in an endotoxemic (LPS) shock model. Thus, the invention provides an improved way of reducing inflammation with a reduced risk of surgical trauma to the patient. The invention is useful for the treatment of disorders, such as disorders associated with inflammation or immune-mediated inflammatory diseases.

Applying electrical signals to splenic arterial nerves at sites where the splenic artery is not in direct contact with the pancreas is also advantageous in that it provides additional flexibility in the design of at least a part of the system for applying the electrical signals (e.g. neural interface 10, implantable device 106) due to the additional space available around the splenic artery. For example, the additional space may allow for a larger battery to be implanted which is capable of delivering electrical signals for a longer period of time.

Thus, the invention provides a system for stimulating the neural activity of a splenic arterial nerve. The system comprises at least one electrode in signaling contact with the nerve at a site where the splenic artery is not in direct contact with the pancreas, and at least one controller electrically coupled to the at least one electrode. The at least one controller configured to control the operation of the least one electrode to apply an electrical signal to the nerve. The electrical signal produces an improvement in a physiological parameter in the subject, wherein the improvement in the physiological parameter is one or more of the group consisting of: a reduction in pro-inflammatory cytokines, an increase in anti-inflammatory cytokines, an increase in catecholamines, changes in immune cell population or immune cell surface co-stimulatory molecules, a reduction in factors involved in the inflammation cascade, and/or a reduction in immune response mediators. Assessments such as disease activity score or clinical score may be used by clinicians to measure disease activity, which may change in response to application of an electrical signal to the nerve, which in turn produces an improvement in a physiological parameter in the subject.

The invention also provides a method for treating a disorder associated with inflammation in a subject. The method comprises providing a system of the invention, positioning at least one electrode in signaling contact with a splenic arterial nerve at a site where the splenic artery is not in direct contact with the pancreas, and controlling the operation of the least one electrode with at least one controller to apply an electrical signal to the nerve to stimulate neural activity.

The invention also provides a method of reversibly stimulating neural activity in a splenic arterial nerve, wherein the nerve. The method comprises providing a system of the invention, positioning the at least one electrode in signaling contact with the nerve is at a site where the splenic artery is not in direct contact with the pancreas, and controlling the operation of the least one electrode with at least one controller to apply an electrical signal to the nerve to stimulate neural activity.

The invention also provides a method for determining whether a neural interface is correctly placed in signaling contact with a splenic arterial nerve. The method comprises providing the system of the invention, positioning the neural interface in signaling contact with the nerve at a site where the splenic artery is not in direct contact with the pancreas, controlling the operation of the least one electrode with at least one controller to apply an electrical signal to the nerve, determining that a change in blood flow rate in the spleen, and/or splenic artery, and/or splenic vein, a decrease in spleen volume, an increase in neural activity in the nerve, or a change in impedance of the at least one electrode has been detected, and indicating to an operator that the neural interface had been placed correctly in signaling contact with the nerve.

The invention also provides a computer-implemented method for treating disorders associated with inflammation in a subject. The method comprises controlling the operation of at least one electrode of the system of the invention to apply a signal to a splenic arterial nerve at a site where the splenic artery is not in direct contact with the pancreas to stimulate neural activity.

The invention also provides a computer-implemented method of reversibly stimulating neural activity in a splenic arterial nerve. The method comprises controlling the operation of at least one electrode of a system of the invention to apply a signal to the nerve at a site where the splenic artery is not in direct contact with the pancreas to stimulate neural activity.

The invention also provides a computer-implemented method of determining whether a neural interface is correctly placed in signaling contact with a splenic arterial nerve. The method comprises controlling the operation of the at least one electrode of the system of the invention to apply a electrical signal to the nerve at a site where the splenic artery is not in direct contact with the pancreas, determining that a change in blood flow rate in the spleen, splenic artery, splenic vein, a decrease in spleen volume, an increase in neural activity in the nerve, or a change in impedance of the at least one electrode has been detected, and indicating to an operator that the neural interface had been placed correctly in signaling contact with the nerve.

The invention also provides a neurostimulatory electrical signal for use in treating a disorder, such as a disorder associated with inflammation, in a subject, wherein the electrical signal is any electrical signal according the invention.

The invention also provides a modified splenic arterial nerve to which a system of the invention is in signaling contact, wherein the at least one electrode is in signaling contact with the nerve and so the nerve can be distinguished from the nerve in its natural state, and wherein the nerve is located in a subject who suffers from, or is at risk of, a disorder, such as a disorder associated with inflammation.

The invention also provides a modified splenic arterial nerve, bounded by a nerve membrane, comprising a distribution of potassium and sodium ions movable across the nerve membrane to alter the electrical membrane potential of the nerve so as to propagate an action potential along the nerve in a normal state; wherein at least a portion of the nerve is subject to the application of a temporary external electrical field which modifies the concentration of potassium and sodium ions within the nerve, causing depolarization of the nerve membrane, thereby, in a disrupted state, temporarily generating an action potential de novo across that portion; wherein the nerve returns to its normal state once the external electrical field is removed.

The invention also provides a modified splenic arterial nerve, obtainable by stimulating neural activity of the nerve according to a method of the invention.

The invention also provides a neural interface suitable for placement around a plurality of splenic arterial nerves at a site where the splenic artery is not in direct contact with the pancreas, where the neural interface fully circumvents the plurality of splenic arterial nerves and comprises at least one electrode.

The invention also provides a neural interface suitable for placement around at least one splenic arterial nerve and the splenic artery at a site where the splenic artery is not in direct contact with the pancreas, where the neural interface circumvents the splenic artery by at least 50%, preferably at least 75%, and comprises at least one electrode.

The invention also provides a method of controlling a system of the invention which is placed in signaling contact with a splenic arterial nerve, comprising a step of sending control instructions to the system, in response to which the system applies a signal to the nerve.

DETAILED DESCRIPTION OF THE INVENTION

The Nerves Surrounding the Spleen

Innervation of the spleen is primarily sympathetic or noradrenergic, with peptide neurons likely representing the bulk of the remaining neurons. The human spleen is innervated by the splenic plexus surrounding the splenic artery. The splenic artery is embedded within adipose and connective tissue and is generally in direct contact with the pancreas. The splenic artery is covered with nervous tissue, which is derived from the coeliac plexus and continues with the splenic artery to the spleen as the splenic plexus. The splenic plexus enters the spleen at the hilum where the splenic artery diverges in terminal branches and the splenic plexus continues with these branches into the parenchyma of the spleen.

The splenic plexus includes several nerve fascicles which circumvent the main splenic artery from celiac artery to spleen, each nerve fascicle comprising a small bundle of nerve fibers. A nerve fascicle (or known as a peri-arterial nerve fascicle) that circumvents the splenic nerve is referred to herein as a splenic arterial nerve.

The course of the splenic artery is variable. In general, it tends to run along the surface of the pancreas and is generally in direct contact with the pancreas. Between the site of origin and the entry point at the hilum, the splenic artery can separate from the surface of the pancreas at certain positions, such that the splenic artery is not in direct contact with the pancreas. For example, at certain positions, the splenic artery may be separated from the surface of the pancreas by a distance of about 0.5 cm to about 4 cm, and the intervening space is filled by adipose tissue and/or connective tissue. At these positions, the splenic artery may protrude from the pancreas to form loop-like structures, and a loop-like structure is herein referred to as a splenic arterial loop.

A splenic arterial loop is characterized by being separated by a distance of, for example, $\geq 0.5$ cm from the surface of the pancreas, and this distance is calculated from the inner curvature of the splenic artery to the surface of the pancreas. The intervening space is filled by adipose tissue and/or connective tissue.

The application of an electrical signal to this site is advantageous since it makes the isolation of the nerve plexus associated with the splenic artery more straight forward. This application site is also expected to make surgery safer, from the perspective of reducing surgical injury to the pancreas.

In some embodiments, the splenic arterial loop is separated from the surface of the pancreas by a distance of $\geq 1$ cm, e.g. about 1-4 cm, preferably about 1.5 cm, where this is the distance between the inner curvature on top of the loop and the surface of the pancreas. This distance may be referred to as the height of the loop, as described herein.

A splenic arterial loop may have a neck of about $\geq 0.5$ cm, where, in this context, "neck" refers to the direct distance between the inner curvature of the first leg of the loop (the position at which the splenic artery separates from the surface of the spleen) and the inner curvature of the second leg of the loop (the position at which the splenic artery comes back into direct contact with the spleen). In some embodiments, the neck is $\geq 0.55$ cm, $\geq 0.6$ cm, $\geq 0.65$ cm, $\geq 0.7$ cm, $\geq 0.75$ cm, $\geq 0.8$ cm, $\geq 0.85$ cm, $\geq 0.9$ cm, $\geq 0.95$ cm, $\geq 1$ cm, $\geq 1.1$ cm, $\geq 1.2$ cm, $\geq 1.3$ cm, $\geq 1.4$ cm, $\geq 1.5$ cm, $\geq 1.6$ cm, $\geq 1.7$ cm, $\geq 1.8$ cm, $\geq 1.9$ cm, $\geq 2.0$ cm. In some embodiments, the splenic arterial loop may have a neck in the range of about 1.1 cm to about 3.0 cm.

The number of splenic arterial loops can vary between human subjects, but, in general, there appears to be a positive correlation between the number of splenic arterial loops and the age of a subject. Typically, splenic arterial loops are more frequently observed in human subjects over the age of 45.

The splenic plexus associated with the arterial vasculature has been shown to innervate the spleen and regulate the production of inflammatory cytokines. Thus, by stimulating neural activity in a nerve associated with the splenic plexus, it is possible to modulate the levels of pro- and anti-inflammatory molecules (e.g. cytokines) to achieve therapeutic effects, such as reducing inflammation. In particular, stimulation of one or more nerves associated with the splenic plexus decreases the production and secretion of pro-inflammatory cytokines, and increases the production and secretion of anti-inflammatory cytokines, thereby assisting in treating conditions associated with an imbalanced pro- and anti-inflammatory cytokine profile, e.g. disorders associated with inflammation.

The invention involves applying electrical signals to the splenic arterial nerve at sites where the splenic artery is not in direct contact with the pancreas, as described above. Preferably, the signal application site is at a splenic arterial loop.

The stimulation of neural activity in the splenic plexus associated with the arterial vasculature is typically achieved by surgical intervention. The implantation of systems or devices for modulating neural activity at a site on the splenic artery that is separated from the surface of the pancreas enables the stimulation of the desired neural activity in the splenic arterial nerve at a site more surgically accessible than previously acknowledged. Signal application at these sites therefore has the advantages of significantly reducing the risk of surgical trauma, for example, pancreatic trauma, because the surgeon does not need to surgically excise the splenic artery from the surface of the pancreas.

In some embodiments, the signal application site may be at one or more nerves adjacent to one of said sites.

In some embodiments, the signal application sites may be at one or more nerves adjacent to a plurality of said sites. In some embodiments, each of the plurality of independent sites may be stimulated with independent systems, devices or methods of the invention. In some embodiments, each of the plurality of said sites may be stimulated by a single system, device or method of the invention.

In some embodiments, the signal may be applied to one or more nerves in each of the plurality of sites, simultaneously, sequentially or separately.

Simultaneously may refer to the application of the signal at each of the plurality of sites at substantially the same time, i.e. within the error of possible delay, the signal is intended to be applied to each of the plurality of sites at exactly the same time. Separately may refer to the application of the signal to each of the plurality of sites independently of one another i.e. the signals are not to be applied in a concerted sequence. Each of the signals is transmitted to each of the sites independently. It is to be understood that the application of separate signals can result in each or several of the plurality of sites coincidently receiving a signal at substantially the same time. Sequentially may refer to the application of the signal to each of the plurality of sites in a defined "sequence". This may involve the application of signals to several of the plurality of independent sites at substantially the same time.

Furthermore, the inventors have found that pre-operative protocols may be used to identify the most optimal position of the splenic artery for implanting a system or device of the invention for stimulating neural activity. The most optimal site may be the position at which the splenic artery is separated from the pancreas and is most accessible by surgery, thereby carrying the lowest risk of surgical trauma.

For example, this may be the splenic arterial loop with the greatest separating distance from the surface of the spleen. The most optimal site may be identified by performing a pre-operative CT scan or other procedures known in the art.

Where the invention refers to a modified splenic nerve, the nerve is ideally present in situ in a subject.

Stimulation of a Nerve Supplying the Spleen

The invention involves applying an electrical signal to a splenic arterial nerve at certain sites described herein, to stimulate neural activity.

Stimulation refers to where signaling activity of at least part of the nerve being increased compared to baseline neural activity in that part of the nerve, where baseline neural activity is the signaling activity of the nerve in the subject prior to any intervention. Put another way, stimulation results in the creation of neural activity which increases the total neural activity in that part of the nerve.

"Neural activity" of a nerve refers to the signaling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

Stimulation typically involves increasing neural activity e.g. generating action potentials beyond the point of the stimulation in at least a part of the nerve. At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in its normal state, wherein action potentials propagate from point to adjacent point along the axon, and which can be observed using conventional experimentation.

One way of characterizing a stimulation of neural activity is a distribution of potassium and sodium ions at one or more points in the axon, which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization of the nerve membrane that would not otherwise occur. The depolarization of the nerve membrane caused by the temporary external electrical field generates de novo action potential across that point. This is a nerve operating in a disrupted state, which can be observed by a distribution of potassium and sodium ions at a point in the axon (the point which has been stimulated) that has an electrical membrane potential that is not influenced or determined by the electrical membrane potential of an adjacent point.

Stimulation of neural activity is thus understood to be increasing neural activity from continuing past the point of signal application. Thus, the nerve at the point of signal application is modified in that the nerve membrane is reversibly depolarized by an electric field, such that a de novo action potential is generated and propagates through the modified nerve. Hence, the nerve at the point of signal application is modified in that a de novo action potential is generated.

When the signal is an electrical signal, the stimulation is based on the influence of electrical currents (e.g. charged particles, which may be one or more electrons in an electrode in signaling contact with the nerve, or one or more ions outside the nerve or within the nerve, for instance) on the distribution of ions across the nerve membrane.

Stimulation of neural activity encompasses full stimulation of neural activity in the nerve—that is, embodiments where the total neural activity is increased in the whole nerve.

Stimulation of neural activity may be partial stimulation. Partial stimulation may be such that the total signaling activity of the whole nerve is partially increased, or that the total signaling activity of a subset of nerve fibers of the nerve is fully increased (i.e. there is no neural activity in that subset of fibers of the nerve), or that the total signaling of a subset of nerve fibers of the nerve is partially increased compared to baseline neural activity in that subset of fibers of the nerve. For example, an increase in neural activity of ≤5%, ≤10%, ≤15%, ≤20%, ≤25%, ≤30%, ≤35%, ≤40%, ≤45%, ≤50%, ≤60%, ≤70%, ≤80%, ≤90% or ≤95%, or an increase of neural activity in a subset of nerve fibers of the nerve. Neural activity may be measured by methods known in the art, for example, by the number of action potentials which propagate through the axon and/or the amplitude of the local field potential reflecting the summed activity of the action potentials.

Stimulation of neural activity may be an alteration in the pattern of action potentials. It will be appreciated that the pattern of action potentials can be modulated without necessarily changing the overall frequency or amplitude. For example, stimulation of neural activity may be (at least partially) corrective. As used herein, "corrective" is taken to mean that the modulated neural activity alters the neural activity towards the pattern of neural activity in a healthy subject, and this is called axonal modulation therapy. That is, upon cessation of signal application, neural activity in the nerve more closely resembles (ideally, substantially fully resembles) the pattern of action potentials in the nerve observed in a healthy subject than prior to signal application. Such corrective stimulation can be any stimulation as defined herein.

For example, application of a signal may result in an increase on neural activity, and upon cessation of signal application the pattern of action potentials in the nerve resembles the pattern of action potentials observed in a healthy subject. By way of further example, application of the signal may result in neural activity resembling the pattern of action potentials observed in a healthy subject and, upon cessation of the signal, the pattern of action potentials in the nerve remains the pattern of action potentials observed in a healthy subject.

Stimulation of neural activity may comprise altering the neural activity in various other ways, for example increasing a particular part of the baseline neural activity and/or stimulating new elements of activity, for example: in particular intervals of time, in particular frequency bands, according to particular patterns and so forth.

One advantage of the invention is that stimulation of neural activity is reversible. Hence, the modulation of neural activity is not permanent. For example, upon cessation of the application of a signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible stimulation, the neural activity returns substantially fully to baseline neural activity. That is, the neural activity following cessation of the application of a signal is substantially the same as the neural activity prior to a signal being applied. Hence, the nerve or the portion of the nerve has regained its normal physiological capacity to propagate action potentials.

In other embodiments, stimulation of neural activity may be substantially persistent. As used herein, "persistent" is taken to mean that the neural activity has a prolonged effect. For example, upon cessation of the application of a signal, neural activity in the nerve remains substantially the same as when the signal was being applied—i.e. the neural activity during and following signal application is substantially the same. Reversible modulation is preferred.

Application in Therapy

The invention is useful for treating disorders, such as disorders associated with inflammation. Disorders associated with inflammation typically present with an imbalance of pro—and anti-inflammatory cytokine profiles compared to the physiological homeostatic state, e.g. increased pro-inflammatory cytokines levels and/or decreased anti-inflammatory cytokines levels compared to the normal physiological homeostatic state. Examples of these disorders include inflammatory disorders, e.g. chronic or acute inflammatory disorders. The invention is also useful in the treatment of acute inflammatory episodes associated with medical conditions. For the purpose of the present invention, unless otherwise indicated "inflammatory disorders" refers to both chronic inflammatory disorders and acute inflammatory episodes associated with medical conditions.

Thus, the invention is useful for treating subjects suffering from, or are at risk in developing, disorders associated with inflammation, e.g. inflammatory disorders. The invention may treat or ameliorate the effects of the disorders associated with inflammation by reducing inflammation. This may be achieved by decreasing the production and release of pro-inflammatory cytokines, and/or increasing the production and release of anti-inflammatory cytokines, from the spleen by reversibly electrically stimulating the splenic arterial as described herein. In particularly preferred embodiments, the application site is at a nerve adjacent to a splenic arterial loop.

Inflammatory disorders include autoimmune disorders, such as arthritis (e.g. rheumatoid arthritis, osteoarthritis, psoriatic arthritis), Grave's disease, myasthenia gravis, thryoiditis, systemic lupus erythematosus, Goodpasture's syndrome, Behcets's syndrome, allograft rejection, graft-versus-host disease, ankylosing spondylitis, Berger's disease, diabetes including Type I diabetes, Reitier's syndrome, spondyloarthropathy psoriasis, multiple sclerosis, Inflammatory Bowel Disease, Crohn's disease, Addison's disease, autoimmune mediated hair loss (e.g., alopecia areata) and ulcerative colitis.

Certain examples of inflammatory disorders include diseases involving the gastrointestinal tract and associated tissues, such as appendicitis, peptic, gastric and duodenal ulcers, peritonitis, pancreatitis, ulcerative, pseudomembranous, acute and ischemic colitis, inflammatory bowel disease, diverticulitis, cholangitis, cholecystitis, Crohn's disease, Whipple's disease, hepatitis, abdominal obstruction, volvulus, post-operative ileus, ileus, celiac disease, periodontal disease, pernicious anemia, amebiasis and enteritis.

Further examples of inflammatory disorders include diseases of the bones, joints, muscles and connective tissues, such as the various arthritides and arthralgias, osteomyelitis, gout, periodontal disease, rheumatoid arthritis, spondyloarthropathy, ankylosing spondylitis and synovitis.

Further examples include systemic or local inflammatory diseases and conditions, such as asthma, allergy, anaphylactic shock, immune complex disease, sepsis, septicemia, endotoxic shock, eosinophilic granuloma, granulomatosis, organ ischemia, reperfusion injury, organ necrosis, hay fever, cachexia, hyperexia, septic abortion, HIV infection, herpes infection, organ transplant rejection, disseminated bacteremia, Dengue fever, malaria and sarcoidosis.

Other examples include diseases involving the urogential system and associated tissues, such as diseases that include epididymitis, vaginitis, orchitis, urinary tract infection, kidney stone, prostatitis, urethritis, pelvic inflammatory bowel disease, contrast induced nephropathy, reperfusion kidney injury, acute kidney injury, infected kidney stone, herpes infection, and candidiasis.

Other examples include involving the respiratory system and associated tissues, such as bronchitis, asthma, hay fever, ventilator associated lung injury, cystic fibrosis, adult respiratory distress syndrome, pneumonitis, alvealitis, epiglottitis, rhinitis, achlasia, respiratory syncytial virus, pharyngitis, sinusitis, pneumonitis, alvealitis, influenza, pulmonary embolism, hyatid cysts and/or bronchiolitis.

Further examples are dermatological diseases and conditions of the skin (such as burns, dermatitis, dermatomyositis, burns, cellulitis, abscess, contact dermatitis, dermatomyositis, warts, wheal, sunburn, urticaria warts, and wheals); diseases involving the cardiovascular system and associated tissues, (such as myocardial infarction, cardiac tamponade, vasulitis, aortic dissection, coronary artery disease, peripheral vascular disease, aortic abdominal aneurysm, angiitis, endocarditis, arteritis, atherosclerosis, thrombophlebitis, pericarditis, myocarditis, myocardial ischemia, congestive heart failure, periarteritis nodosa, and rheumatic fever, filariasis thrombophlebitis, deep vein thrombosis); as well as various cancers, tumors and proliferative disorders (such as Hodgkin's disease), nosocomial infection; and, in any case the inflammatory or immune host response to any primary disease.

Other examples of inflammatory disorders include diseases involving the central or peripheral nervous system and associated tissues, such as Alzheimer's disease, depression, multiple sclerosis, cerebral infarction, cerebral embolism, carotid artery disease, concussion, subdural hematoma, epidural hematoma, transient ischemic attack, temporal arteritis, spinal cord injury without radiological finding (SCIWORA), cord compression, meningitis, encephalitis, cardiac arrest, Guillain-Barre, spinal cord injury, cerebral venous thrombosis and paralysis.

Conditions associated with a particular organ such as eye or ear may also include an immune or inflammatory response such as conjunctivitis, iritis, glaucoma, episcleritis, acute retinal occlusion, rupture globe, otitis media, otitis externa, uveitis and Meniere's disease.

Another example of an inflammatory disorder is post-operative ileus (POI). POI is experienced by the vast majority of patients undergoing abdominal surgery. POI is characterized by transient impairment of gastro-intestinal (GI) function along the GI tract as well pain and discomfort to the patient and increased hospitalization costs.

The impairment of GI function is not limited to the site of surgery, for example, patients undergoing laparotomy can experience colonic or ruminal dysfunction. POI is at least in part mediated by enhanced levels of pro-inflammatory cytokines and infiltration of leukocytes at the surgical site. Neural inhibitory pathways activated in response to inflammation contribute to the paralysis of secondary GI organs distal to the site of surgery. Stimulation of neural activity as taught herein may thus be effective in the treatment or prevention of POI.

The invention is particularly useful in treating autoimmune disorders (e.g. rheumatoid arthritis, osteoarthritis, psoriatic arthritis, spondyloarthropathy, ankylosing spondylitis, psoriasis, systemic lupus erythematosus (SLE), multiple sclerosis, Inflammatory Bowel Disease, Crohn's disease, and ulcerative colitis) and sepsis.

This invention is particularly useful for treating B cell mediated autoimmune disorders (e.g. systemic lupus erythematosus (SLE) and rheumatoid arthritis (RA)).

The invention is particularly useful for treating inflammatory conditions associated with bacterial infections. For example, the invention is particularly useful for treating inflammatory conditions caused or exacerbated by *Escherichia coli, Staphylococcus aureus, Pneumococcus, Haemophilus influenza, Neisseria meningitides, Streptococcus pneumonia*, Methicillin-resistant *Staphylococcus aureus* (MRSA), *Klebsiella* or *Enterobacter* infection.

Treatment of the inflammatory disorder can be assessed in various ways, but typically involves determining an improvement in one or more physiological parameters of the subject.

Useful physiological parameters of the invention may be one or more of the group consisting of: the level of a pro-inflammatory cytokine, the level of an anti-inflammatory cytokine, the level of a catecholamine, the level of an immune cell population, the level of an immune cell surface co-stimulatory molecule, the level of a factor involved in the inflammation cascade, the level of an immune response mediator, and the rate of splenic blood flow.

As used herein, an "improvement in a determined physiological parameter" is taken to mean that, for any given physiological parameter, an improvement is a change in the value of that parameter in the subject towards the normal value or normal range for that value—i.e. towards the expected value in a healthy subject. As used herein, "worsening of a determined physiological parameter" is taken to mean that, for any given physiological parameter, worsening is a change in the value of that parameter in the subject away from the normal value or normal range for that value—i.e. away from the expected value in a healthy subject.

Improvement in a determined physiological parameter according to the invention is indicated by one or more of the group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in the level of an immune response mediator and a decrease in splenic blood flow. The invention might not lead to a change in all of these parameters.

By stimulating a splenic arterial nerve at a site where the splenic artery is not in direct contact with the pancreas, the spleen may: (a) decrease the secretion of a pro-inflammatory cytokine compared to baseline secretion; and/or (b) increase the secretion of an anti-inflammatory cytokine compared to baseline secretion. For example, the decrease in a pro-inflammatory cytokine secretion may be by: $\leq 5\%$, $\leq 10\%$, $\leq 15\%$, $\leq 20\%$, $\leq 25\%$, $\leq 30\%$, $\leq 35\%$, $\leq 40\%$, $\leq 45\%$, $\leq 50\%$, $\leq 60\%$, $\leq 70\%$, $\leq 80\%$, $\leq 90\%$ or $\leq 95\%$. The increase in an anti-inflammatory cytokine secretion may be by: $\leq 5\%$, $\leq 10\%$, $\leq 15\%$, $\leq 20\%$, $\leq 25\%$, $\leq 30\%$, $\leq 35\%$, $\leq 40\%$, $\leq 45\%$, $\leq 50\%$, $\leq 60\%$, $\leq 70\%$, $\leq 80\%$, $\leq 90\%$, $\leq 95\%$, $\leq 100\%$, $\leq 150\%$ or $\leq 200\%$.

Once the cytokine is secreted into the circulation, its concentration in circulation is diluted. Stimulation of the splenic arterial nerve may result in: (a) a decrease in the level of a pro-inflammatory cytokine in the plasma or serum by $\leq 5\%$, $\leq 10\%$, $\leq 15\%$, $\leq 20\%$, $\leq 25\%$, $\leq 30\%$, $\leq 35\%$, $\leq 40\%$, $\leq 45\%$, $\leq 50\%$, $\leq 60\%$, $\leq 70\%$, $\leq 80\%$, $\leq 90\%$, or $\leq 95\%$; and/or (b) an increase in the level of an anti-inflammatory cytokine in the plasma or serum by $\leq 5\%$, $\leq 10\%$, $\leq 15\%$, $\leq 20\%$, $\leq 25\%$, $\leq 30\%$, $\leq 35\%$, $\leq 40\%$, $\leq 45\%$, $\leq 50\%$, $\leq 60\%$, $\leq 70\%$, $\leq 80\%$, $\leq 90\%$, $\leq 95\%$, $\leq 100\%$, $\leq 150\%$ or $\leq 200\%$. Preferably the level in the serum is measured.

By stimulating the splenic arterial nerve, the level of catecholamine (e.g. norepinephrine or epinephrine), e.g. its level in the spleen in the spleen, may increase, for example, by: $\leq 5\%$, $\leq 10\%$, $\leq 15\%$, $\leq 20\%$, $\leq 25\%$, $\leq 30\%$, $\leq 35\%$, $\leq 40\%$, $\leq 45\%$, $\leq 50\%$, $\leq 60\%$, $\leq 70\%$, $\leq 80\%$, $\leq 90\%$, $\leq 95\%$, $\leq 100\%$, $\leq 150\%$ or $\leq 200\%$.

For example, the inventors found that stimulating a splenic arterial nerve can decrease the level of a pro-inflammatory cytokine (e.g. TNFα) in the serum by 30%-60%.

Pro-inflammatory cytokines are known in the art. Examples of these include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors.

Anti-inflammatory cytokines are also known in the art. Examples of these include IL-4, IL-10, IL-17, IL-13, IL-1α, and TNFα receptor.

It will be recognized that some of pro-inflammatory cytokines may act as anti-inflammatory cytokines in certain circumstances, and vice-versa. Such cytokines are typically referred to as pleiotropic cytokines.

Factors involved in immune responses may be useful measurable parameters for the invention, for example, TGF, PDGF, VEGF, EGF, FGF, I-CAM, nitric oxide.

Chemokines may also be useful measurable parameters for the invention, such as 6cKine and MIP3beta, and chemokine receptors, including CCR7 receptor.

Changes in immune cell population (Langerhans cells, dendritic cells, lymphocytes, monocytes, macrophages), or immune cell surface co-stimulatory molecules (Major Histocompatibility, CD80, CD86, CD28, CD40) may also be useful measurable parameters for the invention. Applying a signal to the nerves according to the invention can cause reduction in total counts of circulating or tissue-specific (e.g. joint-specific in the case of rheumatoid arthritis) leukocytes (including monocytes and macrophages, lymphocytes, neutrophils, etc.).

Factors involved in the inflammatory cascade may also be useful measurable parameters for the invention. For example, the signal transduction cascades include factors such as NFκ-B, Egr-1, Smads, toll-like receptors, and MAP kinases.

Methods of assessing these physiological parameters are known in the art. Detection of any of the measurable parameters may be done before, during and/or after modulation of neural activity in the nerve.

For example, a cytokine, chemokine, or a catecholamine (e.g. norepinephrine or epinephrine) may be directly detected, e.g. by ELISA. Alternatively, the presence or amount of a nucleic acid, such as a polyribonucleotide, encoding a polypeptide described herein may serve as a measure of the presence or amount of the polypeptide. Thus, it will be understood that detecting the presence or amount of a polypeptide will include detecting the presence or amount of a polynucleotide encoding the polypeptide.

Quantitative changes of the biological molecules (e.g. cytokines) can be measured in a living body sample such as urine or plasma. Detection of the biological molecules may be performed directly on a sample taken from a subject, or the sample may be treated between being taken from a subject and being analyzed. For example, a blood sample may be treated by adding anti-coagulants (e.g. EDTA), followed by removing cells and cellular debris, leaving plasma containing the relevant molecules (e.g. cytokines) for analysis. Alternatively, a blood sample may be allowed to coagulate, followed by removing cells and various clotting factors, leaving serum containing the relevant molecules (e.g. cytokines) for analysis.

In the embodiments where the signal is applied whilst the subject is asleep, the invention may involve determining the subject's circadian rhythm phase markers, such as the level of cortisol (or its metabolites thereof), the level of melatonin (or its metabolites thereof) or core body temperature. Cortisol or melatonin levels can be measured in the blood (e.g. plasma or serum), saliva or urine. Methods of determining the levels of these markers are known in the art, e.g. by enzyme-linked immunosorbent assay (ELISA) or radioimmunoassay. If measurements of the subject's circadian rhythm phase markers indicate circadian oscillations of inflammatory markers which may beneficially be regulated by application of a signal with a system of the invention, then application of the signal at night at a suitable periodicity according to the subject's circadian rhythm may be appropriate.

As used herein, a physiological parameter is not affected by the modulation (e.g. stimulation) of the splenic neural activity if the parameter does not change (in response to nerve modulation) from the normal value or normal range for that value of that parameter exhibited by the subject or subject when no intervention has been performed i.e. it does not depart from the baseline value for that parameter. Such a physiological parameter may be arterial pressure, heart rate or glucose metabolism. Suitable methods for determining changes in any these physiological parameters would be appreciated by the skilled person.

The skilled person will appreciate that the baseline for any neural activity or physiological parameter in an subject need not be a fixed or specific value, but rather can fluctuate within a normal range or may be an average value with associated error and confidence intervals. Suitable methods for determining baseline values are well known to the skilled person.

As used herein, a physiological parameter is determined in a subject when the value for that parameter exhibited by the subject at the time of detection is determined. A detector (e.g. a physiological sensor subsystem, a physiological data processing module, a physiological sensor, etc.) is any element able to make such a determination.

Thus, in certain embodiments, the invention further comprises a step of determining one or more physiological parameters of the subject, wherein the signal is applied only when the determined physiological parameter meets or exceeds a predefined threshold value. In such embodiments wherein more than one physiological parameter of the subject is determined, the signal may be applied when any one of the determined physiological parameters meets or exceeds its threshold value, alternatively only when all of the determined physiological parameters meet or exceed their threshold values. In certain embodiments wherein the signal is applied by a system of the invention, the system further comprises at least one detector configured to determine the one or more physiological parameters of the subject.

In certain embodiments, the physiological parameter is an action potential or pattern of action potentials in a nerve of the subject, wherein the action potential or pattern of action potentials is associated with the condition that is to be treated.

It will be appreciated that any two physiological parameters may be determined in parallel embodiments, the controller is coupled detect the pattern of action potentials tolerance in the subject.

A predefined threshold value for a physiological parameter is the minimum (or maximum) value for that parameter that must be exhibited by a subject or subject before the specified intervention is applied.

For any given parameter, the threshold value may be defined as a value indicative of a pathological state or a disease state. The threshold value may be defined as a value indicative of the onset of a pathological state or a disease state. Thus, depending on the predefined threshold value, the invention can be used as a treatment. Alternatively, the threshold value may be defined as a value indicative of a physiological state of the subject (that the subject is, for example, asleep, post-prandial, or exercising). Appropriate values for any given physiological parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that physiological parameter than the predefined threshold value.

A subject of the invention may, in addition to having an implant, receive medicine for their condition.

For instance, a subject having an implant according to the invention may receive an anti-inflammatory medicine (which will usually continue medication which was occurring before receiving the implant). Such medicines include, nonsteroidal anti-inflammatory drugs (NSAIDs), steroids, 5ASAs, disease-modifying-anti-inflammatory drugs (DMARDs) such as azathioprine, methotrexate and cyclosporin, biological drugs like infliximab and adalimumab, and the new oral DMARDs like Jak inhibitors. Thus the invention provides the use of these medicines in combination with a system of the invention.

Suitable Forms of an Electrical Signal

The invention uses an electrical signal applied via at least one electrode which placed in signaling contact with a splenic arterial nerve at a site where the splenic artery is not in direct contact with the pancreas. As used herein, "signaling contact" is where at least part of the electrical signal applied via the at least one electrode is received at the nerve.

Electrical signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of the nerve or fibers thereof, or other nerve tissue to which the signal is applied, to conduct action potentials when application of the signal ceases, even if that conduction is in practice artificially stimulated as a result of application of the non-destructive signal.

Electrical signals applied according to the invention may be a voltage or a current waveform.

The electrical signal may be characterized by one or more electrical signal parameters. The electrical signal parameters include waveform, frequency, and amplitude.

Alternatively or additionally, the electrical signal may be characterized by the pattern of application of the electrical signal to the nerve. The pattern of application refers to the timing of the application of the electrical signal to the nerve. The pattern of application may be continuous application or periodic application, and/or episodic application.

Episodic application refers to where the electrical signal is applied to the nerve for a discrete number of episodes throughout a day. Each episode may be defined by a set duration or a set number of iterations of the electrical signal.

Continuous application refers to where the electrical signal is applied to the nerve in a continuous manner. Where the electrical signal is applied continuously and episodically, it means that the signal is applied in a continuous manner for each episode of application. In embodiments where the electrical signal is a series of pulses, the gaps between those pulses (i.e. between the pulse width and the phase duration) do not mean the signal is not continuously applied.

Periodic application refers to where the electrical signal is applied to the nerve in a repeating pattern (e.g. an on-off pattern). Where the electrical signal is applied periodically and episodically, it means that the signal is applied in a periodic manner for each episode of application.

The inventors found preferred electrical signal parameters and patterns of signal application for stimulating neural activity in a splenic arterial nerve by applying the signal to the application site of the invention, which lead to increase immunosuppressive effects while reducing possible systemic effects when stimulating neural activity in said nerve. The preferred signal parameters and patterns of application are discussed in detail below.

Waveform

Modulation (e.g. stimulation) of a nerve supplying the spleen can be achieved using electrical signals which serve to replicate the normal neural activity of the nerve. Thus, the waveform of the electrical signal comprises one or more pulse trains, each with a defined pulse width. The pulses are preferably square pulses. However, other pulse waveforms such as sawtooth, sinusoidal, triangular, trapezoidal, quasi-trapezodial or complex waveforms may also be used with the invention.

The pulses may be charge-balanced. A charge-balanced pulse refers to a pulse which, over the period of the pulse, applies equal amounts (or thereabouts) of positive and negative charge to the nerve.

The pulses may be symmetric or asymmetric. A symmetric pulse is a pulse where the waveform when applying a positive charge to the nerve is symmetrical to the waveform when applying a negative charge to the nerve. An asymmetric pulse is a pulse where the waveform when applying a positive charge to the nerve is not symmetrical with the waveform when applying a negative charge to the nerve.

The pulses may have a pulse width (of each phase) between 250 and 1000 µs, preferably between 400 and 1000 µs (this can be applicable to both positive and negative phases of the pulse, in the case of a biphasic pulse). For example, the pulse width may be ≤500 µs, ≤600 µs, ≤700 µs, ≤800 µs, ≤900 µs, or ≤1000 µs. Additionally or alternatively, the pulse width may be ≥400 µs, ≥500 µs, ≥600 µs, ≥700 µs, ≥800 µs, or ≥900 µs. Any combination of the upper and lower limits above is also possible.

The pulse width may additionally be limited by the frequency. A pulse width refers to a width (or time duration) of a primary phase of the waveform. In cases where a pulse comprises a first phase that is the primary phase and a second phase which is the recovery phase, for example an anodic and/or a cathodic phase, the pulse width refers to a width (or duration) of the first phase.

If the biphasic pulse is asymmetric, but remains charged balanced, then the areas of the opposing phases must equal. Amplitude (see below) can be reduced, but the pulse width would need to be extended to ensure the area under the curve is matched.

In an exemplary embodiment, the waveform is a pulse train with biphasic, asymmetric, charged balanced square pulses.

Amplitude

For the purpose of the invention, the amplitude is referred to herein in terms of charge density per phase. Charge density per phase applied to the nerve by the electrical signal is defined as the integral of the current over one phase (e.g. over one phase of the biphasic pulse in the case of a charge-balanced biphasic pulse). Thus, charge density per phase applied to the nerve by the electrical signal is the charge per phase per unit of contact area between at least one electrode and the nerve, and also the integral of the current density over one phase of the signal waveform. Put another way, the charge density per phase applied to the nerve by the electrical signal is the charge per phase applied to the nerve by the electrical signal divided by the contact area between at least one electrode (generally the cathode) and the nerve.

The charge density per phase required by the invention represents the amount of energy required to stimulate neural activity in a nerve supplying the spleen to increase immunosuppressive effects.

The inventors found the charge density per phase required to stimulate neural activity in a porcine splenic arterial nerve to be between 5 µC to 150 µC per cm$^2$ per phase or in some cases between 5 µC to 180 µC per cm$^2$ per phase using an extravascular cuff (values may be slightly affected by electrode design). For example, the charge density per phase applied by the electrical signal may be ≤10 µC per cm$^2$ per phase, ≤15 µC per cm$^2$ per phase, ≤20 µC per cm$^2$ per phase, ≤25 µC per cm$^2$ per phase, ≤30 µC per cm$^2$ per phase, ≤40 µC per cm$^2$ per phase, ≤50 µC per cm$^2$ per phase, ≤75 µC per cm$^2$ per phase, ≤100 µC per cm$^2$ per phase, ≤125 µC per cm$^2$ per phase, ≤150 µC per cm$^2$ per phase, or ≤180 µC per cm$^2$ per phase. Additionally or alternatively, the charge density per phase applied by the electrical signal may be ≥5 µC per cm$^2$ per phase, ≥10 µC per cm$^2$ per phase, ≥15 µC per cm$^2$ per phase, ≥20 µC per cm$^2$ per phase, ≥25 µC per cm$^2$ per phase, ≥30 µC per cm$^2$ per phase, ≥40 µC per cm$^2$ per phase, ≥50 µC per cm$^2$ per phase, ≥75 µC per cm$^2$ per phase, ≥100 µC per cm$^2$ per phase, ≥125 µC per cm$^2$ per phase, or ≥150 µC per cm$^2$ per phase. Any combination of the upper and lower limits above is also possible.

The inventors further found the indicated estimation of charge density per phase required to stimulate neural activity in a human splenic arterial nerve to be between approximately 70-1300 μC/cm². For example, the charge density per phase applied by the electrical signal may be ≤80 μC per cm² per phase, ≤140 μC per cm² per phase, ≤170 μC per cm² per phase, ≤230 μC per cm² per phase, ≤250 μC per cm² per phase, ≤300 μC per cm² per phase, ≤350 μC per cm² per phase, ≤400 μC per cm² per phase, ≤450 μC per cm² per phase, ≤500 μC per cm² per phase, ≤1100 μC per cm² per phase, or ≤1300 μC per cm² per phase. Additionally or alternatively, the charge density per phase applied by the electrical signal may be ≥70 μC per cm² per phase, ≥140 μC per cm² per phase, ≥170 μC per cm² per phase, ≥230 μC per cm² per phase, ≥250 μC per cm² per phase, ≥300 μC per cm² per phase, ≥350 μC per cm² per phase, ≥400 μC per cm² per phase, ≥450 μC per cm² per phase, ≥500 μC per cm² per phase, ≥1100 μC per cm² per phase, or ≥1300 μC per cm² per phase. Any combination of the upper and lower limits above is also possible.

The total charge applied to the nerve by the electrical signal in any given time period is a result of the charge density per phase of the signal, in addition to the frequency of the signal, the pattern of application of the signal and the area in contact between at least one electrode and the nerve. The frequency of the signal, the pattern of application of the signal and the area in contact between at least one electrode and the nerve are discussed further herein.

It will be appreciated by the skilled person that the amplitude of an applied electrical signal necessary to achieve the intended stimulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

It would be of course understood in the art that the electrical signal applied to the nerve would be within clinical safety margins (e.g. suitable for maintaining nerve signaling function, suitable for maintaining nerve integrity, and suitable for maintaining the safety of the subject). The electrical parameters within the clinical safety margin would typically be determined by pre-clinical studies.

Episodic Application

Episodic application refers to where the electrical signal is applied to the nerve for a discrete number of episodes throughout a day. The electrical signal according to the invention may be applied for up to a maximum of six episodes per day. For example, the number of episodes of signal application per day may be one, two, three, four, five or six.

The electrical signal may be applied episodically every 2 to 3 hours. For example, the electrical signal may be applied episodically once every 2 hours, 2 hour 15 min, 2 hour 30 min, 2 hour 45 min, 3 hours.

Each episode may be defined by a set duration or a set number of iterations of the electrical signal. In some embodiments, each episode comprises applying to the nerve between 50 and 10000, e.g. between 60 and 3000 pulses of the electrical signal, between 100 and 2400 pulses of the electrical signal, between 200 and 1200 pulses of the electrical signal, between 400 and 600 pulses of the electrical signal, etc. For example, each episode may comprise applying ≤400, ≤800, ≤1200, ≤1600, ≤2000, ≤2400, ≤3000, or ≤10000 pulses of the electrical signal. In another example, each episode may comprise applying ≤200, ≤400, ≤600, ≤800, ≤1000, or ≤1200 pulses of the electrical signal. In a further example, each episode may comprise applying ≤400, ≤425, ≤450, ≤475, ≤500, ≤525, ≤550, ≤575, or ≤600 pulses of the electrical signal.

In other embodiments, each episode comprises between 20 and 40 iterations of the periodic pattern. For example, each episode comprises applying 20, 25, 30, 35, or 40 iterations of the periodic pattern, or any number therebetween. The higher the frequency, the lower the number of iterations.

As mentioned previously, in some embodiments, the episodes may be based on the subject's sleep-wake cycle, in particular the episodes may be whilst the subject is asleep. In some such embodiments, the episodes may be applied between 10 pm and 6 am. The sleep-wake cycle may be measured via known methods by detecting the subject's circadian rhythm phase markers (e.g. cortisol level, melatonin level or core body temperature), and/or a detector for detecting the subject's movements.

Periodic Application

Periodic application refers to where the electrical signal is applied to the nerve in a repeating pattern. The preferred repeating pattern is an on-off pattern, where the signal is applied is applied for a first duration, referred to herein as an 'on' duration, then stopped for a second duration, referred to herein as an 'off' duration, then applied again for the first duration, then stopped again for the second duration, etc.

The periodic on-off pattern preferably has an on duration of between 0.1 and 10 s and an off duration of between 0.5 and 30 s. For example, the on duration (referred as the time during which pulses at a certain frequency and amplitude are delivered to the nerve) may be ≤0.2 s, ≤0.5 s, ≤1 s, ≤2 s, ≤5 s, or ≤10 s. Alternatively or additionally, the on duration may be ≥0.1 s, ≥0.2 s, ≥0.5 s, ≥1 s, ≥2 s, or ≥5 s. Any combination of the upper and lower limits above for the on duration is also possible. For example, the off duration (referred to the time between on periods, during which no pulses are delivered to the nerve) may be ≤1 s, ≤3 s, ≤5 s, ≤10 s, ≤15 s, ≤20 s, ≤25 s, or ≤30 s. Alternatively or additionally, the off duration may be ≥0.5 s, ≥1 s, ≥2 s, ≥5 s, ≥10 s, ≥15 s, ≥20 s, or ≤25 s. Any combination of the upper and lower limits above for the off duration is also possible.

In an exemplary embodiment, the periodic on-off pattern has an on duration of 0.5 s on, and 4.5 sec off. In another example, the periodic on-off pattern has an on duration of 0.5 s on, and 5 sec off for up to 10 Hz pulses. For frequency higher than 10 Hz (for example 30 Hz) an example periodic on-off pattern has an on duration of or 0.1 s on, and an off duration of 3 s. In other words, a ratio of the on duration to the off duration may be 1:5, further preferably wherein the ratio is 1:6, 1:7, 1:8, 1:9, 1:10, 1:20 or 1:30. A ratio of the on duration to the off duration may be 1:10 for pulse frequency up to 10 Hz, and a ratio of the on duration to the off duration may be 1:30 for pulse frequency higher than 10 Hz.

Where the electrical signal is applied periodically and episodically, it means that the signal is applied in a periodic manner for each episode of application.

Periodic application may also be referred to as a duty cycled application. A duty cycle represents the percentage of time that the signal is applied to the nerve for a cycle of the periodic pattern. For example, a duty cycle of 20% may represent a periodic pattern having an on duration of 2 s, and an off duration of 10 s. Alternatively, a duty cycle of 20% may represent a periodic pattern having a on duration of 1 s, and an off duration of 5 s. In other words, periodic application may also be referred to as on-off pattern stimulation, or burst stimulation.

Duty cycles suitable for the present invention are between 0.1% and 100%.

Frequency

Frequency is defined as the reciprocal of the phase duration of the electrical waveform (i.e. 1/phase).

The inventors have found preferred frequencies for stimulating a splenic arterial nerve at the application site of the invention. In particular, the inventors have found preferred frequencies for embodiments where the electrical signal is applied periodically and for embodiments where the electrical signal is applied continuously.

As previously noted, embodiments where the electrical signal is applied periodically and embodiments where the electrical signal is applied continuously provide different functions using different stimulation parameters. A continuous stimulation may be used to induce blood flow changes within the splenic vasculature that can be detected and used as on-table or peri-surgically as an indicator of successful electrode placement and/or amplitude determination; and a periodic stimulation may be used as a preferred treatment paradigm, whereby such blood flow change and/or other possible systemic effects are avoided whilst maintaining efficacy as a treatment.

In embodiments where the electrical signal is applied periodically, the electrical signal has a frequency of ≤300 Hz, preferably ≤50 Hz, more preferably ≤10 Hz. For example, the frequency of the electrical signal may be ≤50 Hz, ≤100 Hz, ≤150 Hz, ≤200 Hz, ≤250 Hz or ≤300 Hz. In other examples, the frequency of the electrical signal may be ≤10 Hz, ≤15 Hz, ≤20 Hz, ≤25 Hz, ≤30 Hz, ≤35 Hz, ≤40 Hz, ≤45 Hz, or ≤50 Hz. In further examples, the frequency may be ≤1 Hz, ≤2 Hz, ≤5 Hz, or ≤10 Hz. Additionally or alternatively, the frequency of the electrical signal may be ≥10 Hz, ≥15 Hz, ≥20 Hz, ≥25 Hz, ≥30 Hz, ≥35 Hz ≥40 Hz, ≥45 Hz, or ≥50 Hz. In other examples, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

In embodiments where the electrical signal is applied continuously, the electrical signal has a frequency of ≤50 Hz, preferably ≤10 Hz, more preferably ≤2 Hz, even more preferably ≤1 Hz. For example, the frequency may be ≤1 Hz, ≤2 Hz, ≤5 Hz, or ≤10 Hz. In other examples the frequency may be ≤0.1 Hz, ≤0.2 Hz, ≤0.3 Hz, ≤0.4 Hz ≤0.5 Hz, ≤0.6 Hz ≤0.7 Hz, ≤0.8 Hz, or ≤0.9 Hz. Additionally or alternatively, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

Where the signal waveform comprises a pulse train, the pulses are applied to the nerve at intervals according to the above-mentioned frequencies. For example, a frequency of 50 Hz results in 50 pulses being applied to the nerve per second.

Electrode and Neural Interface Design

The electrical signal is applied to a splenic arterial nerve via at least one electrode in signaling contact with the nerve at a site where the splenic artery is not in direct contact with the pancreas. The at least one electrode may be positioned on a neural interface 10.

The electrode and/or neural interface 10 may be positioned at any of the sites for applying an electrical signal previously discussed. In some embodiments, there may be a plurality of electrodes and/or neural interfaces 10, each of the plurality of electrodes and/or neural interfaces positioned at one of a plurality of sites.

In some embodiments, the electrode and/or neural interface is configured for placement around at least one splenic arterial nerve and/or around the splenic artery. In such embodiments, the neural interface may be a cuff type interface, but other interfaces which partially or fully circumvent the nerve may be used.

In other embodiments, the neural interface 10 is configured for placement on the at least one splenic arterial nerve and/or on the splenic artery. In such embodiments, the neural interface 10 may be a patch or clip type interface.

In other embodiments, the neural interface 10 is configured for placement in the splenic artery. In such embodiments, the neural interface may be a catheter or a probe type interface.

In other embodiments, the neural interface 10 is configured for placement in at least one splenic arterial nerve. In such embodiments, the neural interface may be a pin type interface.

The neural interface 10 comprises at least one electrode. The electrodes may be fabricated from, or be partially or entirely coated with, a high charge capacity material such as platinum black, iridium oxide, titanium nitride, tantalum, poly(ethylenedioxythiophene) and suitable combinations thereof.

The at least one electrode may be a flat interface electrode which is flexible, particularly in embodiments where the neural interface is configured for placement on or around the at least one splenic arterial nerve and/or the splenic artery so as to circumvent the nerve, and/or the splenic artery, when the neural interface 10 is secured on the nerve. However, other electrode types are also suitable for use in the invention. This is because applying electrical signals to splenic arterial nerves at a site where the splenic artery is not in direct contact with the pancreas provides additionally flexibility in the design of the neural interface 10, in particular the design of the at least one electrode, due to the additional space available around the splenic artery.

Other electrode types suitable for the present invention include cuff electrodes (e.g. spiral cuff, helical cuff or flat interface); hemi-cuff electrodes; a mesh, a linear rod-shaped lead, paddle-style lead or disc contact electrodes (including multi-disc contact electrodes); hook electrodes; sling electrodes; intrafascicular electrodes; glass suction electrodes; paddle electrode; and percutaneous cylindrical electrodes.

The at least one electrode may comprise a first electrode 11 and a second electrode 12, referred to herein as a bipolar electrode configuration. FIG. 1 shows a schematic diagram of an exemplary bipolar electrode configurations wherein the electrodes are placed in signaling contact with at least one splenic arterial nerve and/or splenic artery. As explained elsewhere herein, suitable signaling contact may be achieved by placing the electrodes around (i.e. partially or fully circumventing) the nerve and/or artery, on the nerve and/or the artery, or in the splenic nerve, or in the artery.

As shown in FIG. 1, the first electrode 11 and second electrode 12 are positioned along the longitudinal axis of the nerve. An electrical signal may be applied to the electrodes such that the first electrode 11 is an anode and the second electrode 12 is a cathode. Alternatively, the first electrode 11 may be cathode and the second electrode 12 an anode.

In other embodiments, the at least one electrode may comprise a first electrode, a second electrode, and a third electrode, referred to herein as a tripolar electrode configuration.

As with the bipolar configuration, the first, second and third electrodes may be positioned along the longitudinal axis of the nerve and in one example the second electrode may be positioned between the first electrode 11 and the third electrode 13.

The electrodes may be at least in part insulated from one another by a non-conductive biocompatible material. To this end, a neural interface may comprise a non-conductive biocompatible material which is spaced transversely along the nerve when the device is in use.

The inventors have found preferred electrode sizes for applying an electrical signal to at least one splenic arterial nerve at a site where the splenic artery is not in direct contact with the pancreas. The total surface area of the electrodes may be 0.1-0.3 mm$^2$. Preferably the total surface area of the electrodes is less than 0.2 cm$^2$.

In preferred electrode configurations, the width of each of the first electrode 11 and the second electrode 12 may be between 1 and 4 mm. For example, the width may be between 1 mm and 3 mm, or between 2 mm and 4 mm, or between 2 mm and 3 mm.

Controller

Referring to FIG. 1, the system of the invention 50 which may comprise a neural interface, may also comprise at least one controller, for example microprocessor 60, which is electrically coupled to the at least one electrode of the neural interface 10 and configured to control the operation of the at least one electrode. The at least one controller may be responsible for triggering the beginning and/or end of the signals delivered to the nerve by the at least one electrode. Optionally, the at least one controller may also be responsible for generating and/or controlling the signal parameters.

The at least one controller may be configured to operate in an open-loop fashion, wherein a predefined signal (as described above) is delivered to the nerve in a predefined pattern of application (also as described above) with or without an external trigger, and without any control or feedback mechanism. Alternatively, the at least one controller may be configured to operate in a closed-loop fashion, wherein a signal is applied based on a control or feedback mechanism.

The at least one controller is preferably constructed so as to generate, in use, a preconfigured and/or operator-selectable signal that is independent of any input in the system 50. The preconfigured and/or operator-selectable signal may be any one of the electrical signals previously described. In other embodiments, the at least one controller is responsive to an external signal, more preferably information (e.g. data) pertaining to one or more physiological parameters of the subject, but still within the confines of the signals previously described.

The at least one controller may be a microprocessor 60 in the system 50, suitable to be implanted in the subject.

Alternatively or additionally, the at least one controller may be a controller external to the subject.

The at least one controller may be triggered upon receipt of a signal generated by an operator, such as a physician or the subject in which the device 106 is implanted. To that end, the system 50 may additionally comprise an external system 80 comprising a controller 101. An example of such a system is described below with reference to FIG. 2.

External system 80 of wider system 100 is external the system 50 and external to the subject, and comprises controller 101. Controller 101 may be used for controlling and/or externally powering system 50. To this end, controller 101 may comprise a powering unit 102 and/or a programming unit 103. The external system 80 may further comprise a power transmission antenna 104 and a data transmission antenna 105, as further described below.

The least one controller, including microprocessor 60 and controller 101, may be a processor connected to a memory (i.e. a non-transitory computer readable storage medium) carrying an executable computer program comprising code portions which, when loaded and run on the processor, cause the processor to at least control operation of the at least one electrode. By control the operation is it meant that the at least one controller causes the at least one electrode to apply an electrical signal to the nerve using any of the signal parameters and patterns of application previously described.

Neural Stimulation System

In addition to the neural interface 10 and the at least one controller 60, the system 50 may comprise a signal generator 113 which is configured to deliver the electrical signal described above to the at least one electrode in response to a control operation from the at least one controller. The signal generator may comprise at least one current or voltage source.

The signal generator 113 may be electrically coupled to the at least one controller and to the at least one electrode. In some embodiments, at least one electrode may be coupled to the signal generator 113 via electrical leads 107. In some embodiments, the electrical leads may be coupled to the interconnectors previously described. Alternatively, the signal generator 113 may be directly integrated with the at least one electrode without leads. In any case, the system 50 may comprise a device 106, which may be implanted in the subject, and which may comprise DC current blocking output circuits (or AC current blocking output circuits), optionally based on capacitors and/or inductors, on all output channels (e.g. outputs to the at least one electrode, or physiological sensor 111).

In addition to the neural interface 10, the at least one electrode, the at least one controller, and the signal generator 113, the system 50 may comprise one or more of the following components: implantable transceiver 110; power source 112; memory 114 (otherwise referred to as a non-transitory computer-readable storage device); physiological sensor 111; and physiological data processing module 115. The physiological sensor 111 and physiological data processing module 115 are referred to herein as a detector.

The various components of the system 50 are preferably part of a single physical device, either sharing a common housing or being a physically separated collection of interconnected components connected by electrical leads, as shown in FIG. 2. As an alternative, however, the invention may use a system in which the components are physically separate, and communicate wirelessly. Thus, for instance, the at least one electrode and the implantable device (e.g. implantable device 106) can be part of a unitary device, or together may form a system (e.g. system 50). In both cases, further components may also be present to form a wider system (e.g. system 100).

For example, in some embodiments, one or more of the following components may be contained in the implantable device 106: power source 112; memory 114; and a physiological data processing module 115.

The power source 112 may comprise a current source and/or a voltage source for providing the power for the signal generator 113. The power source 112 may also provide power for the other components of the implantable device 106 and/or system 50, such as the microprocessor 60, memory 114, and implantable transceiver 110. The power source 112 may comprise a battery, the battery may be rechargeable.

It will be appreciated that the availability of power is limited in implantable devices, and the invention has been devised with this constraint in mind. Applying electrical signals to splenic arterial nerves at a site where the splenic artery is not in direct contact with the pancreas is advantageous in that it provides additionally flexibility in the design of the implantable device 106 due to the additional space available around the splenic artery. For example, the additional space may allow for a larger battery to be implanted which is capable of delivering electrical signals for a longer period of time. Moreover, the implantable device 106 and/or system 50 may be powered by inductive powering or a rechargeable power source.

Memory 114 may store power data and data pertaining to the one or more physiological parameters.

For instance, memory 114 may store data pertaining to one or more signals indicative of the one or more physiological parameters detected by detector (e.g. via physiological sensor 111, and/or the one or more corresponding physiological parameters determined via physiological data processing module 115). In addition or alternatively, memory 114 may store power data and data pertaining to the one or more physiological parameters from external system 80 via the implantable transceiver 110. To this end, the implantable transceiver 110 may form part of a communication subsystem of the wider system 100, as is further discussed below.

Physiological data processing module 115 is configured to process one or more signals indicative of one or more physiological parameters detected by the physiological sensor 111, to determine one or more corresponding physiological parameters. Physiological data processing module 115 may be configured for reducing the size of the data pertaining to the one or more physiological parameters for storing in memory 114 and/or for transmitting to the external system via implantable transceiver 110.

Implantable transceiver 110 may comprise an one or more antenna(e). The implantable transceiver 100 may use any suitable signaling process such as RF, wireless, infrared and so on, for transmitting signals outside of the body, for instance to wider system 100 of which the system 50 is one part.

Alternatively or additionally, physiological data processing module 115 may be configured to process the signals indicative of the one or more physiological parameters and/or process the determined one or more physiological parameters to determine the evolution of the disease in the subject. In such case, the system 50, in particular the implantable device 106, will include a capability of calibrating and tuning the signal parameters based on the one or more physiological parameters of the subject and the determined evolution of the disease in the subject.

The physiological data processing module 115 and the at least one physiological sensor 111 may form a physiological sensor subsystem, also known herein as a detector, either as part of the system 50, part of the implantable device 106, or external to the system.

There may be at least one detector configured to detect one or more physiological parameters relating to the treatment of an inflammatory disorder. For example, reduction in pro-inflammatory cytokines and chemokines, an increase in anti-inflammatory cytokines (e.g. IL-10) and/or resolving mediators (such as resolvins, lipoxins, eicosanoids, maresins and protectins), an increase in catecholamines and acetylcholine, changes in haematology and cell counts; such as changes in immune cell population or immune cell surface co-stimulatory molecules, a reduction in factors involved in the inflammation cascade, and/or a reduction in immune response mediators, as is further discussed below. For example, the detector may be configured for detecting biomolecule concentration using electrical, RF or optical (visible, infrared) biochemical sensors.

There may be at least one detector configured to detect other physiological parameters such as blood flow rate in the spleen, blood flow rate in the splenic artery, blood flow rate in the splenic vein, spleen volume, neural activity in at least one splenic arterial nerve, or impedance of the at least one electrode.

For example, the detector may be configured for detecting blood flow using intra- or perivascular flow tubes in or around the artery or vein. Alternatively, detector may detect splenic artery contraction and blood flow changes using electrical impedance tomography, electrical impedance, stimulator voltage compliance, Doppler flow, splenic tissue perfusion, ultrasound, strain measurement, or pressure.

In other examples, the detector may be configured for detecting neural activity of at least one splenic arterial nerve using an electrical sensor. When the detector is configured for detecting neural activity of a single splenic arterial nerve, the detector may detect action potentials. When the detector is configured for detecting neural activity of a plurality of splenic arterial nerve, the detector may detect compound action potentials.

In further examples, the detector may be configured for detecting spleen volume using ultrasound.

In other examples, the detector may be configured to detect impedance of the at least one electrode using an impedance meter, preferably a low-current AC (e.g. 1 kHz) impedance meter. In particular, the detector may detect impedance between the at least one electrode and ground, and/or between pairs of electrodes of the at least one electrodes (where there is a plurality of electrodes). In such examples, the at least one electrode is suitable for placement on or around the nerve.

In other examples, the detector may be configured for detecting the subject's movement using an accelerometer. The accelerometer determines when the subject is asleep by determining if the subject is lying down, i.e. if there has been an extended period (e.g. ≥70 min) in which the subject has maintained a substantially lying down position. This determination is based on the orientation and acceleration of experienced and measured by the accelerometer. The physiological parameters determined by the detector may be used to trigger the microprocessor 60 to deliver a signal of the kinds described above to the nerve using the at least one electrode. Upon receipt of the signal indicative of a physiological parameter received from physiological sensor 111, the physiological data processor 115 may determine the physiological parameter of the subject, and the evolution of the disease, by calculating in accordance with techniques known in the art. For instance, if a signal indicative of excessive cytokine (e.g. TNF) concentration in the circulation is detected, the processor may trigger delivery of a signal which dampens secretion of the respective signaling molecule, as described elsewhere herein.

The memory 114 may store physiological data pertaining to normal levels of the one or more physiological parameters. The data may be specific to the subject into which the system 50 is implanted, and gleaned from various tests known in the art. Upon receipt of the signal indicative of a physiological parameter received from physiological sensor 111, or else periodically or upon demand from physiological sensor 111, the physiological data processor 115 may compare the physiological parameter determined from the signal received from physiological sensor 111 with the data pertaining to a normal level of the physiological parameter stored in the memory 114, and determine whether the received signals are indicative of insufficient or excessive of a particular physiological parameter, and thus indicative of the evolution of the disease in the subject.

The system 50 and/or implantable device 106 may be configured such that if and when an insufficient or excessive level of a physiological parameter is determined by physiological data processor 115, the physiological data processor 115 triggers delivery of a signal to the nerve by the at least one electrode, in the manner described elsewhere herein. For instance, if physiological parameter indicative of worsening of any of the physiological parameters and/or of the disease is determined, the physiological data processor 115 may trigger delivery of a signal which dampens secretion of the respective biochemical, as described elsewhere herein. Particular physiological parameters relevant to the present invention are described above. When one or more signals indicative of one or more of these physiological parameters are received by the physiological data processor 115, a signal may be applied to the nerve via the at least one electrode.

In some embodiments, controller 101 may be configured to make adjustments to the operation of the system 50. For instance, it may transmit, via a communication subsystems (discussed further below), physiological parameter data pertaining to a normal level of signaling molecules secreted from the spleen. The data may be specific to the subject into which the device is implanted. The controller 101 may also be configured to make adjustments to the operation of the power source 112, signal generator 113 and processing elements 60, 115 and/or electrodes in order to tune the signal delivered to the nerve by the neural interface 10.

As an alternative to, or in addition to, the ability of the system 50 and/or implantable device 106 to respond to physiological parameters of the subject, the microprocessor 60 may be triggered upon receipt of a signal generated by an operator (e.g. a physician or the subject in which the system 50 is implanted). To that end, the system 50 may be part of a wider system 100 which comprises external system 80 and controller 101, as is further described below.

Beyond the Neural Stimulation System

The neural stimulation system 50 may be part of a wider system 100 that includes a number of subsystems, for example the external system 80, see FIG. 2. The external system 80 may be used for powering and programming the neural stimulation system 50 through human skin and underlying tissues.

The external subsystem 80 may comprise, in addition to controller 101, one or more of: a powering unit 102, for wirelessly recharging the battery of power source 112 used to power the implantable device 106; and, a programming unit 103 configured to communicate with the implantable transceiver 110. The programming unit 103 and the implantable transceiver 110 may form a communication subsystem. In some embodiments, powering unit 102 is housed together with programming unit 103. In other embodiments, they can be housed in separate devices.

The external subsystem 80 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in system 50 for data reception and transmission from/to the external system 80. If more than one antenna is used in the system 50, these antennae are rotated 30 degrees from one another to achieve a better degree of power transfer efficiency during slight misalignment with the with power transmission antenna 104.

External system 80 may comprise one or more external body-worn physiological sensors 121 (not shown) to detect signals indicative of one or more physiological parameters. The signals may be transmitted to the system 50 via the at least one antennae of implantable transceiver 110. Alternatively or additionally, the signals may be transmitted to the external system 50 and then to the system 50 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the system 50 in a closed-loop fashion. The physiological parameters of the subject determined via signals received from the external sensor 121 may be used in addition to alternatively to the physiological parameters determined via signals received from the implanted physiological sensor 111.

For example, in a particular embodiment a detector external to the implantable device may include a non-invasive blood flow monitor, such as an ultrasonic flowmeter and/or a non-invasive blood pressure monitor, and determining changes in physiological parameters, in particular the physiological parameters described above. As explained above, in response to the determination of one or more of these physiological parameters, the detector may trigger delivery of signal to a splenic arterial nerve by the at least one electrode, or may modify the parameters of the signal being delivered or a signal to be delivered to the nerve by the at least one electrode in the future.

The system 100 may include a safety protection feature that discontinues the electrical stimulation of the nerve in the following exemplary events: abnormal operation of the system 50 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the system 50, or internally within the system 50.

The external system 80 may comprise an actuator 120 (not shown) which, upon being pressed by an operator (e.g.

a physician or the subject), will deliver a signal, via controller 101 and the respective communication subsystem, to trigger the microprocessor 60 of the system 50 to deliver a signal to the nerve by the at least one electrode.

The external system 80 may comprise a display 109 for the microcontroller 60 or the controller 101 to alert the operator (e.g. a physician or the subject) to a state of the system or of the subject. The display 109 may be a monitor such as an LED monitor, or may be a visual indicator such as an LED.

System 100 of the invention, including the external system 80, but in particular system 50, is preferably made from, or coated with, a biostable and biocompatible material. This means that the system is both protected from damage due to exposure to the body's tissues and also minimizes the risk that the system elicits an unfavorable reaction by the host (which could ultimately lead to rejection). The material used to make or coat the system should ideally resist the formation of biofilms. Suitable materials include, but are not limited to, poly(3,4-ethylenedioxythiophene):p-toluene-sulfonate (PEDOT:PTS or PEDT), poly(p-xylylene) polymers (known as Parylenes) and polytetrafluoroethylene.

The implantable device 106 of the invention will generally weigh less than 50 g.

Determining Correct Placement of the Neural Interface

The invention also provides a method for determining whether a neural interface 10 is correctly placed in signaling contact with a splenic arterial nerve. The method comprises the following steps:

A. providing a system of the invention;

B. positioning an electrode and/or a neural interface in signaling contact with the nerve at a site where the splenic artery is not in direct contact with the pancreas;

C. controlling the operation of the least one electrode with at least one controller to apply an electrical signal to the nerve;

D. determining that a change in blood flow rate in the spleen, splenic artery, splenic vein, a decrease in spleen volume, a decrease in spleen perfusion, a change in systemic arterial blood pressure and heart rate, a decrease in electrical impedance or voltage compliance, an increase in neural activity in the nerve, or a change in impedance of the at least one electrode has been detected E. indicating to an operator that the neural interface had been placed correctly in signaling contact with the nerve.

Referring to step A of the method, the system of the invention provided must comprise a neural interface with at least one electrode, at least one controller, and at least one detector. Any other feature of the system described herein may also be provided.

In step B, the electrode and/or neural interface is preferably positioned in signaling contact with the nerve. In some embodiments of the method, step B may be omitted. For instance, step B may be omitted when determining whether an electrode and/or neural interface which was previously implanted has moved over time.

In step C, the at least one controller controls the operation of the at least one electrode to apply the electrical signal to the nerve. The electrical signal may be similar to an electrical signal used to stimulate neural activity described above in that it may have the same waveform, and also apply the same charge density per phase to the nerve. However, the overall charge applied to the nerve is preferably higher. This can be achieved by using continuous signal application instead of periodic signal application, and/or by using a higher frequency than the frequencies described for continuous signal application above.

In particular, the signal may be applied continuously with a frequency of the rate previously described for periodic signal application. Thus, the electrical signal may have a frequency of ≤300 Hz, preferably ≤50 Hz, more preferably ≤10 Hz. For example, a continuous stimulation ≤10 Hz may be used for efficacy and/or treatment; and/or a continuous stimulation ≤30 Hz and ≥5 Hz may be used for blood flow detection; and/or a periodic stimulation ≥10 Hz may be used for efficacy and/or treatment. For example, the frequency of the electrical signal may be ≤50 Hz, ≤100 Hz, ≤150 Hz, ≤200 Hz, ≤250 Hz or ≤300 Hz. In other examples, the frequency of the electrical signal may be ≤10 Hz, ≤15 Hz, ≤20 Hz, ≤25 Hz, ≤30 Hz, ≤35 Hz, ≤40 Hz, ≤45 Hz, or ≤50 Hz. In further examples, the frequency may be ≤1 Hz, ≤2 Hz, ≤5 Hz, or ≤10 Hz. Additionally or alternatively, the frequency of the electrical signal may be ≥10 Hz, ≥15 Hz, ≥20 Hz, ≥25 Hz, ≥30 Hz, ≥35 Hz ≥40 Hz, ≥45 Hz, or ≥50 Hz. In other examples, the frequency of the electrical signal may be ≥0.1 Hz, ≥0.2 Hz, ≥0.5 Hz, ≥1 Hz, ≥2 Hz, or ≥5 Hz. Any combination of the upper and lower limits above is also possible.

The electrical signal may be applied continuously for one of the application episodes previously described (e.g. 400 to 600 pulses). Alternatively, the electrical signal may be applied continuously for an episode defined by a set duration. Preferably the set duration for applying the electrical signal is ≤3 hours. For example, the set duration may be ≤1 min, ≤2 min, ≤5 min, ≤10 min, ≤20 min, ≤30 min, ≤1 h, ≤2 h, or ≤3 h. Additionally or alternatively, the set duration may be ≥1 min, ≥2 min, ≥5 min, ≥10 min, ≥20 min, ≥30 min, ≥1 h, or ≥2 h. Any combination of the upper and lower limits above is also possible.

In step D, the at least one detector may detect one or more of: blood flow rate in the spleen, blood flow rate in the splenic artery, blood flow rate in the splenic vein, spleen volume, neural activity in the nerve, or impedance of the at least one electrode. Suitable detectors for detecting these physiological parameters are described above.

When the detector is configured to detect blood flow rate in the spleen, blood flow rate in the splenic artery, and/or blood flow rate in the splenic vein, the electrode and/or neural interface may be determined to be placed in signaling contact with the nerve correctly when the detected blood flow is different than baseline blood flow.

When the detector is configured to detect neural activity in the nerve, the electrode and/or neural interface may be determined to be placed in signaling contact with the nerve correctly when the detected neural activity is higher than baseline neural activity.

When the detector is configured to detect spleen volume, the electrode and/or neural interface may be determined to be placed in signaling contact with the nerve correctly when the detected spleen volume is lower than baseline spleen volume. In other words, when the spleen has contracted.

When the detector is configured to detect impedance of the at least one electrode, the electrode and/or neural interface may be determined to be placed in signaling contact with the nerve correctly when the detected impedance is different from baseline impedance. The detected impedance is an impedance between a first electrode and a second electrode of the at least one electrode measured whilst applying the signal to the nerve. "Baseline impedance", is the impedance between the first electrode and the second electrode before applying the signal to the nerve.

According to step E, once the at least one controller has established that the electrode and/or neural interface has been placed correctly on the nerve, the at least one controller indicates this to an operator.

Indication to an operator may take the form of a notice on a display 109 of the system, a blinking LED, or the like.

If the detector determines that the electrode and/or neural interface is not placed correctly in signaling contact with the nerve correctly, the at least one controller may indicate to an operator, via the display 109, that the neural interface is not correctly placed in signaling contact with the nerve.

If the neural interface has not been placed correctly, then steps B to E can be repeated until the neural interface is correctly placed in signaling contact with the nerve.

Steps C, D and E of the method may be executable by the at least one controller. The at least one controller comprises a processor connected to a memory (i.e. a non-transitory computer readable storage medium) carrying an executable computer program comprising code portions which, when loaded and run on the processor, cause the processor to perform steps C, D and E.

The method for determining placement of the neural interface may also be used to follow up the success of a system of the invention (i.e. one which is implanted in the subject) post operatively through the patient's lifetime (for example using external transcutaneous splenic blood flow measurement or systemic arterial blood pressure as a marker of successful nerve-electrode intercation). Thus, in addition to way of ensuring correct placement, the method provides a way to determine suitable efficacy (in cases where cytokine readouts will not be possible).

General

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Unless otherwise indicated each embodiment as described herein may be combined with another embodiment as described herein. The term "comprising" encompasses "including" as well as "consisting" e.g. a composition "comprising" X may consist exclusively of X or may include something additional e.g. X+Y.

It will be understood that the benefits and advantages described above may relate to one embodiment or may relate to several embodiments. The embodiments are not limited to those that solve any or all of the stated problems or those that have any or all of the stated benefits and advantages.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

BRIEF DESCRIPTION OF DRAWINGS

Embodiments of the invention will be described, by way of example, with reference to the following drawings, in which:

FIGS. 3A-E show histological and electrophysiological characterization of a pig splenic nerve. FIG. 3A is a photomicrograph of a semi-thin section (0.5 μm thickness) of the SpA (splenic artery)/SpN (splenic arterial nerve) stained with Toluidine blue. No myelinated axons can be observed in the image. FIG. 3B representative traces of evoked compound action potential (eCAP) recorded from fascicles of the peri-arterial splenic nerve dissected off the artery when stimulating at 1 Hz with a peri-arterial cuff (around the entire SpN plexus) or with a small cuff around few fascicles of the SpN bundle. The traces are the average of 10 responses. FIG. 3C shows the range of conduction velocities of the different components of the eCAP. FIGS. 3D and 3E show the strength-duration curve of the SpN obtained by stimulating the whole plexus (FIG. 3D) or few dissected fascicles (FIG. 3E). The graphs show also the relative charge density to obtain threshold eCAP at different stimulation amplitudes. All stimulations were performed at 1 Hz to limit stimulation-induced action potential conduction slowing in the nerve.

4E shows the mean (n=3) change in sMABP and HR (from −30 to +180 s, relative to start of stimulation) during a 1-minute stimulation (symmetric biphasic pulses, 400 µs PW at 10 Hz) of the SpN plexus at different current amplitudes (between 3.5 and 20 mA).

FIG. 5A shows the mean (n=3) change in mSpA BF (from −30 to +180 s, relative to stimulation) during a 1 minute stimulation (symmetric biphasic pulses, 400 µs PW at about 36.9 µC/cm$^2$/phase) of the SpN plexus at different frequencies (between 0.25 and 100 Hz). In FIG. 5C to 5D, the graphs show the changes in mSpV BF, sMABP, HR (expressed as % over prestimulation baseline) during a 1 minute stimulation (symmetric biphasic pulses, 400 µs PW at about 36.9 µC/cm$^2$/phase) of the SpN plexus at different frequencies (between 0.25 and 100 Hz). Data in FIG. 5A is expressed as mean±s.d. In FIGS. 5A and 5C to 5D, the box represents the stimulation time window.

FIG. 6 shows a representative experimental recording of local and systemic changes associated with the stimulation of few SpN fascicles dissected off the artery with different frequencies. HR, sMABP, Stimulation input, eCAP, SpA BF raw and mSpA BF data are shown from a representative experiment where frequency ranges from 3 to 300 Hz.

FIGS. 8B(I)-(III) shows the eCAP recorded from the SpN during a 1 minute stimulation delivered at 10 Hz in burst of 5 or 10 pulses separated by an off period of 5 or 10 s. Each image show the superimposition of all the evoked responses. Note that the responses neither shift to the right nor are reduced in amplitude over time. FIG. 8C shows the quantification of the area under the curve (AUC) of each recorded eCAP of the different stimulation paradigms. In particular, FIG. 8C shows the comparison of the values between 1 and 60 pulses delivered with the different paradigms. FIG. 8D shows eCAP latency (expressed as % over the latency of the first response) over 600 consecutive pulses with the different patterns of stimulations shown in FIGS. 8A-C. Data are shown as mean (N≥3). Dotted lines represent the 95% confidence interval. FIG. 8E shows eCAP amplitude (expressed as % over the amplitude of the first response) over 600 consecutive pulses with the different pattern of stimulations shown in FIGS. 8A-C. Data are shown as mean (N≥3). Least squares regression curves were fitted against the latency (as shown in FIG. 8D) and amplitude data (as shown in FIG. 8E). Dotted lines represent the 95% confidence interval.

FIG. 9 shows the maximum change in mSpA BF expressed as % over the change obtained during a 60 s stimulation with biphasic, symmetric pulses delivered at 10 Hz (in black). Different stimulation paradigms, delivered with the same current amplitude, are compared: continuous 10 Hz, continuous 1 Hz and burst stimulation (5 pulses at 10 Hz every 5 s) with either symmetric or asymmetric biphasic pulses.

FIG. 13A shows the anatomical distance from the coeliac trunk (Origin SA), to the imaginary sagittal plane and distances from the Origin SA to the various branching pancreatic arteries (PA). Boxes indicate the sites of resected tissue. The length of the splenic arterial loop is also shown. The site of the pancreas, spleen and stomach in relation to the splenic artery are also depicted. FIG. 13B shows the diameter of the splenic artery measured from each resected tissue sample. FIG. 13C shows the overview shows the spleen, the pancreas, splenic artery (SA), and surrounding adipose and connective tissue of cadaver III. The SA presents three loops, with a minimum height of 1.0 cm from the inner curvature of the loop to the pancreas. The characteristics can be found in table FIGS. 14A-B show splenic arterial nerve stimulation before the onset of disease reduces disease activity in mice with collagen-induced arthritis. Animals were divided over 3 groups; sham N=8, Sim 24H N=7, Stim 4H N=7. Clinical scores are shown in FIG. 14A. The incidence is shown in FIG. 14B. CIA was induced at day 0 with CII/CFA, on day 11 the cuffs were implanted on day 21 the animals received a boost with CII/IFA. Stimulation was performed 1× a day ((STIM 24H), or 6× a day (STIM 4H). After day 45, stimulation was stopped and animals were follow-up up to day 80.

FIG. 15 shows splenic nerve stimulation after the onset of disease reduces the clinical score in mice with collagen-induced arthritis. CIA was induced at day 0 with CII/CFA, on day 11 the cuffs were implanted and on day 28 stimulation was started. Animals were divided over 2 groups; sham N=5, Stim 4 h N=5). On day 21 the animals received a boost with CII/IFA. Animals were follow-up up to day 55 after start of stimulation (day 80 after induction of CIA). One animal was excluded on day 44 due to a broken wire.

FIG. 16A shows human splenic neurovascular bundle (NVB) containing the SpA, the SpN, connective tissue, sections of pancreas and lymph nodes freshly isolated from a donor. Two small cuff electrodes (650 μm in diameter) were placed on a select few dissected fascicles. The schematic of the preparation indicates the position (a and b) of the stimulating and recording cuffs. The dotted lines indicate the areas in which the sections shown in B and C were taken. FIG. 16H shows charge densities required to stimulate the SpN of the three different species at different PW. The data was fitted with linear regressions. Scale bars: FIG. 16B=2 mm; FIG. 16C=100 μm.

FIG. 18 shows (Left) Fascicle diameter, (Right) Fascicle spread around adventitia (outer splenic arterial wall) for proximal, middle and distal parts of the splenic neurovascular bundle (NVB), and (Middle) Percentage of fascicles vs distance from adventitia.

FIG. 19A shows a population recruitment curve for in-vivo data from porcine splenic neurovascular bundle stimulation.

MODES FOR CARRYING OUT THE INVENTION

Figure 1:
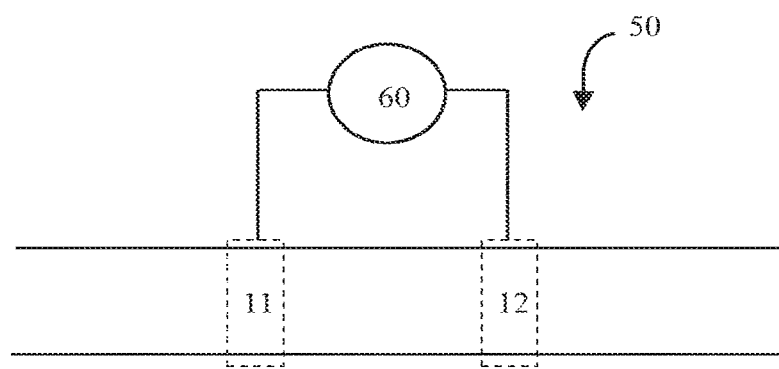
FIG. 1 illustrates a neural stimulation system.
Figure 2:
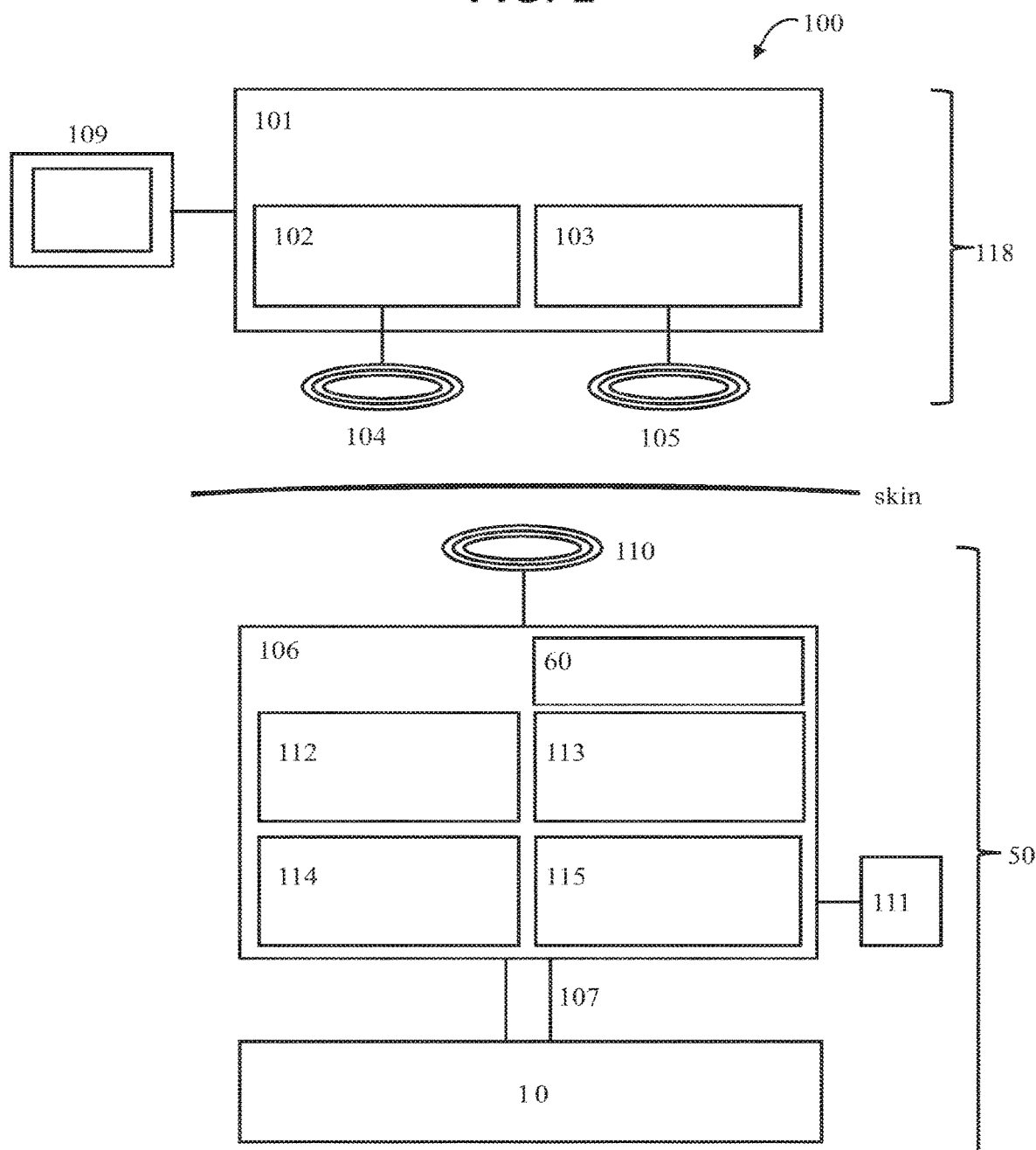
FIG. 2 illustrates a wider system including the neural stimulation system.
Figure 3A:
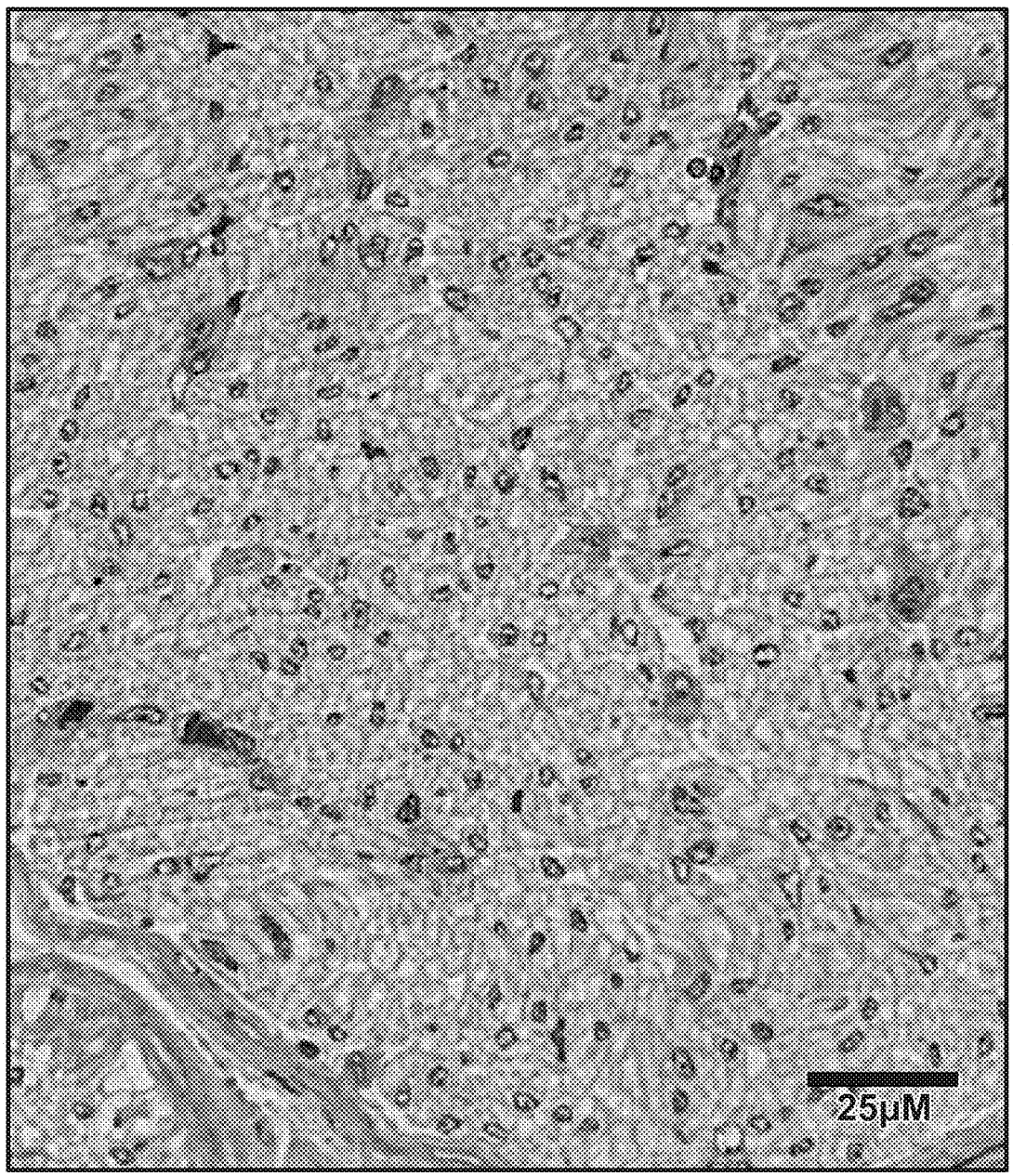
Figure 3D:
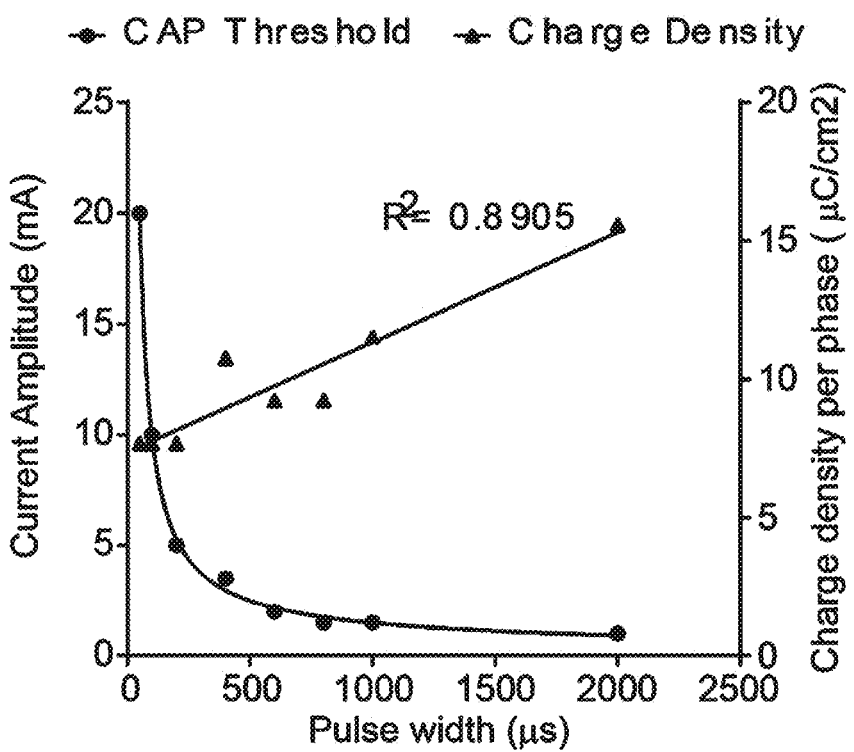
Figure 3E:
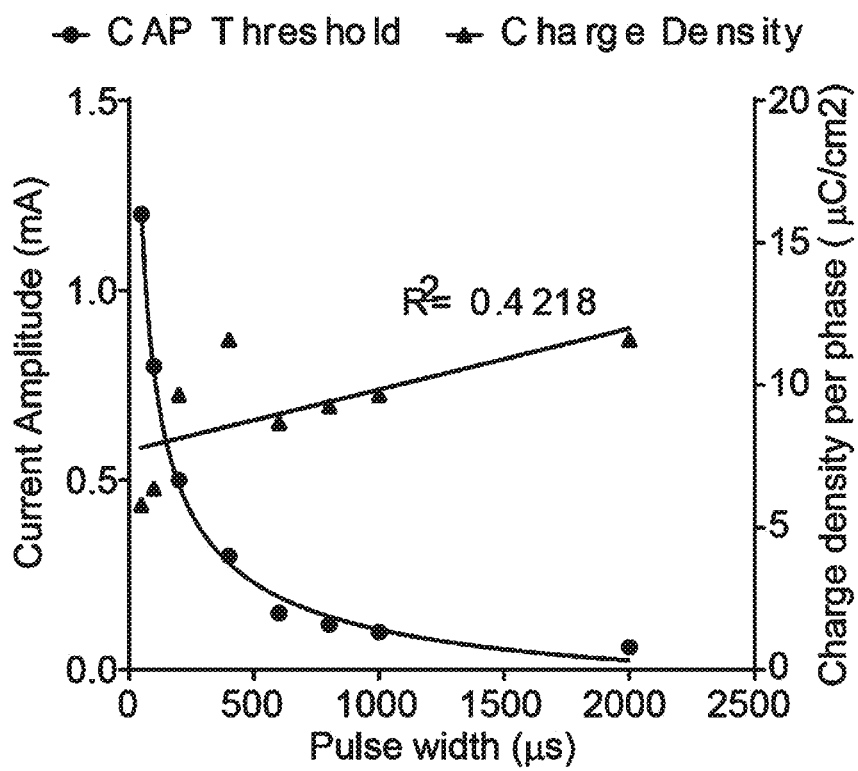

Electrical Stimulation of the Splenic Arterial Nerve in Pig (Study 1)

Materials and Methods

A total of 8 pigs (body weight between 40-50 Kg) were used for the histological and electrophysiological characterization of the splenic nerve.

On the experimental day, the animal was sedated with ketamine (1.5 mg/kg) and midazolam (0.5 mg/kg) administered by intramuscular injection. An intravenous catheter was placed in one auricular vein, and anesthesia was induced by propofol (2 mg/Kg) administered intravenously. An endotracheal tube was placed, and anesthesia was maintained with sevoflurane inhalant combined with continuous rate infusion (CRI) of fentanyl (0.2 μg/Kg/min).

After induction of general anesthesia, the animal was positioned in dorsal recumbency for placement of bilateral indwelling jugular vein catheters and one femoral arterial catheter under ultrasonographic guidance. Animals undergoing splenic arterial nerve (SpN) cuff implantation were then repositioned into right lateral recumbency.

The surgical approach to SpN cuff implantation was as follows. The thoracolumbar junction was supported and slightly elevated using a sand bag. After appropriate surgical preparation (clipping and aseptic scrub with chlorhexidine gluconate and alcohol), the left flank was aseptically draped exposing a 20×25 cm area centered on the second to last rib. A 15 cm skin incision was made in the second to last intercostal space using monopolar electrocautery. The incision was continued through the subcutaneous tissues and intercostal musculature until the peritoneum was exposed. Two Finochietto rib retractors were placed retroperitoneal, taking care to engage the ribs. Over the next few minutes, the retractors were gradually opened, resulting in exposure of the left lateral abdomen measuring approximately 10×8 cm. The retractor blades were covered with gauze sponges soaked in carboxymethyl cellulose (CMC). The peritoneum was longitudinally incised and sutured to the skin (Vicryl 2-0; Ford interlocking suture pattern) covering the retractors blades in order to minimize risk of splenic tears during handling. Using careful digital manipulation, the spleen was exteriorized and the splenic artery (SpA) was identified along its visceral surface. At the mid portion of the spleen, proximal to the SpA branching into the left gastroepiploic artery, a short segment of the SpA was carefully dissected free of surrounding soft tissue for placement of a 1 mm ultrasonic flow probe (Transonic). After probe placement, the spleen was repositioned into the abdomen.

By slight rotation of the splenic visceral base towards the operator, and placing gentle ventral traction on the spleen, the gastrosplenic ligament at the splenic hilum was incised using Metzembaum scissors, exposing the SpA. The artery was followed in a dorsal direction to its origin (i.e. the bifurcation of the celiac artery into the left gastric artery (LGA) and the SpA). Immediately distal to this bifurcation, an approximately 1 cm segment of the SpA with the peri-arterial SpN network intact, was circumferentially isolated by blunt dissection using Metzenbaum scissors. A curved Mixter artery forceps was inserted under the artery from caudal to cranial, grasping one flap of the 2.5 mm diameter CorTec cuff introduced into the surgical field using straight Microdissection forceps. The cuff was placed around the SpA and the intact peri-arterial SpN network by reversing the motion of the Mixter forceps, taking care to appose the two flaps of the cuff when properly placed. The tension on the spleen and artery was then released. SpA blood flow readings were tested and finally the rib retractors were partially closed and the exposed incision covered with saline-soaked gauze sponges.

Electrophysiological experiments generally entailed dissecting and cuffing (using a 500 μm diameter bipolar or tripolar CorTec cuff) one or several discrete SpN fascicles few centimeters distal (closer to the spleen) to the stimulating cuff to enable evoked compound action potential (eCAP) recording during stimulation of the whole SpN plexus or of few fascicles (see FIGS. 3A-E). Also, different combinations of blocking neural signaling (e.g. using topical administration of local anesthesia, or transection of the SpN fascicle) either upstream or downstream of the stimulation site were performed.

Recorded eCAP were amplified and filtered (100-1000 Hz) using an 1800 2-Channel Microelectrode AC Amplifier (A-M system). Nerve activity was monitored continuously using an oscilloscope and recorded to a computer using a 16 channels PowerLab (AD Instruments) acquisition system and LabChart 8 software using a sampling rate of 20 kHz. eCAP were generally averaged (8-10 pulses) and peak to peak or area under the curve (AUC) of the averaged response quantified. The conduction velocity of the eCAP components of the SpN were calculated from the distance between stimulation and recording site and the latency of the eCAP signal.

Electrocardiogram (ECG), Heart rate (HR), arterial blood pressure, respiratory rate (RR), pulse oximetry, capnography, spirometry were monitored throughout the surgery. Body temperature was recorded continuously with an intra-nasal probe. Arterial blood gasses were analyzed throughout the experiment to monitor pH, Glucose, pO2 and pCO2, K+ levels. All physiological parameters as well as the level of used sevoflurane were recorded (every 5-10 minutes) on the record sheet. Physiological data were also digitalized using Powerlab acquisition system and LabChart software. All parameters were generally sampled at a frequency between 0.1 and 2 kHz.

The depth of anesthesia was assessed by palpebral reflex, corneal reflex, medioventral eye ball position, and jaw tone.

Moreover, physiological parameters as well as a bispectral index monitoring system (levels between 30 and 60) were used to adjust anesthetic levels. In some cases, boluses of propofol were used.

In some cases intra-operative ultrasonography of the spleen was used for real-time monitoring of SpA blood flow changes during SpN stimulation. For this procedure, an intra-operative probe (i12L-RS linear intraoperative transducer 4-10 MHz, 29×10 mm footprint, 25 mm field of view; GE Vivid-i) was used.

SpA blood flow changes was assessed by color Doppler and continuous wave spectral tracing. After color Doppler identification of the SpA within the splenic parenchyma 2-3 cm distal to the splenic hilum, continuous wave spectral tracing of the SpA flow was obtained by directing the windowing cursors to the center of the SpA lumen. After obtaining a representative signal, the ultrasonography probe and cursor window was left in position while SpN stimulation commenced.

All statistical analyses were performed with commercially available statistical software (JMP Pro 13.0.0 or GraphPad Prism 5.0).

Results

Recording of the eCAP generated during SpN stimulation, either of the whole SpN plexus with the peri-arterial cuff, or stimulation of few fascicles with a smaller cuff, generated an eCAP with a specific latency dependent on the distance between stimulating and recording sites (FIG. 3B). The range of conduction velocities of the different components of the eCAP is shown in FIG. 3C. The stimulation of either the whole plexus or few fascicles generated an eCAP with an average speed below 1 m/s (FIG. 3C). This conduction velocity is in line with histology findings in the characterization data below that describe the SpN being an unmyelinated nerve. The relationship between current amplitude and pulse duration necessary to elicit an eCAP either stimulating the whole plexus or few fascicles in shown in FIGS. 3D and 3E (respectively). When stimulating the whole plexus with a peri-arterial cuff the threshold of the nerve response was found between 7.692 and 15.58 $\mu C/cm^2$/phase. When stimulating few dissected fascicles with a smaller cuff the threshold was found to be between 5.796 and 11.594 $\mu C/cm^2$/phase. In both cases the threshold value of current density for eCAP recording was lower at shorter pulse width (PW).

Figure 4B:
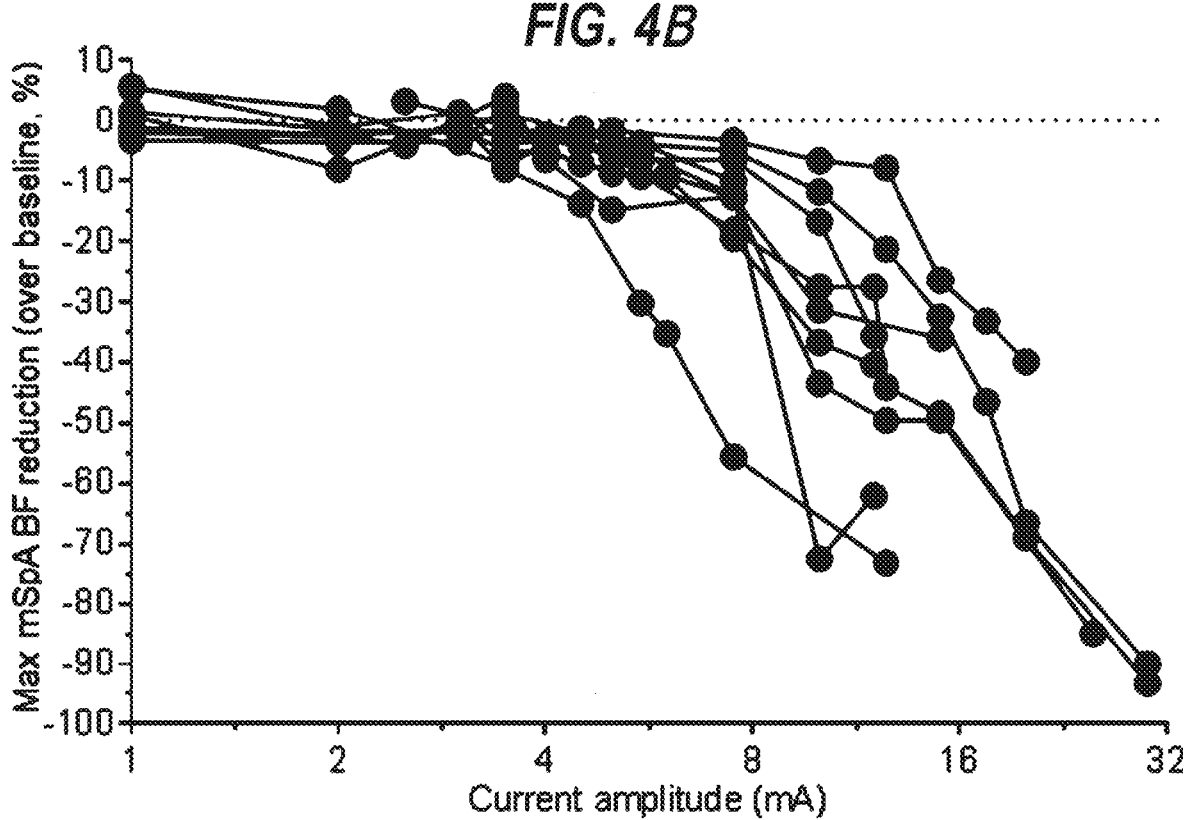
FIG. 4B shows the maximum reduction in mSpA BF reached during a 1 minute stimulation (symmetric square biphasic pulses, 400 μs PW at 10 Hz) of the SpN plexus at different current amplitudes. Each line represent an animal tested.
Figure 4C:
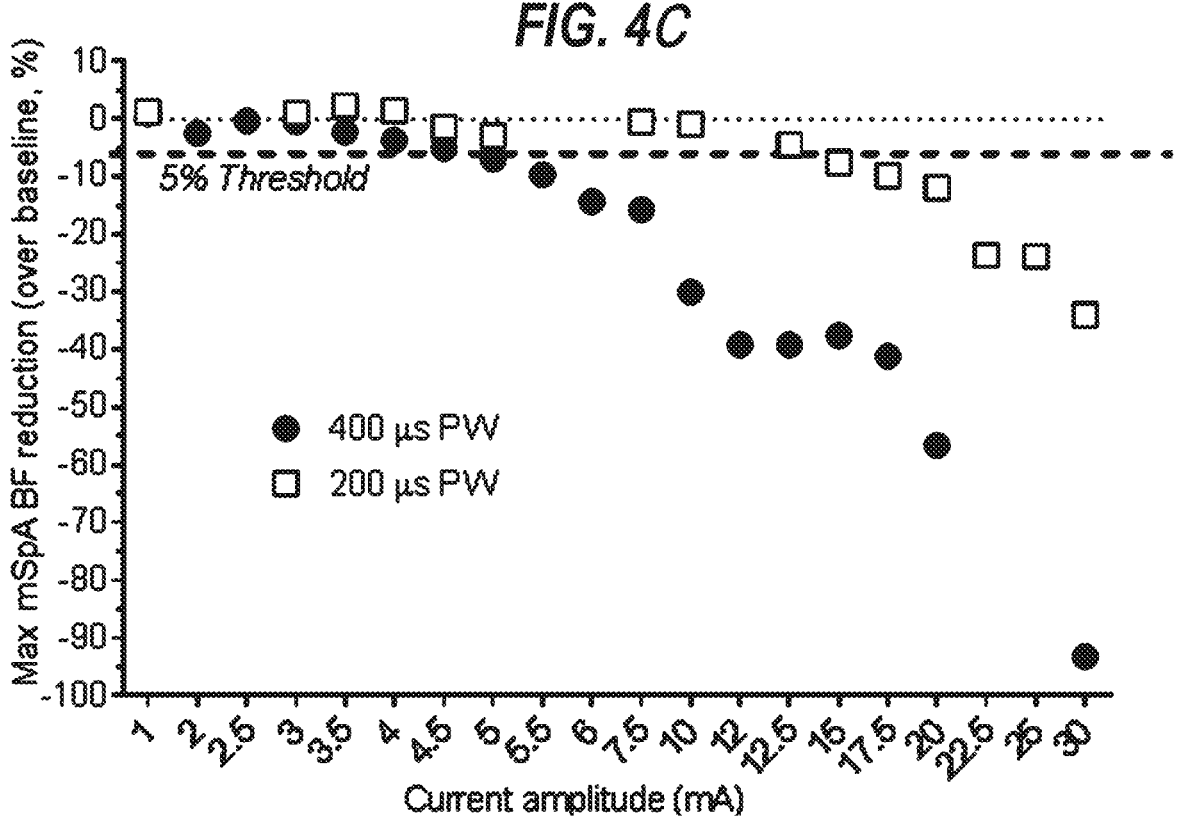
FIG. 4C shows the mean (n≥3) maximum reduction in mSpA BF reached during a 1-minute stimulation (symmetric biphasic pulses, 400 μs or 200 μs PW at 10 Hz) of the SpN plexus at different current amplitudes and with two different PW: 400 (black circles) and 200 (black squares) μs.

SpN biphasic stimulation for 1 minute at 10 Hz and 400 μs PW above a specific current threshold consistently caused transient blood flow reduction within the distal SpA as measured via a perivascular flow probe. There was a clear dose-response relationship between delivered current and flow reduction: the higher the amplitude the stronger was the observed reduction in blood flow (FIG. 4A). The blood flow change threshold, defined as a 5% change in mean SpA blood flow (mSpA BF) compared to pre-stimulation baseline, was observed around 4.5 mA (with a 400 μs PW) and around 12 mA (with 200 μs pulse width) (FIGS. 10B and 10C). When calculating the charge density per phase of the threshold to cause blood flow changes the value was very similar: about 13.8 $\mu C/cm^2$/phase at 400 μs and 18.46 $\mu C/cm^2$/phase at 200 μs. Stimulation with 12 mA and 400 μs PW (36.9 $\mu C/cm^2$/phase) caused a mean maximum BF reduction in the SpA of about 40% from baseline values.

Figure 4E:
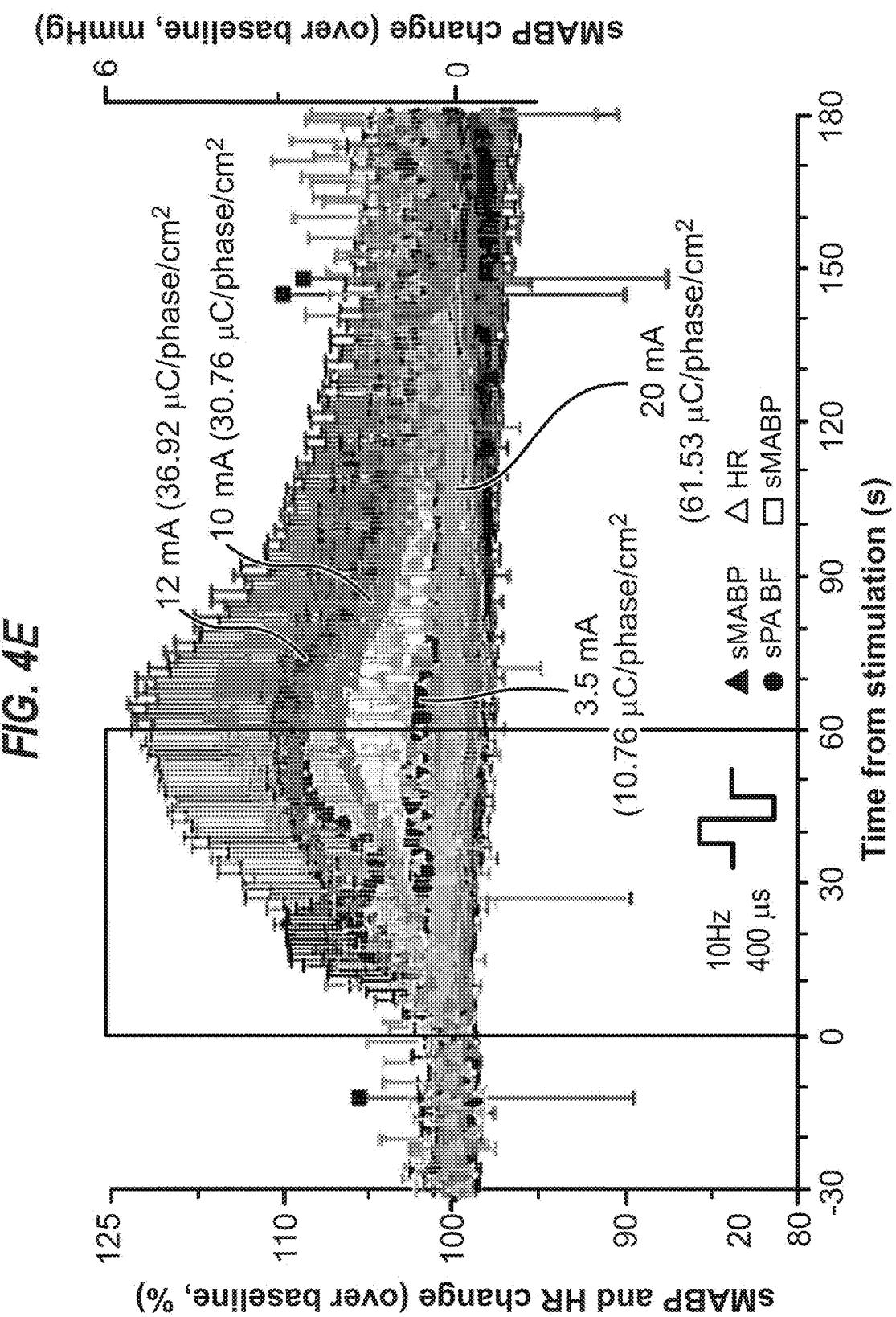
FIG. 4A shows the mean (n=8) change in mSpA BF (from −30 to +180 s, relative to start of stimulation) during a 1 minute stimulation (symmetric square biphasic pulses, 400 μs PW at 10 Hz) of the SpN plexus at different current amplitudes (between 3.5 and 20 mA).
FIG. 4D shows the change in mSpV BF (from −30 to +180 s, relative to start of stimulation) during a 1-minute stimulation (symmetric biphasic pulses, 400 μs PW at 10 Hz) of the SpN plexus at different current amplitudes (between 3.5 and 12 mA). FIG.
FIGS. 4F and 4G summarize the mean (n=3) maximum changes in mSpA BF, sMABP, HR and RR during a 1-minute stimulation (symmetric biphasic pulses, 400 µs PW at 10 Hz) of the SpN plexus (FIG. 4F) or some dissected SpN fascicles (FIG. 4G) at different current amplitudes. Both graphs show the amplitude (measured as area under the curve of the response) of the recorded eCAP (expressed as % over the maximal response). SpA BF changes are expressed as maximum reduction from baseline in %, HR changes are expressed as beats per minute (bpm), sMABP changes are expressed as mmHg, and RR changes are expressed as breaths per minute (bpm). The two graphs also report the charge density per phase relative to the stimulation amplitude used.

In parallel, recording of the blood flow within the splenic vein (SpV) was recorded by using a Doppler flow probe placed at the splenic base, where the vein leaves the splenic hilum. Interestingly, stimulation (symmetric biphasic pulses, 400, 10 Hz for 1 minute) caused an increase in the mean SpV blood flow (mSpV BF) that was current amplitude dependent. Stimulation with 12 mA and 400 μs PW (36.9 μC/cm2/phase) caused a maximum increase of about 200% when compared to baseline mSpV BF. The transient reduction of mSpA BF was also accompanied by a transient increase in systemic mean arterial blood pressure (sMABP). This increase (in average between 1-6 mmHg) from baseline correlated again with the stimulation intensity (FIG. 4E). Consistent sMABP changes were observed with stimulations causing a 20-30% drop in the SpA flow. In contrast, HR was only minimally affected (≤3 bpm changes, either increase or decrease), but more consistently only with high stimulation amplitudes (≥45 μC/cm2/phase causing 3-10 bpm changes)(FIG. 4G). SpN stimulation did not affect respiratory rate (RR) in the conditions tested.

Figure 4F:
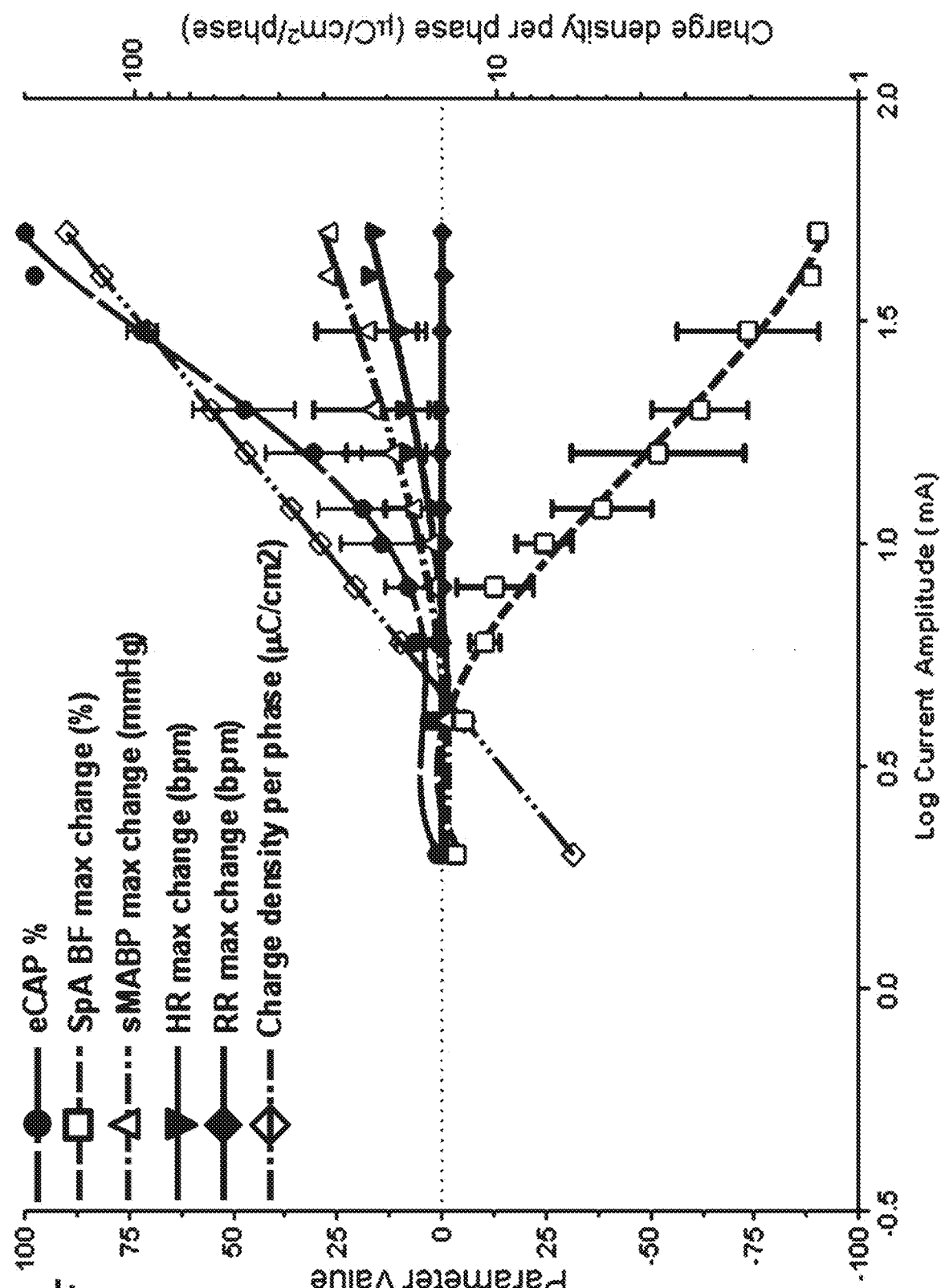
Figure 4G:
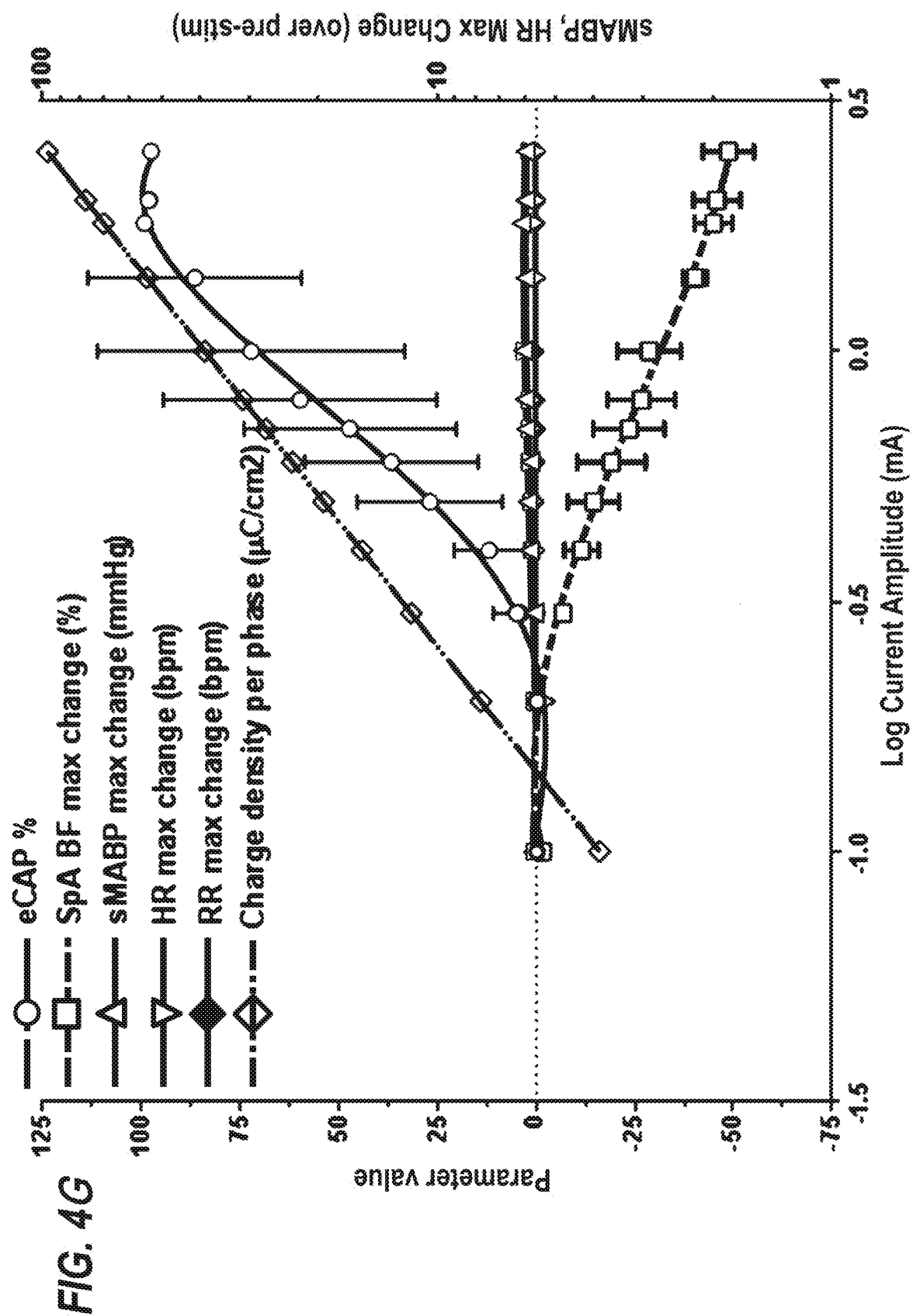

The changes observed in mSpA BF, sMABP, HR, RR during a 1-minute stimulation (symmetric biphasic pulses, 10 Hz, 400 μs PW) at different current amplitudes (1-50 mA, corresponding to 3.076-153.8 μC/cm$^2$/phase) are summarized in FIG. 4F. In FIG. 4F, it is possible to observe how the magnitude of these changes was correlated with the recording of an eCAP (black line and circles) from the SpN. The higher was the number of fibers recruited (measured as eCAP % over the maximum recorded response) the stronger was the reduction in mSpA BF and the other associated changes.

Direct stimulation of discrete SpN bundles dissected off the SpA (using a 500 μm diameter cuff) evoked similar changes in the mSpA BF, sMABP and HR. These changes, occurring during a 1 minute (symmetric biphasic pulses, 1 Hz, 400 μs PW) and different current amplitudes (0.1-2.5 mA, corresponding to 3.86-96.61 μC/cm$^2$/phase), are summarized in FIG. 4G. Even in this case the associated changes were dependent on the proportion of fibers (eCAP shown in black) recruited by the stimulation. The maximum eCAP (and therefore maximum changes) was obtained at about 153 μC/cm$^2$/phase when stimulating the whole plexus and at about 70 μC/cm$^2$/phase. The magnitude of the changes when stimulating few fascicles were lower than those obtained when stimulating the whole plexus, as expected since the total number of fibers stimulated was lower and the frequency was lower.

Figure 5B:
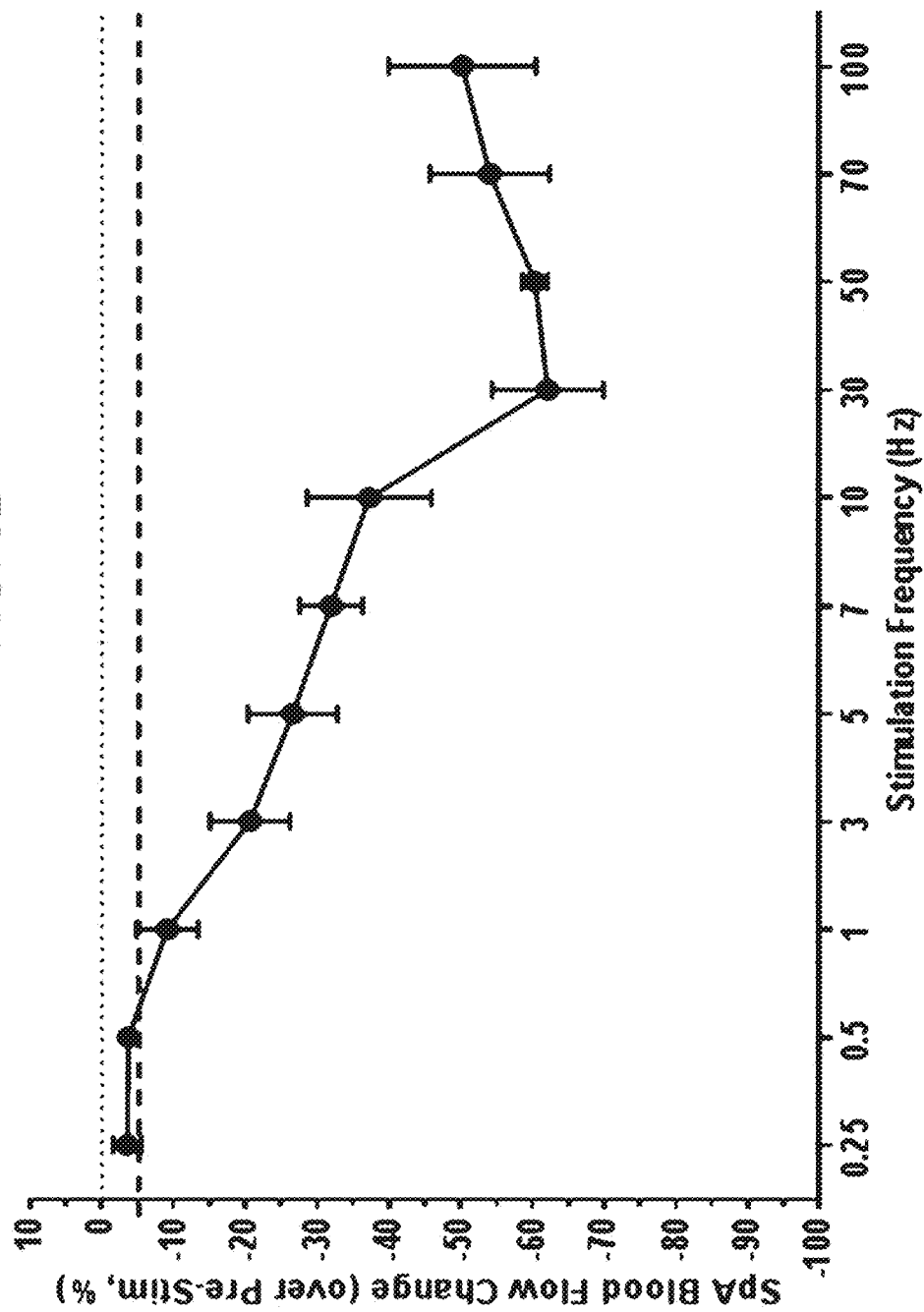
FIG. 5B shows the mean (n=3) maximum reduction in mSpA BF observed during a 1 minute stimulation (symmetric biphasic pulses, 400 µs PW at about 36.9 µC/cm$^2$/phase) of the SpN plexus at different frequencies (between 0.25 and 100 Hz).
Figure 5C:
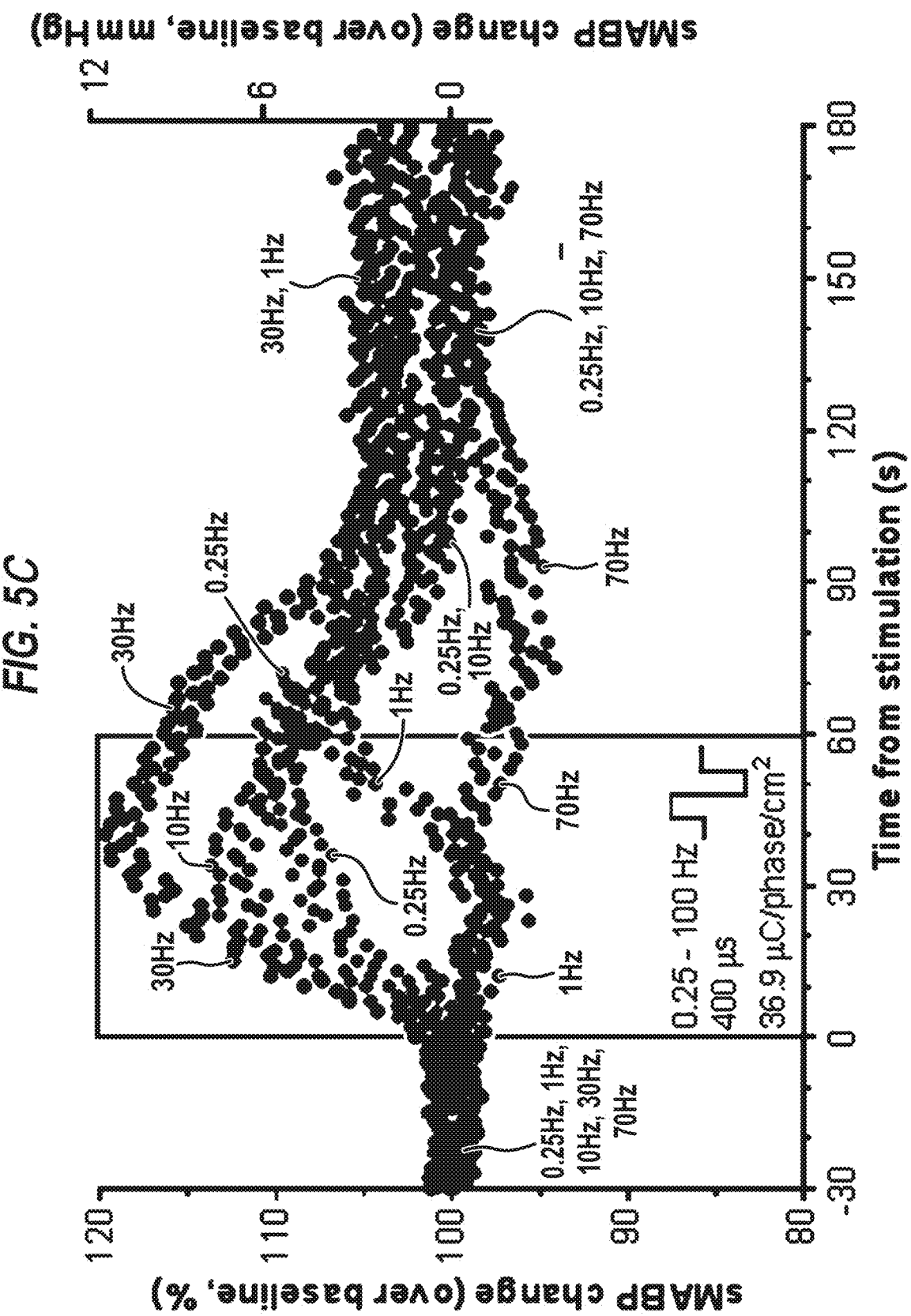
Figure 6:
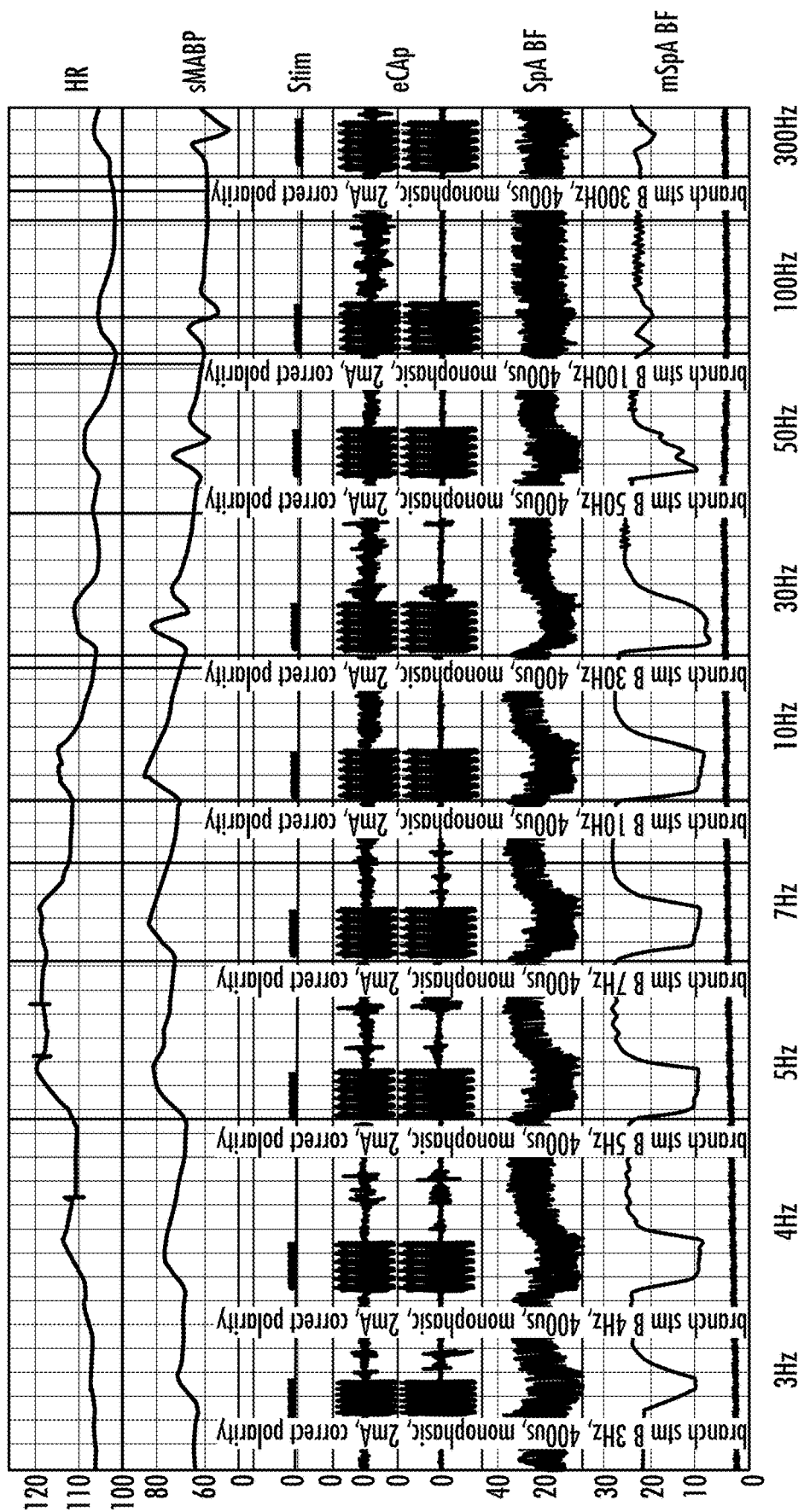
FIG. 6 shows local and systemic effects of few dissected SpN fascicles at different frequencies. In particular.

Blood flow changes in the mSpA were also affected by different frequencies of stimulation. When stimulating (symmetric biphasic pulses, 400 μs PW for 1 minute at about 36.9 μC/cm2/phase) at different frequencies (between 0.25 and 100 Hz), 30-50 Hz reliably caused the strongest blood flow reduction in the SpA (FIG. 5A). Above 50 Hz (between 70 and 100 Hz) the reduction in BF was in fact smaller, in the range of reductions obtained with a 10 Hz stimulation (FIG. 5B). The changes in mSpV BF, sMABP and HR were also found to be dependent on the frequency of the stimulation applied. The strongest effects were again observed between 30 and 50 Hz (FIGS. 5C-D).

This was once again observed when maximally (around 70 μC/cm$^2$/phase) stimulating only few fascicles dissected off the artery. A stronger reduction in mSpA BF occurred already at lower frequencies (1 Hz and below), because of the higher recruitment of nerve fibers compared to the stimulation amplitude used for the whole plexus during the frequency analysis. Consistently however, the maximal reduction was observed between 30-50 Hz (FIG. 5D).

In order to further confirm that the observed changes in SpA BF were due to direct neuronal activation (rather than stimulation of smooth muscles) Lidocaine (2% lidocaine hydrochloride solution) was applied locally around the implanted SpN cuff (either the peri-arterial cuff or the cuff for dissected fascicles). Lidocaine is a specific blocker of fast voltage gated Na+ channels. Lidocaine was able to block the changes in SpA BF. Further, mechanical occlusion of the SpA, able to reduce the BF up to 80%, did not cause any change in sMABP or HR. In addition, transection of the central end of the SpN (proximal to the cuff) did not abolish stimulation effects on SpA blood flow, sMABP and HR. Also the transection of the SpN within the GEP and SG segments did not prevent these changes. Interestingly, all these effects were only abolished when the peripheral end of the SpN (distal to the cuff) was cut. All these data suggest that the changes in SpA BF and SpV BF were neuronal driven and related to the constriction of the SpA as well as the contraction of the spleen capsule. On the other hand, the changes in sMABP and HR were probably not due to the activation of a neuronal pathway towards the brain but to the increase outflow of blood from the spleen towards the heart.

Figure 7:
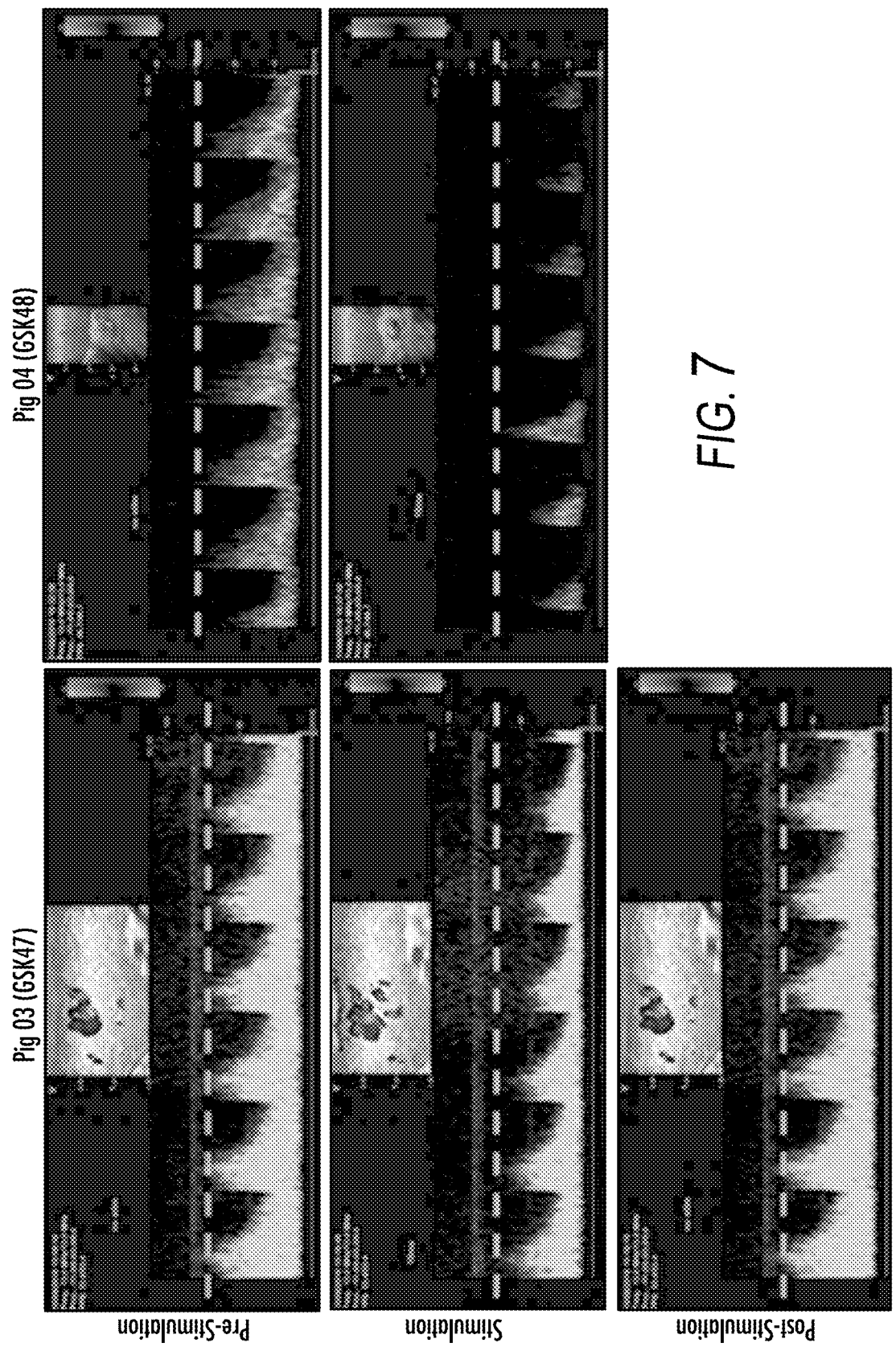
FIG. 7 shows SpA blood flow changes monitored via intra-operative splenic ultrasonography. The images of FIG. 7 were obtained from two different animals during SpN stimulation. Note the reduced Doppler trace during stimulation (middle panels) versus pre-stimulation and post-stimulation (top- and bottom panels, respectively).

In few animals, SpA blood flow changes during stimulation was also monitored using intra-operative ultrasonography at the splenic hilum. After identifying the SpA by color Doppler, the change in BF was monitored as Doppler signal as shown in FIG. 7. During stimulation at 10 Hz, a reduction in BF could be easily observed as indicated by the changed amplitude and shape of the flow traces.

Discussion

Splenic nerve stimulation was associated with transient local changes in mSpA BF and mSpV BF as well as splenic contraction. These changes were due to the direct activation of the SpN, rather than direct stimulation of the smooth muscles of the SpA. Spleen contraction during SpN stimulation has been previously reported also in other species [17]. The observed change in mSpA BF was very consistent between animals. The variation was probably mainly due to different fitting of the cuff around the SpN plexus in different animals. Changes in SpA BF could be easily monitored via non-invasive ultrasound and therefore could be used as a marker to assess effective stimulation of the SpN also in a clinical setting.

The transient changes observed during SpN stimulation were shown to be amplitude and frequency dependent. During a minute of stimulation at different current amplitudes, the strongest mSpA BF reduction was observed at the highest current amplitude tested that also corresponded to the peak of the recorded eCAP. This was true when stimulating the whole SpN plexus (with a peri-arterial cuff) or when stimulating only few fascicles placed within a smaller cuff. The difference in the total charge density needed to obtain maximum eCAP from the SpN plexus and from SpN fascicles could be explained by the partial coverage of the plexus with the 2.5 mm cuff used. In most of the pigs in fact this cuff resulted only in a 270-300 degrees of circumferential coverage. When cuffing only few fascicles of the SpN dissected off the artery the coverage was almost total. Therefore, in order to limit charge density needed to obtain optimal recruitment of SpN fascicles, optimal circumferential coverage of the artery will be needed.

The strongest changes (in mSpA BF and sMABP) were observed at frequency between 30 and 50 Hz. Although the total number of pulses delivered could be an important factor in determining the magnitude of this changes, it is true that when comparing changes occurring with the same number of pulses delivered at different frequencies, 30-50

Hz range still caused the strongest changes. This could be explained with previously reported data showing that maximum release of NA from the cat spleen was observed at 30 Hz [18,19]. Higher release of NA could explain the higher magnitude of the changes observed in this stimulation range.

Optimization of the Signal Parameters (Study 2)

Materials and Methods

In order to develop an optimized stimulation paradigm, the inventors tested several signal parameter settings in the pigs mentioned above using the materials and methods described above.

The optimization of parameters was focused at reducing off target effects and increasing efficiency of the SpN response. In particular, since the systemic changes caused by SpN stimulation were related to the local constriction of the SpA and contraction of the spleen, parameters able to minimize these changes could represent optimal paradigm to be transferred in chronic studies and clinical studies where systemic effects (e.g. changes in sMABP and HR) are not ideal.

Results

Figure 8A:
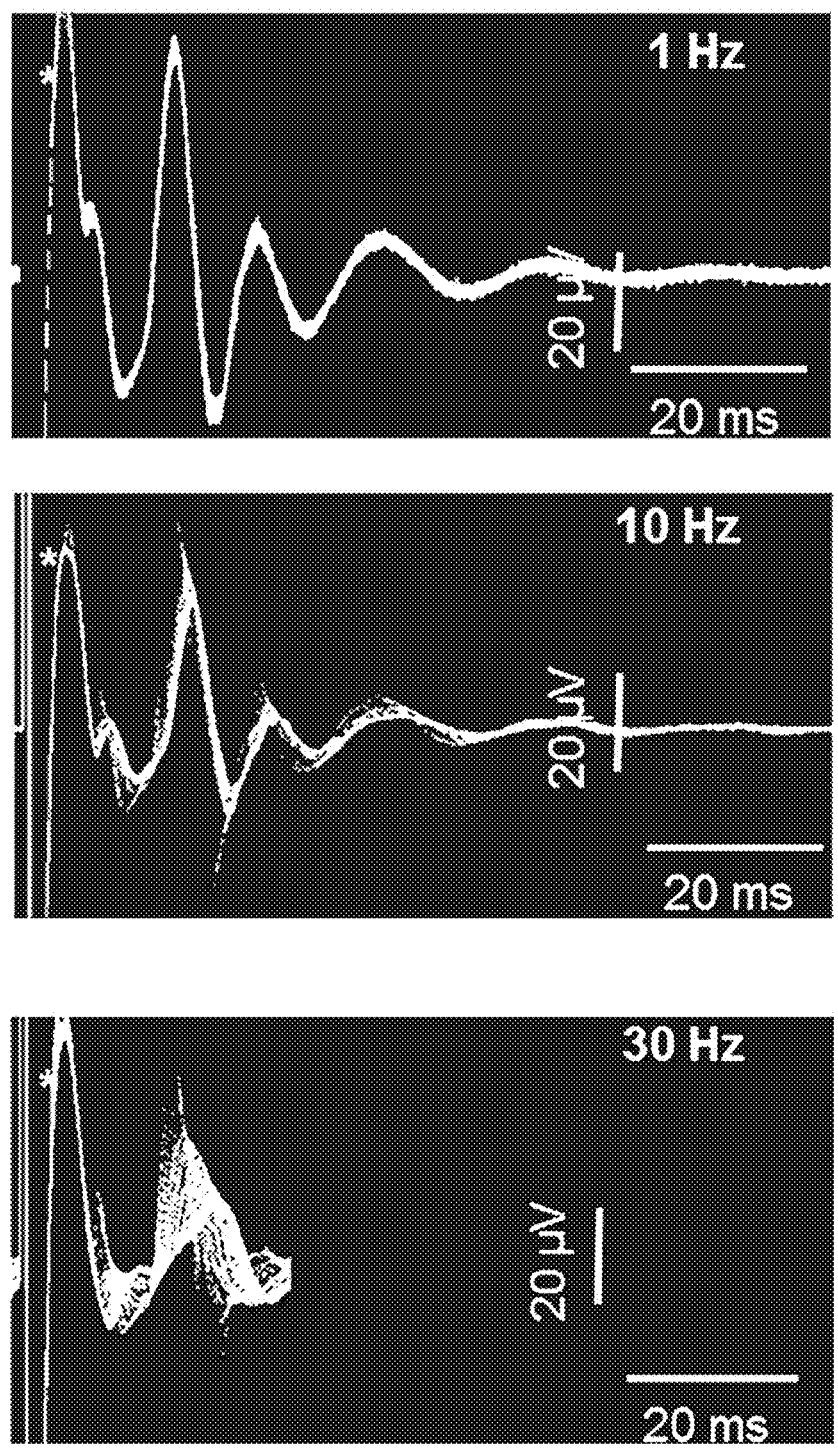
FIG. 8A shows the eCAP recorded from the SpN during a 1 minute stimulation at different frequencies (1, 10 and 30 Hz, from top to bottom). Each image show the superimposition of all the evoked responses. For 1 Hz stimulation there are 60 responses superimposed; for 10 and 30 Hz, each trace represents the average of 5 consecutive responses. Note that the responses at 10 and 30 Hz shift to the right over time and the amplitude is reduced over time.

Repetitive stimulation of the SpN was found to cause fatigue in the nerve fibers at certain frequencies. This effect consisted of two characteristics: i) a reduction of SpN eCAP amplitude and ii) slowing of SpN conduction velocity. Both these characteristics were observed at frequencies higher than 1 Hz, with fatigue effects increasing with increasing frequency. Stimulation of the SpN at 10 Hz continuously for 1 minute caused, in fact, adaptation in the recorded response, resulting in a decreased amplitude of the eCAP over time (FIG. 8A), and a reduction of conduction velocity of each of the eCAP recorded peaks. This effect was stronger (in magnitude) and faster at higher frequencies. Stimulation of the SpN at 30 Hz continuously for 1 minute, for example, caused a faster and stronger reduction in both eCAP amplitude (FIGS. 8A, 8B(I)-(III)) as well as conduction velocity. After 60 s of stimulation, 10 Hz (total of 600 pulses) pulses caused a reduction of about 60% of the eCAP maximum amplitude while 30 Hz pulses (total of 1800 pulses) resulted in about 80% reduction (FIGS. 8C, 8E). When the SpN was stimulated for 1 min with 1 Hz, instead, the reduction in eCAP over time (FIGS. 8A and 8C) was very small and no significant reduction in conduction velocity was observed. When comparing the reduction of eCAP amplitude over the same number of pulses, 10 Hz and 30 Hz still produced the faster and stronger reduction (FIG. 8C). This fatigue effect over repetitive stimulation of the SpN could be reduced by periodically switching OFF and ON the stimulation. When stimulating the SpN with a burst paradigm, for example giving 5 pulses delivered at 10 Hz, every 5 s, the reduction of eCAP and conduction velocity was abolished (FIGS. 8C to 8F).

In addition, when stimulating at 10 and 30 Hz continuously, a rapid increase in eCAP amplitude was observed within the first 5-20 pulses. This phase preceded the successive reduction in amplitude and velocity (FIGS. 8C and 8E).

Figure 8F:
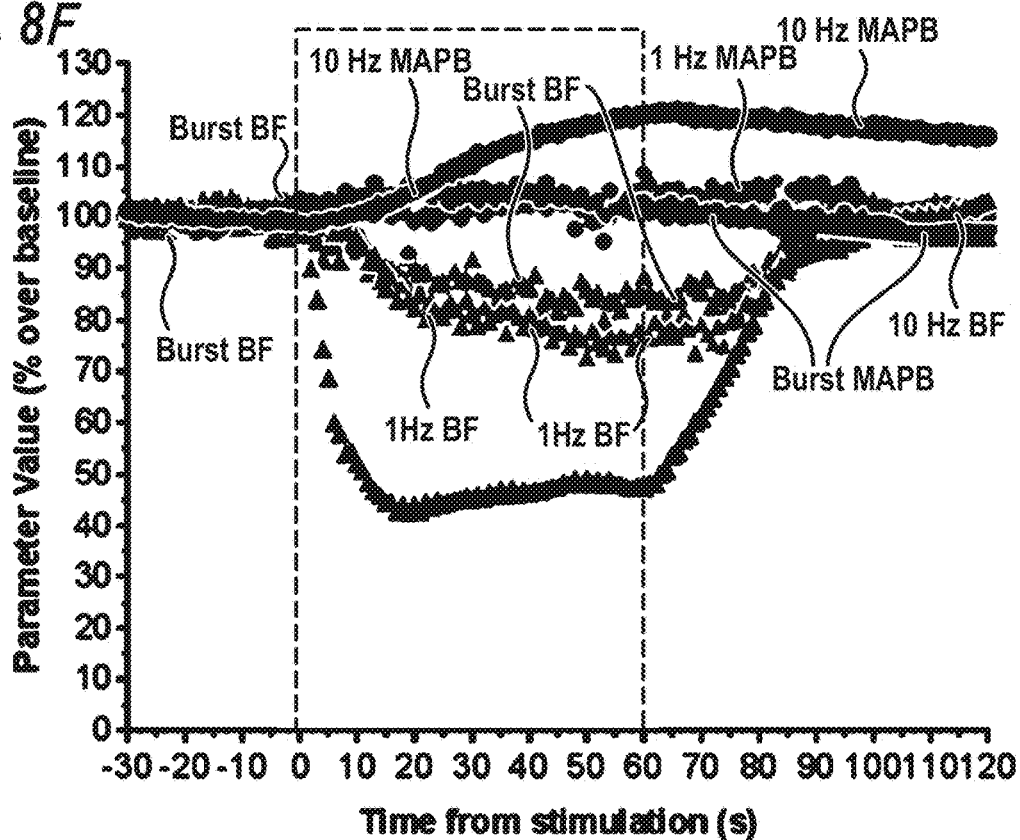
FIG. 8F shows change in SpA mBF (circles) and sMABP (triangles) during a 60 s stimulation of the porcine splenic neurovascular bundle (NVB) using 400 µs PW and 12 mA (symmetric, biphasic square pulses) delivered at 10 Hz (in black), 1 Hz (light grey) or burst stimulation (10 Hz, 5 pulses every 10 seconds, in grey). Data are from representative stimulations within the same animal.
Figure 8G:
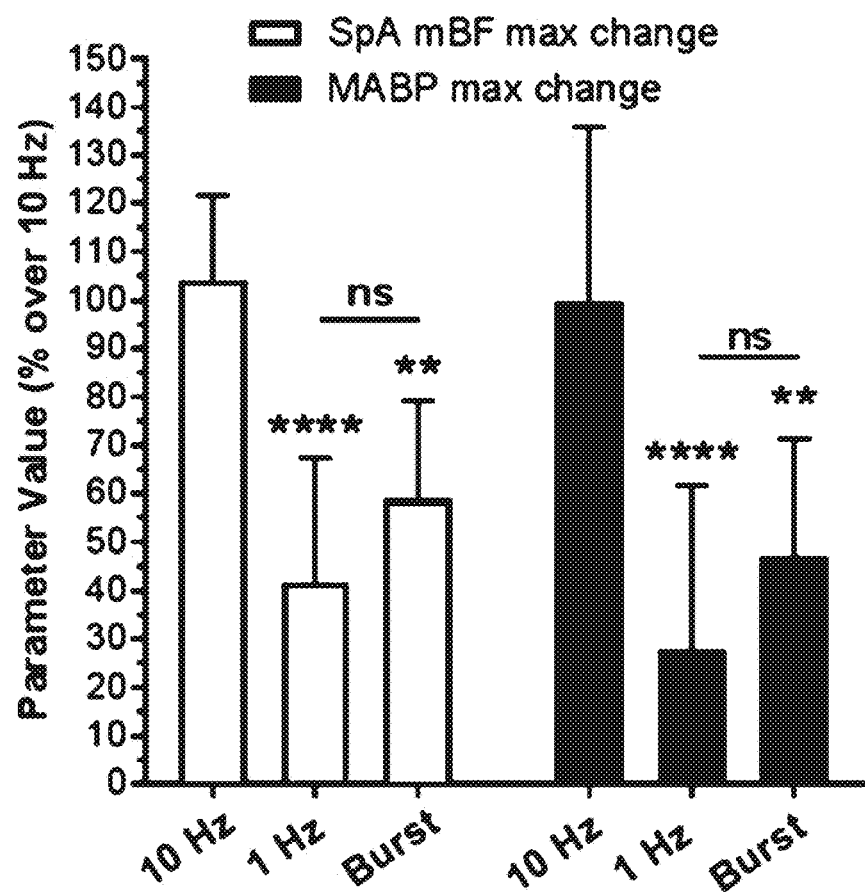
FIG. 8G shows SpA mBF and sMABP max changes recorded during a 60 s stimulation delivered with the different stimulation patterns shown in FIG. 8F. Values are expressed as % over the max change obtained at 10 Hz. Data are shown as mean (N=4)±s.d. Statistical analysis in FIG. 8C was performed using One-way ANOVA and Tukey post-hoc correction for multiple comparison. *, P≤0.05; , P≤0.005; *, P≤0.001; ****, P≤0.0001.

As described previously the frequency of the stimulation not only impacted the response of the nerve but it also affected differently the physiology. Frequencies between 30 and 50 Hz caused the strongest changes in mSpA BF that drives the changes in sMABP. Frequencies≤1 Hz caused, in comparison, little changes in mSpA BF. Frequencies between 1 and 30 Hz caused changes of mSpA BF of increasing magnitude. By selecting a high current amplitude (in order to recruit most of the SpN fibres), a 10 Hz, biphasic, symmetric 60 s stimulation is sufficient to cause, at least, a 50% maximum reduction in the mSpA BF. The stimulation of the SpN with the same biphasic symmetric pulses and current amplitude but with 1 Hz frequency, caused a reduction in mSpA BF about 40% lower (decrease from around 70% to around 50%) than the one generated with the 10 Hz stimulation (FIG. 9, FIGS. 8F and 8G).

Figure 9:
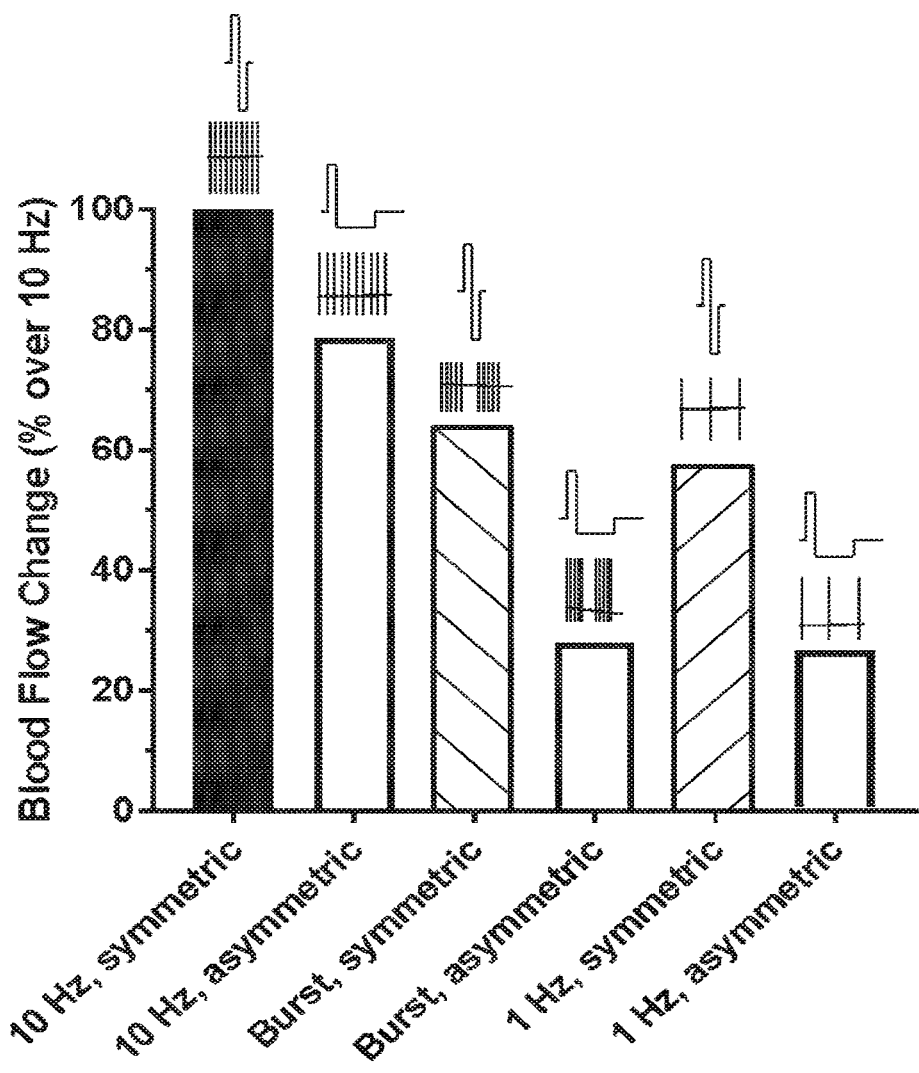
FIG. 9 shows burst and 1 Hz stimulation produced the lowest changes in mSpA BF. In particular.

The same was observed when applying a burst stimulation (5 pulses at 10 Hz every 5 s) using biphasic pulses and the same current amplitude (FIG. 9). Importantly, when the stimulation was applied as biphasic, asymmetric pulses (and same current amplitude) each of the stimulation paradigm resulted in a lower reduction of mSpA BF when compared to their respective biphasic, symmetric paradigm (FIG. 9). Even in this case 1 Hz and burst stimulations produced the lowest changes in mSpA BF.

Herein lies a description of the opportunity space to provide optimised neural activation, in the absence of 'nerve fatigue', while provide options for effectively stimulating physiological changes (high frequency), or to avoid them (low frequency or burst frequency), depending on the target profile of the therapy. During surgery it may be very effective to use blood flow changes to induce easily visualised target engagement profiles, to prove the device and therapy are appropriately positioned and of suitable amplitude. Then a switch to burst or low frequency stimulation will ensure ideal nerve engagement for efficacy in splenic engagement, while avoiding clinically consequential effects of continual changes in blood flow in awake patients.

Discussion

Parameters for optimal stimulation (and therefore efficacy) should in principle i) generate a very consistent and maintained amplitude response of the nerve, ii) deliver as many pulses as needed (to obtain the therapeutic effect) in the shortest possible time window in order to reduce energy requirement and discomfort to patients and iii) have the lowest spectrum of off target effects. The stimulation of the SpN at frequencies higher than 1 Hz showed a clear activity-dependent variations in response (eCAP) amplitude and conduction velocity. This effect has been previously observed in other unmyelinated nerves, in both rodents and humans [20,21,22,23]. During regular stimulation at 0.25 Hz, conditioning pulses intermittently interposed at varying inter-stimulus intervals, unmyelinated fibers showed a progressive reduction of conduction velocity dependent on the number of interposed stimuli [20]. The same effect was observed with stimulation of the SpN, where repetitive stimulation caused reduction in conduction velocity as well as reduction in eCPA amplitude. This effect has been previously called "subnormality" of action potential conduction.

When the SpN was stimulated continuously at 10 Hz a short period of increased response has been observed followed by the slowing and reduction of the response phase. This other period has been also described before and termed "supernormality". Supernormality and subnormality of action potential conduction are probably due an after-depolarization and a subsequent period of hyperpolarization of the membrane when pulses are delivered within a short time window (below 1000 ms from one another) [20,21,22]. When recording eCAP, this membrane changes in the axons that cause an increase in the current activation threshold, resulted in a lower amplitude of the recorded signal. This was not simply an effect of the slowing of the conduction velocity: the recorded eCAP shifted to longer latencies and decreased in amplitude without spreading in total width. In fact the measured AUC was smaller over time. However, it still possible that the observed reduction in eCAP amplitude was due to a de-synchronization of the action potentials that then cancel each other when recording a compound response. Single unit recording would be ideal to demonstrate that the SpN is really subjected to this activity-dependent changes.

It has been shown here that low frequency stimulation (1 Hz or below) or burst stimulation (5 pulses at 10 Hz, every 5 s) caused limited or no fatigue on the SpN as well as caused the lowest off target effects. To date these two paradigms, delivered with biphasic, asymmetrical pulses, represent the optimal stimulation pattern for the SpN for treatment of immune-mediated conditions (e.g. inflammatory disorders). Frequencies higher than 1 Hz, induce changes in blood flow and pressure, and could be useful in identifying nerve-target engagement during electrode positioning.

Effects of Electrostimulation in an In Vivo LPS Animal Model (Study 3)

Materials and Methods

Animals

A total of 18 pigs (over the initial 38) (age/weight) were used for this section of the study. None of these 18 pigs were excluded from the analysis.

General Design

Three hours after the initial stimulations performed as part of another study aim, 18 animals received an intravenous injection of 2.5 μg/kg endotoxin (Purified lipopolysaccharides from the cell membrane of *Escherichia coli* O111:B4; Sigma Aldrich), administered over a period of 5 minutes. This dose was selected through a thorough review of the available literature and personal experiences. This dose was chosen to cause a septic shock-type of model. Animals which received SpN stimulation 3 hours prior to LPS injection were divided in 2 groups: the SpNS did not receive any further stimulation whereas the SpN2S received asecond SpN stimulation during the LPS injection.

The stimulation parameters include a 1 minute duration, with square, biphasic, charge balanced symmetrical pulses at 10 Hz, with a 400 μs pulse duration and a current amplitude corresponding to a charge density per phase of 30 to 90 μC/Cm$^2$/phase. The stimulation was applied once and then repeated a second time 3 hours later at the time where LPS was injected in vivo.

Peripheral venous blood was collected immediately prior to LPS injection (baseline), and then every half hour up to 2 hours post injection. At the end of this time-window pigs were euthanized or used for further final electrophysiological tests. For all of these time points, cytokine analysis (TNFα and IL-6), and routine hematology and biochemistry analyses were performed. Serum was diluted 1:10 for the cytokine analyses.

In animals where the LPS injection caused clinical changes in systemic blood pressure and/or cardiac function, standard clinical therapies such as vasopressin (2.5 IU bolus injections administered i.v. and repeated as needed) and anti-arrhythmic drugs (lidocaine; 2 mg/kg i.v. and/or atropine; 40 μg/kg; i.v.) were given at the discretion of the anesthetist. Animals were euthanized when mean systemic arterial pressure could not be maintained ≥40 mm Hg, or when the animal completed the pre-determined endpoint.

Statistical Analyses

All analyses were performed with commercially available statistical software (JIVIP Pro 13.0.0). Continuous variables were visually inspected for normality and outliers. When outliers were identified, statistical tests were performed including and excluding these animals as stated in the result section.

Changes in cytokine and leukocyte levels were calculated as the percentage of baseline samples collected immediately prior to LPS injection. Cytokine and leukocyte levels were subsequently analyzed using a mixed model with stimulation group, time and stimulation group*time as fixed effects, and animal as random effect. Pairwise Student's t-tests were used for Post Hoc analysis. Differences in survival time between stimulation groups was analyzed using the Log Rank test and plotted in a Kaplan Meier plot. Cytokine levels, leukocytes and electrolytes were compared between the different treatment groups at 30 minutes post LPS injection using a two-way ANOVA analysis with Post Hoc All Pairs Student's t-test analysis; this test was also used to compare maximal reduction in mean arterial blood pressure between groups. Statistical significance was defined as P≤0.05.

Results

Survival

Administration of a high dose of LPS caused a rapid change in systemic arterial blood pressure within 5-10 minutes post LPS administration. In the sham (non-stimulated) animals these changes were stronger and more rapid. Many animals required interventions (e.g. injection of vasopressin) in order to maintain safe levels of blood pressure (mean ABP≥40 mmHg). However, in most of the animals the intervention was not enough to restore safe levels of ABP and animals required euthanasia. In addition, few animals showed Tachyarrhythmia and severe tachycardia. Stimulated animals (especially those receiving 2 splenic nerve stimulations) showed lower magnitude changes and a more stable cardiovascular response. The events recorded after LPS administration in stimulate and sham animals are summarized in table 2.

Table 2 describes cardiovascular changes after LPS administration. The table shows the changes in mean arterial blood pressure (MABP) observed in the animals after LPS administration, and treatment administered to individual pigs. The time represent the time after LPS injection. MASS=external chest (cardiac) massage; VAS=administration of vasopressin (2.5 μg/kg i.v.); ATR=administration of atropine; LID=administration of lidocaine; Time Euth=time (minutes) from administration of the LPS to euthanasia; the pre-determined end-point was at 120 minutes.

TABLE 2

| Group | Pig# | Changes in MABP | Cardiac abnormalities | MASS | VAS | ATR | LID | Time Euth |
|---|---|---|---|---|---|---|---|---|
| Sham | 1 | Severe hypotension at 10 min | Severe tachycardia | 20 min | 20 min | | | 30 min |
| | 2 | Severe hypotension at 10 min | Severe tachycardia | 20 min | 10 min | | | 20 min |

TABLE 2-continued

| Group | Pig# | Changes in MABP | Cardiac abnormalities | MASS | VAS | ATR | LID | Time Euth |
|---|---|---|---|---|---|---|---|---|
| | 3 | Moderate hypotension at 20 min Severe hypotension at 80 min | Tachyarrhythmia | — | 20, 25, 30, 35, 40, 45, 50, 55 min | | | 80 min |
| | 4 | Severe hypotension at 10 min | — | — | 10 min | 20 min | 20 min | 30 min |
| | 5 | Severe hypotension at 10 min | Tachyarrhythmia | 20 min | 10, 20 min | 20 min | | 25 min |
| | 6 | Moderate hypotension at 90 min | Severe tachycardia | — | 90 min | | | 120 min |
| SpNS | 1 | Moderate hypotension at 100 min | Tachyarrhythmia | — | 100 min | | 100 | 120 min |
| | 2 | — | — | — | — | — | — | 120 min |
| | 3 | Hypotension at 20 min | — | — | 20 min | — | — | 120 min |
| | 4 | Severe Hypotension at 20 min | — | — | 20 min | — | — | 30 min |
| | 5 | Severe Hypotension at 20 min | — | — | 20 min | — | — | 40 min |
| | 6 | — | — | — | — | — | — | 120 min |
| SpN2S | 1 | Moderate Hypotension at 20 min; Normotension at 60 min | — | — | 20, 30 min | — | — | 120 min |
| | 2 | — | — | — | — | — | — | 120 min |
| | 3 | — | — | — | — | — | — | 120 min |
| | 4 | — | — | — | — | — | — | 120 min |
| | 5 | Severe Hypotension at 20 min | Tachyarrhythmia | 30 min | 20 min | 30 min | 30 min | 40 min |
| | 6 | — | — | — | — | — | — | 120 min |

Figure 10A:
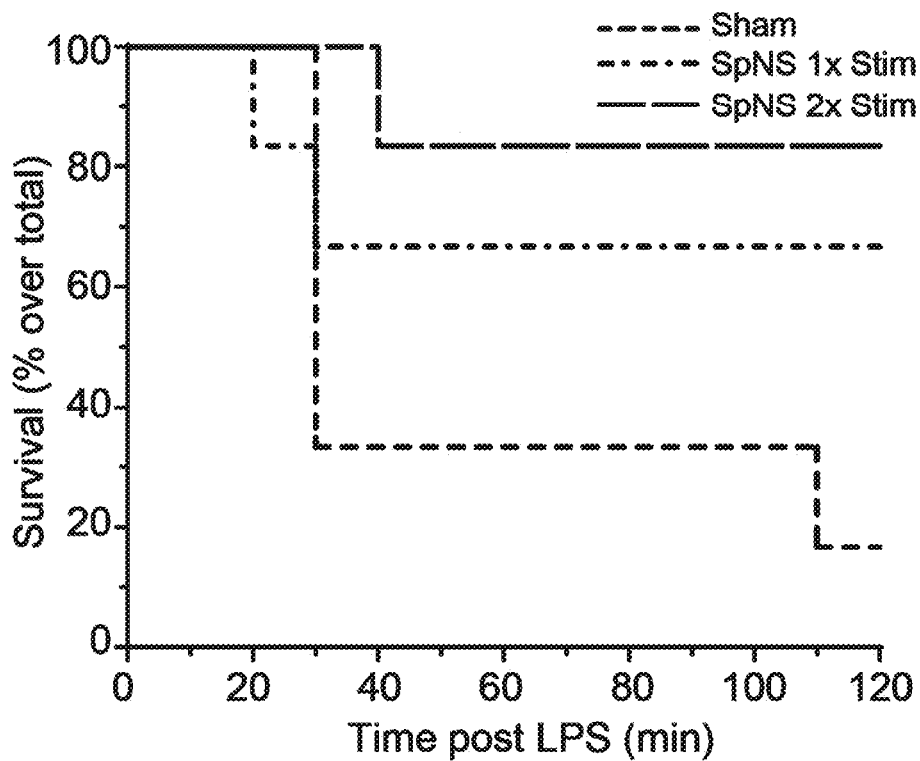
FIG. 10A is a Kaplan-Meier plot illustrating differences in survival time up to the pre-determined end-point at 2 hours post in vivo LPS injection.
Figure 10B:
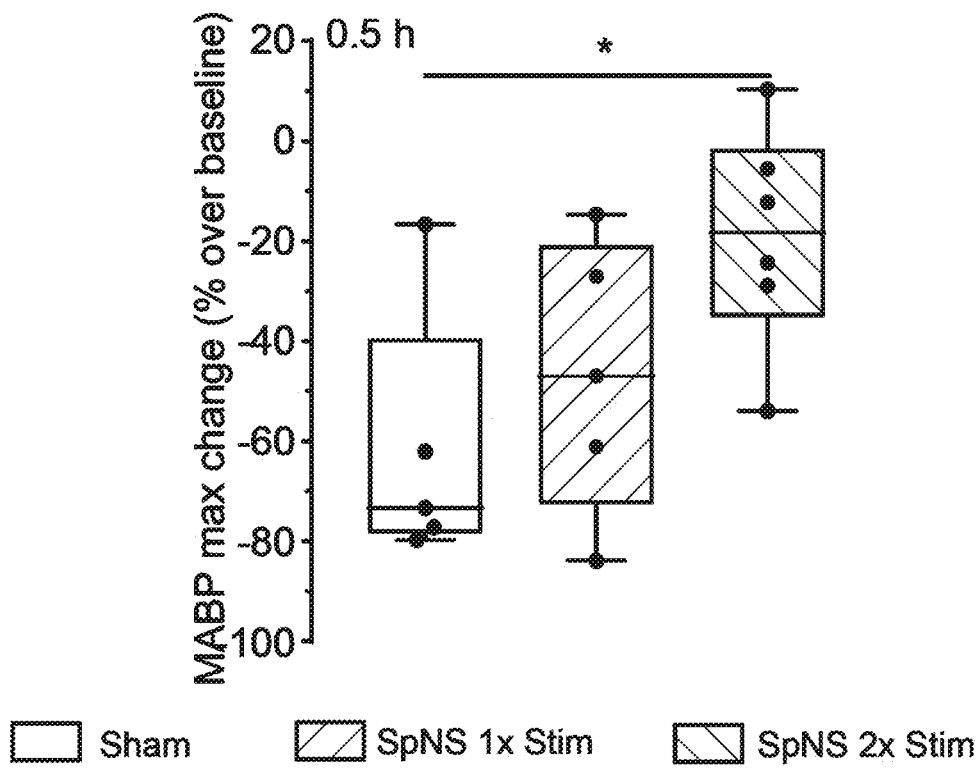
FIG. 10B is a box plot illustrating the lowest recorded mean arterial blood pressure (MABP; calculated as % of baseline) 30 minutes post LPS injection. A significant difference between SpN-T and sham group is shown; P=0.0296.
Figure 10C:
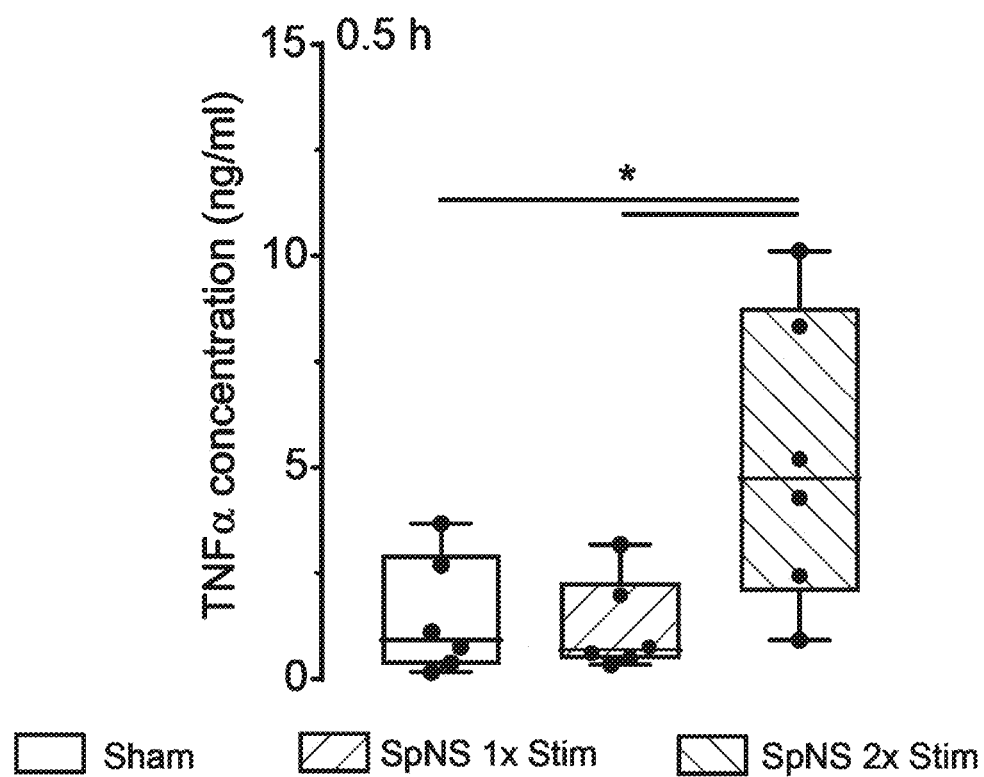
FIGS. 10C and 10D are box plots illustrating the TNFα (FIG. 10C) and IL-6 (FIG. 10D) concentrations at 0.5 hour post in vivo LPS injection. A significant difference between SpN-T and SpN-P groups is shown; P=0.0117. A significant difference between SpN-T and sham groups is also shown; P=0.0043.
Figure 11A:
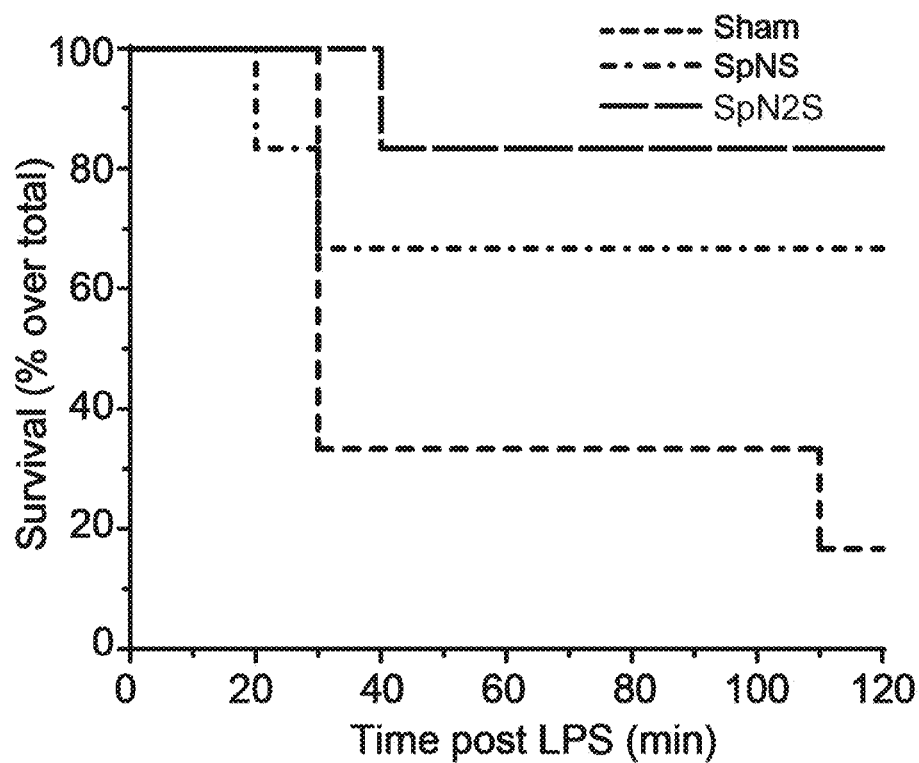
FIG. 11A is a Kaplan-Meier plot illustrating differences in survival time up to the pre-determined end-point at 2 hours post LPS injection.
Figure 11B:
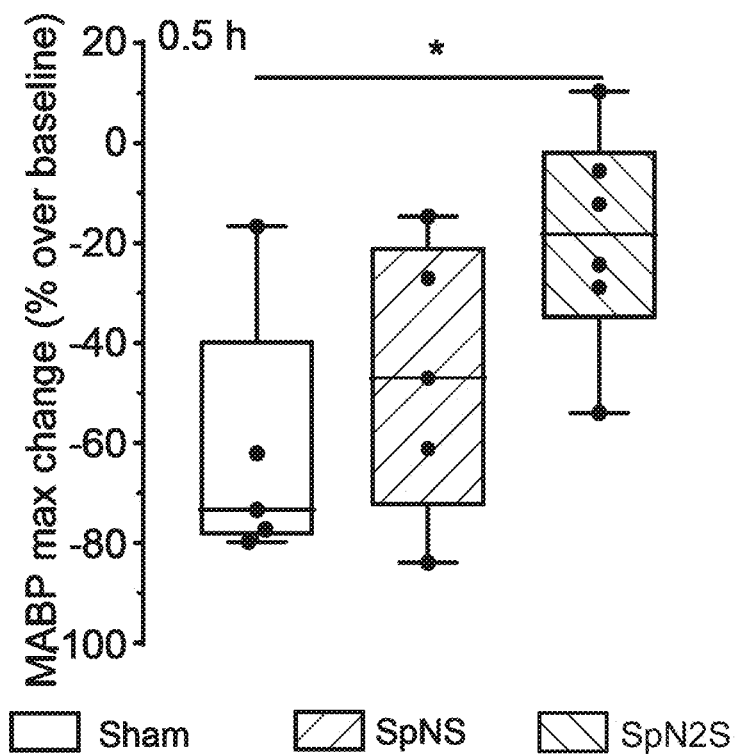
FIG. 11B is a box plot illustrating the lowest recorded mean arterial blood pressure (MABP; calculated as % of baseline) 30 minutes post LPS injection. A significant difference between SpN2S and sham group is shown.

The 2 hours post injection survival rate is reported in FIG. 10A and FIG. 11A. There was a statistical significant difference in survival rate between the SpN-T vs. Sham (P=0.0194). In brief, LPS injection evoked severe cardiovascular compromise within 10-20 minutes in 5/6 sham animals, necessitating euthanasia (MAP≤40 mm Hg despite treatment) prior to reaching the pre-determined endpoint. Conversely, in 5/6 SpN-T stimulated animals, and 4/6 SpN-P stimulated animals, vital parameters including mean arterial blood pressure remained stable throughout the experiment period; for these groups, MAP at 2 hours post injection was 95.3±13.5, 85.9±7.5 and 86.8±9.7% of baseline values, respectively. Likewise, there was a statistically significant difference in maximal reduction in MAP between the SpN-T vs. Sham (P=0.0296, FIG. 10B and FIG. 11B); mean MAP at the time of euthanasia was 87.1±23.5% of baseline in the SpN-T group (mean survival time 1.8±0.5 hours post injection); 62.7±33.0% of baseline in the SpN-P group (mean survival time 1.4±0.8 hours post injection); and 48.6±37.9% of baseline in the Sham group (mean survival time 0.9±0.7 hours post injection).

Cytokine quantification: For all groups, LPS injection resulted in a significant increase in TNFα levels in all post-injection samples compared to baseline (P≤0.001; FIG. 10C to 10D and FIG. 11C to 11D), with the peak response observed at 1 hour post injection. IL-6 was significantly higher at 2 hours post injection compared to baseline across all groups (P≤0.0001).

Figure 10D:
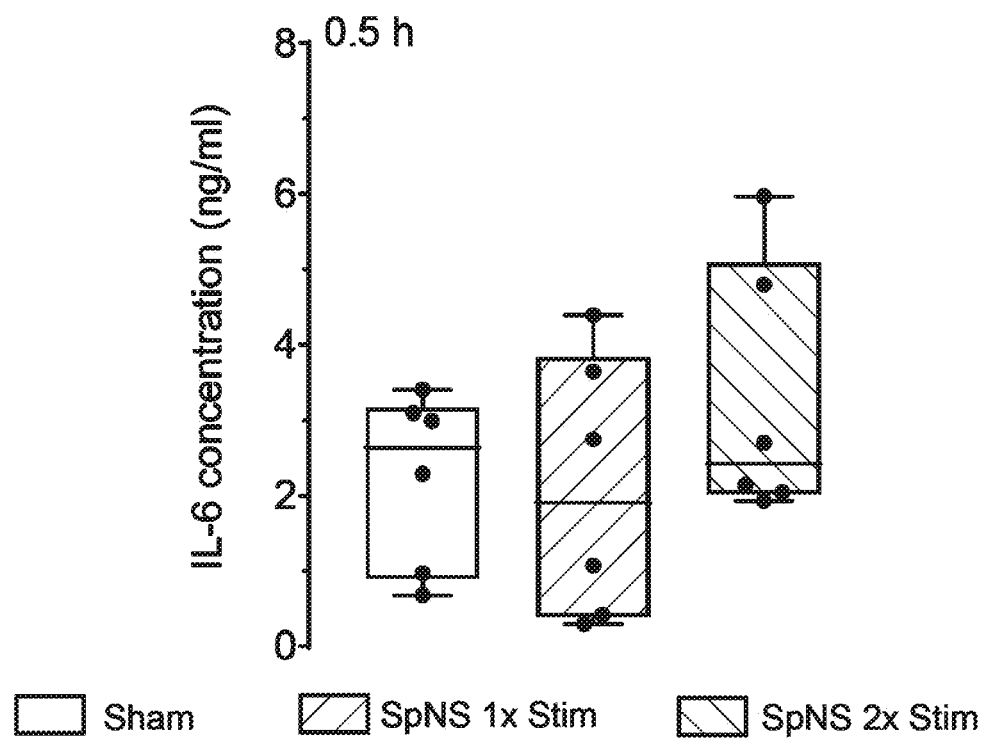
Figure 11C:
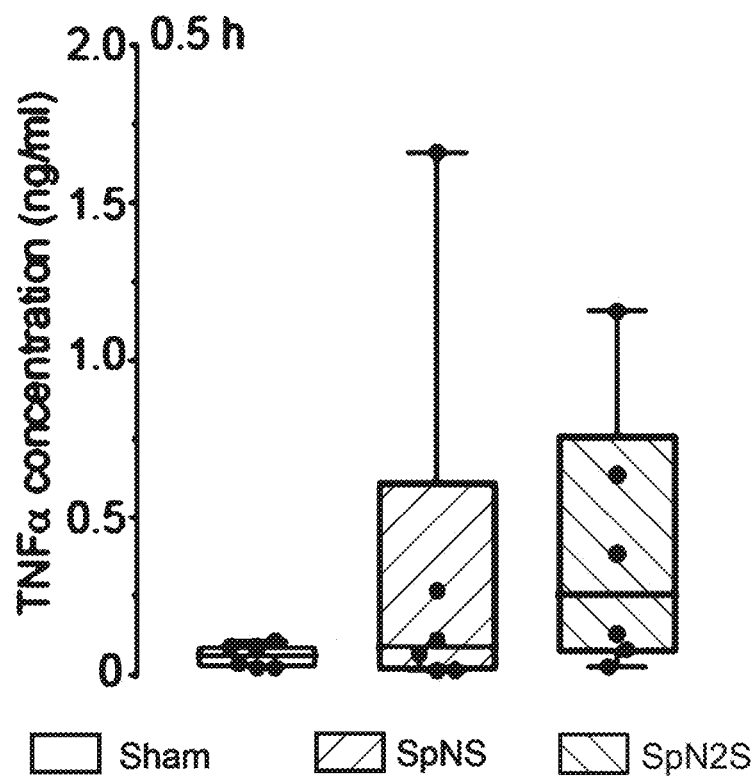
FIGS. 11C and 11D are box plots illustrating the TNFα (FIG. 11C) and IL-6 (FIG. 11D) concentrations at 0.5 hour post LPS injection.
Figure 11D:
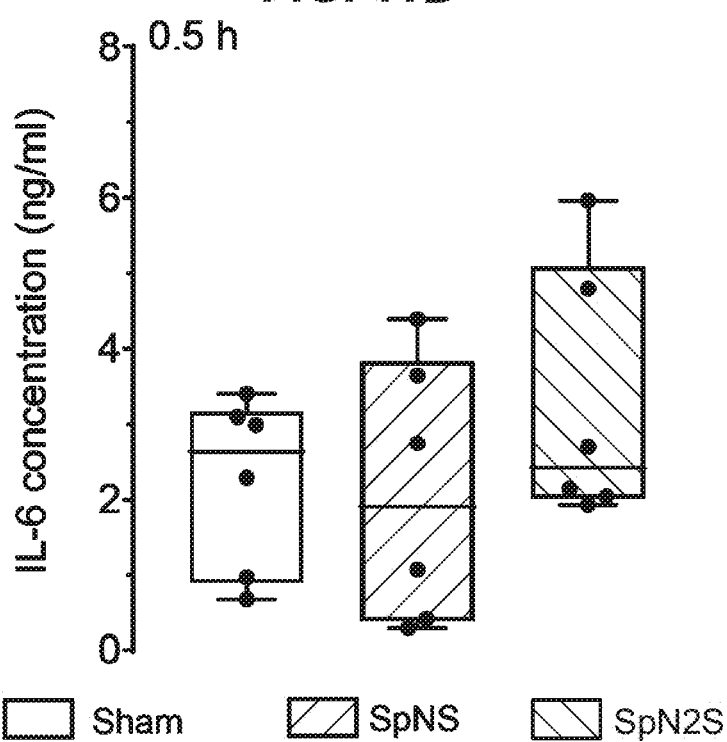

When comparing cytokine levels at 0.5 hours post injection, TNFα levels as well as IL-6 levels were not found significantly different between the sham and stimulated groups (FIGS. 10D, 11C and 11D).

Discussion

The administration of LPS in vivo to mimic an inflammatory response provided a good model to test the efficacy of SpN. The administration of LPS (2.5 µg/Kg of body weight) in 45-50 kg pigs caused upregulation of cytokines (TNFα and IL-6) in the blood of all the animals tested. In particular, TNFα reached a peak value of about 12 ng/ml at 1 h post injection while IL-6 picked around 15 ng/ml at 2 h post LPS. The LPS also caused significant changes in the peripheral blood composition, with reduction in circulating lymphocytes and neutrophils (results not shown). White blood cells in fact probably leaves the circulation to infiltrate tissues and organs during the systemic infection mimicked by the LPS. A significant increase in blood urea, creatinine and total bilirubin as well as an increase in CK and ALP over time was also observed after LPS (results not shown). All these changes indicated that the model was effective and reproducible between animals.

Strikingly sham animals showed a very rapid and strong decrease in systemic MABP, at about 10-15 minutes post LPS administration. Reduction in systemic MABP reached levels that would be rapidly life threatening levels, requiring the administration of vasopressin. However, in most of the controls this was not sufficient to stably restore a normal sMABP. Even when further injections of vasopressin were performed, 4/6 sham controls had to be euthanized at 30 minutes post LPS injection since their sMABP could not be kept above 40 mmHg. One of the sham was instead euthanized 110 minutes post LPS injection for the same reason. In some cases, arrhythmias were also observed.

On the opposite, most of the animals that were stimulated (at either –3 h or at –3 h and 0 h, relative to LPS) did not show such strong changes in sMABP. Most of them did not require any pharmacological intervention (i.e. vasopressin). This pro-survival effect of SpN stimulation, however, could not be explained by a lowering of the concentration of LPS-induced cytokines. TNFα and IL-6, in fact, measured at 30 minutes post LPS injection were not reduced in the stimulated animals when compared to sham animals. Therefore, even though this model provided the proof that SpN stimulation is able to modulate the response to an inflammatory stimulus, this could not be simply explained by a reduction in the inflammatory response.

Summary

In summary, the inventors found that neural stimulation of a nerve supplying the spleen, and in particular, the splenic arterial nerve, showed pro-survival effects in an in vivo LPS animal model. The inventors also found that electrical stimulation of the splenic arterial nerves stabilized blood pressure, which drops dramatically in LPS-treated animals, and reduced the maximum reduction in blood pressure. Hence, stimulation of the neural activity of splenic nerves can be particularly useful for treating acute medical conditions, such as life-threatening conditions having physiological changes associated with shock, blood loss, and cardiovascular dysfunction (e.g. trauma, hemorrhaging and septic shock).

Effects of Continuous Electrostimulation in In Vivo LPS Animal Model (Study 4)

Materials and Methods

Animals

A total of 23 pigs (weight 65-70 Kg) were used for this section of the study.

General Design

Pigs were terminally anesthetized and split into the following five groups: sham (implanted with electrodes but not stimulated), Dexamethasone (the SpN was accessed and then animals were injected with Dexamethasone at –2 and 0 h), LVNS (pigs were implanted on the cervical LVN), eLVNS (pigs were implanted on the cervical LVN, that was ligated and cut distal to the cuff electrode and the efferent stump only stimulated), and SpNS (pigs were implanted on the peri-arterial SpN).

The implanted devices of the LVNS, eLVNS and SpNS pigs were stimulated continuously from –2 h to +1 h (relative to the injection of LPS) at 1 Hz. E. coli-derived LPS was administered at a dose of 0.25 μg/Kg to all groups at 0 h. Dexamethasone was used as positive control.

Peripheral venous blood was collected for 2 h prior to LPS injection (baseline), and then every half hour up to 4 hours post injection. For all of these time points, cytokine analysis (TNFα and IL-6), was performed by commercially available ELISAs.

Results

Figure 12A:
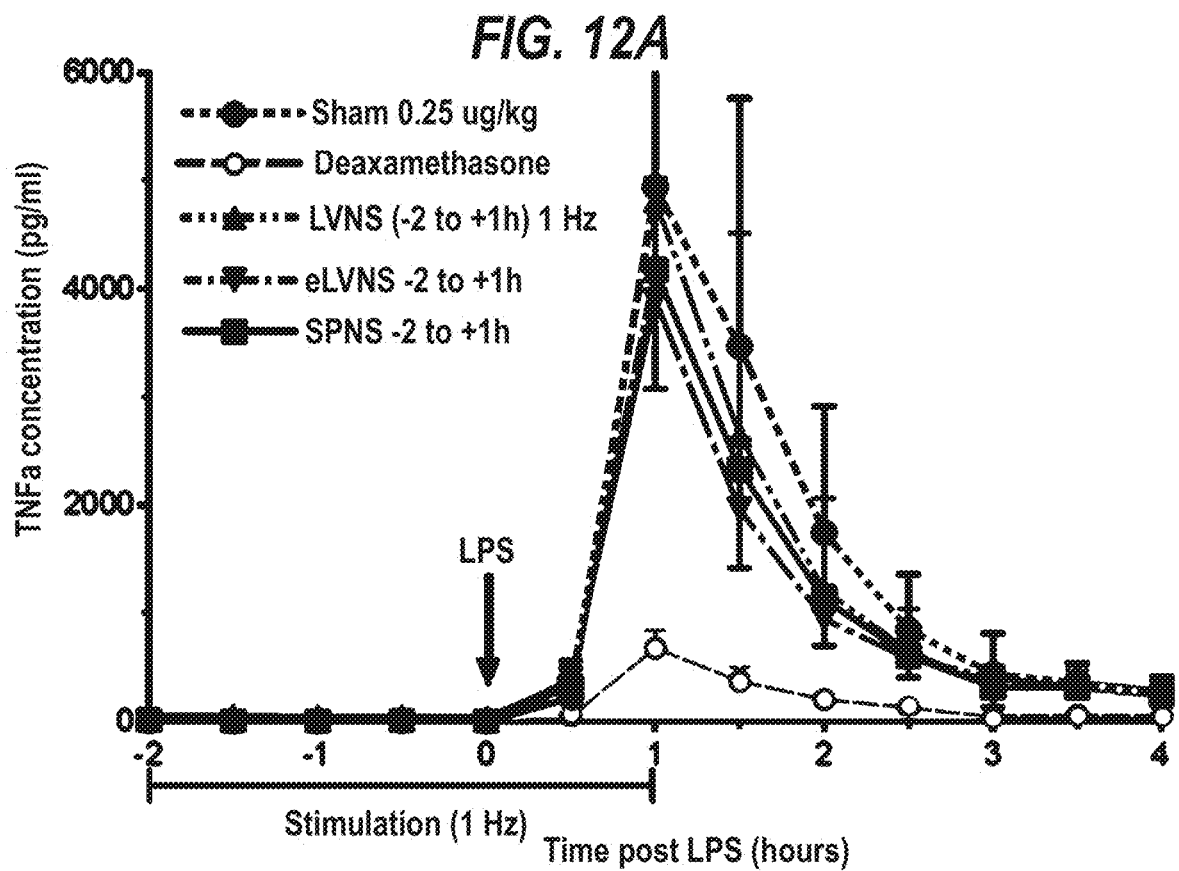
FIGS. 12A and 12B show the dynamic change in TNFα (FIG. 12A) and IL-6 (FIG. 12B) measured directly from plasma collected by terminally anesthetized pigs administered with 0.25 µg of E. coli LPS.
Figure 12B:
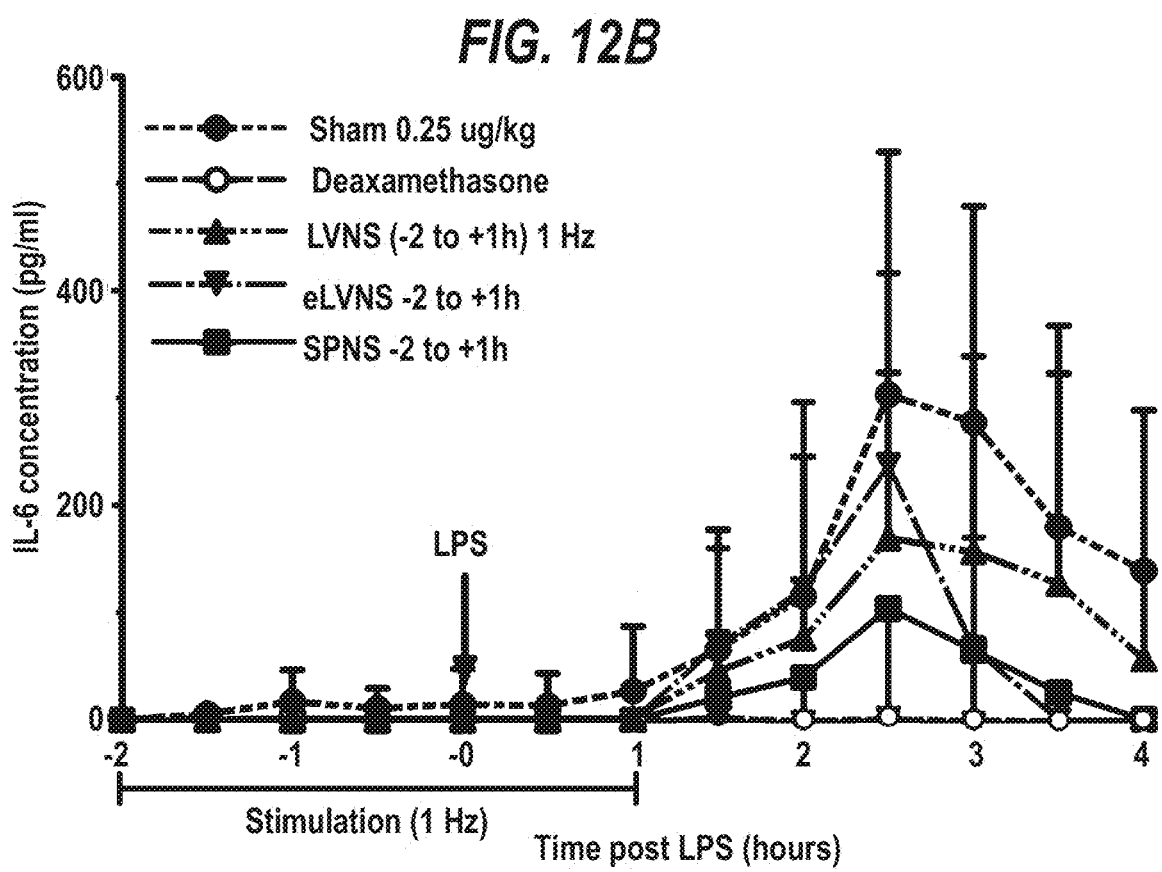
Figure 12C:
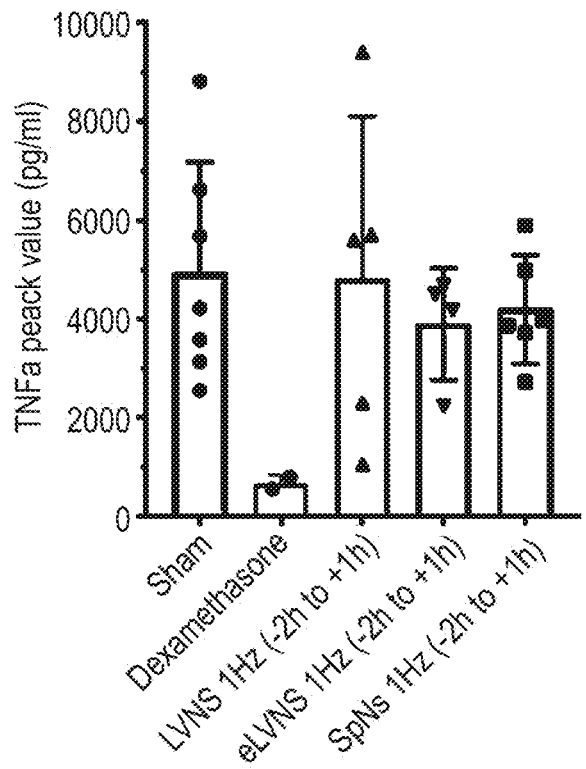
FIGS. 12C and 12E show the peak value of TNFα (FIG. 12C) and IL-6 (FIG. 12E) measured in the plasma after LPS administration in the different groups.
Figure 12D:
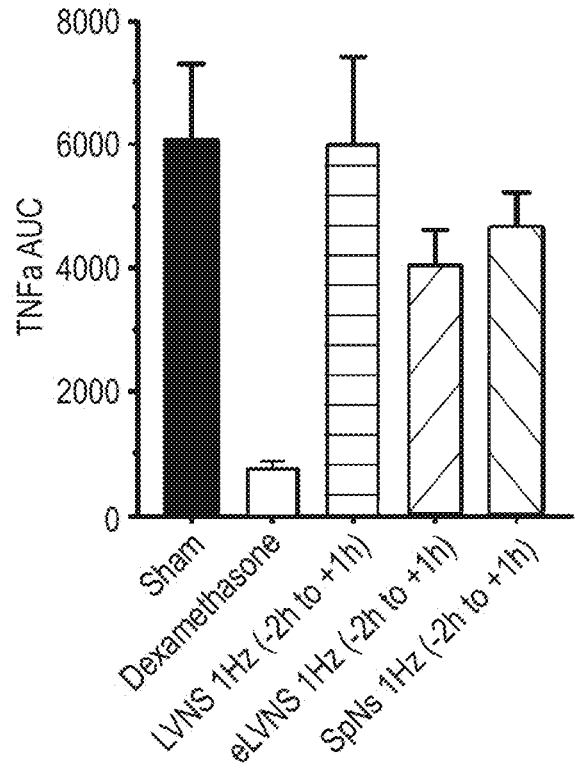
FIGS. 12D and 12F show the quantification of the Area under the curve (AUC) of both TNFα (FIG. 12D) and IL-6 (FIG. 12F). Data are expressed as mean (Sham: N=6, Dexamethasone: N=2, LVNS: N=5, eLVNS: N=5, SpNS: N=6)+/−SD.

Cytokine quantification. For all groups, LPS injection resulted in a significant increase in TNFα levels in all post-injection samples compared to baseline (pre-LPS injection), with the peak response observed at approximately 1 hour post injection (FIG. 12A). A similar trend was observed for IL-6. IL-6 response peaked approximately 2.5 hours post injection.

Figure 12E:
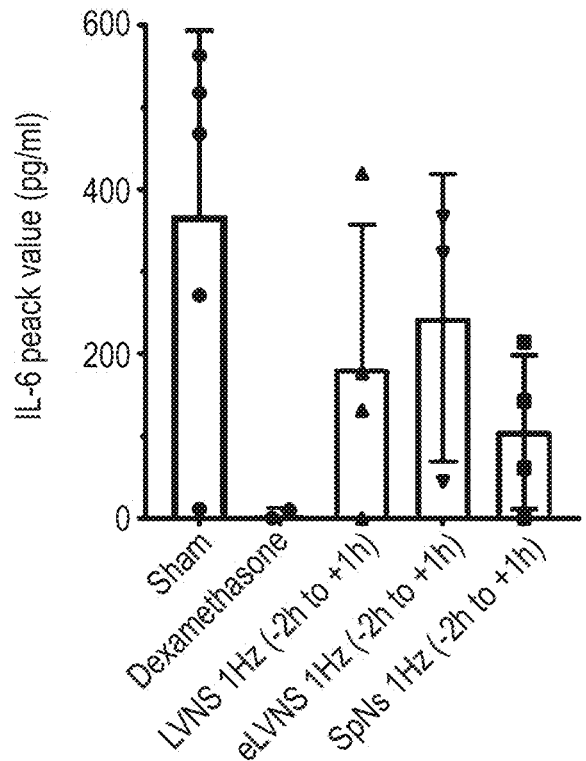
Figure 12F:
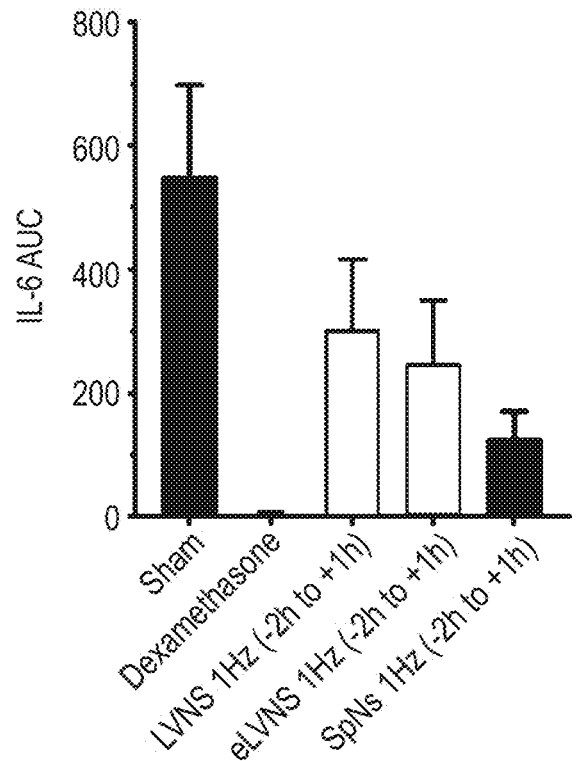

Cytokine levels were compared between groups by calculating the area under the curve (AUC) from between –2 h to +4 h post-injection. TNFα levels were only slightly reduced in SpN as well as LVNS and eLVNS groups when compared to Sham. For IL-6, there was a reduction in both the peak response value (FIG. 12E) and the AUC (FIG. 12F) in SpNS group. Similar reduction was also observed for LVNS and eVLNS groups compared to the sham control.

Discussion

The administration of LPS in vivo to mimic an inflammatory response provided a good model to test the efficacy of SpN stimulation. The administration of LPS (0.25 μg/Kg) in 65-70 kg pigs caused upregulation of cytokines (TNFα and IL-6) in the blood of all the animals tested. In particular, TNFα reached a peak value of about 5 ng/ml at 1 h post injection while IL-6 peaked at around 0.5 ng/ml at 2.5 h post LPS injection.

Therefore, this model provides the proof that SpN stimulation is able to modulate the response to an inflammatory stimulus, and shows that prolonged stimulation of SpN reduces the levels of pro-inflammatory cytokines, as seen in particular by the reduction of IL-6. This is likely to be beneficial for reducing inflammatory responses in subjects, particularly in light of recent evidence showing the vagus nerve stimulation is beneficial in the treatment of autoimmune disorders.

Summary

In summary, the inventors found that neural stimulation of a nerve supplying the spleen, and in particular, the splenic arterial nerve, showed pro-survival effects in an in vivo LPS animal model. Hence, stimulation of the neural activity of splenic nerves can be particularly useful for treating inflammatory disorders, Characterization of the Splenic Arterial Loop (Study 5)

Materials and Methods

To investigate the different neural pathways to the spleen, six formaldehyde preserved human cadavers were studied. Tissue blocks of the spleen, stomach, pancreas, greater omentum, gastrosplenic ligament and, if present, the phrenic splenic ligament were removed.

Multiple characteristics relevant to the splenic plexus were analyzed, including dissection parameters of the splenic artery in general (for example, length, cross-sectional diameter, etc) the splenic arterial loops and branches of the splenic artery, as well parameters relating to the relationship of the splenic artery with surrounding tissues.

Tissue samples of the splenic artery were also analyzed by immunohistochemical staining (IHC). IHC was used to detect and quantify associated nervous tissue. General, sympathetic and afferent nervous tissue were immunohistochemically detected in tissue resections by using anti-Protein Gene Product 9.5 (PGP9.5), anti-Tyrosine Hydroxylase (TH) and anti-Calcitonin Gene-Related Peptide (CGRP) antibodies, respectively. Immunohistochemical staining and visualization was performed using routine procedures. For all splenic plexus samples, automatically stitched overview images (tile scans) were generated from composite brightfield and fluorescent microscopy images and were the subject of further image analysis using FIJI Image J (with additional plug-ins).

Results

In all cases, the splenic artery originated from the coeliac trunk. The course was mostly suprapancreatic, although in some cadavers parts of the splenic artery were retropancreatic, intrapancreatic or anteropancreatic.

The average absolute length of the splenic artery (measured by placing a cord along the splenic artery) was 18.02 cm, with an average straight line distance from the origin at the coeliac trunk to the imaginary sagittal plane of the spleen of 11.67 cm. The imaginary sagittal plane describes the line connecting the upper and lower pole of the spleen. The average diameter of the splenic artery at its origin was 0.52 cm. The average diameter of the splenic artery before its terminal branches was 0.40 cm. The average number of terminal branches was 5.5 (2-9) and the average diameter of the terminal branches was 0.22 cm (0.05-0.5). Table 1 shows the parameters of the splenic artery for each cadaver analyzed as well as the average value for each parameter.

TABLE 1

Quantitative data on general dissection parameters concerning the SA of each cadaver, followed by the average value.

| | Cadaver nr. | | | | | | |
|---|---|---|---|---|---|---|---|
| | III | IV | VII | VIII | IX | X | Average |
| Absolute length SA (cm) | 18.3 | 24.5 | 19.5 | 19.9 | 12.9 | 13.0 | 18.02 (12.9-24.5) |
| Distance origin SA to spleen (cm) | 10.5 | 16.5 | 12.5 | 12.0 | 8.5 | 10.0 | 11.67 (8.5-16.5) |
| Diameter SA at origin (cm) | 0.6 | 0.3 | 0.65 | 0.45 | 0.6 | 0.5 | 0.52 (0.3-0.65) |
| Diameter SA before terminal branches (cm) | 0.4 | 0.4 | 0.5 | 0.3 | 0.5 | 0.3 | 0.40 (0.3-0.5) |
| Diameter terminal branches (cm) | 1: 0.4<br>2: 0.1 | 1: 0.4<br>2: 0.25<br>3: 0.2<br>4: 0.2<br>5: 0.2<br>6: 0.2<br>7: 0.2<br>8: 0.1<br>9: 0.1 | 1: 0.5<br>2: 0.15<br>3: 0.3<br>4: 0.3<br>5: 0.15<br>6: 0.15<br>7: 0.1<br>8: 0.1<br>9: 0.05 | 1: 0.25<br>2: 0.25<br>3: 0.15<br>4: 0.2 | 1: 0.1<br>2: 0.3<br>3: 0.3<br>4: 0.15 | 1: 0.1<br>2: 0.3<br>3: 0.4<br>4: 0.3<br>5: 0.25 | 0.22 (0.05-0.5) |

Figure 13A:
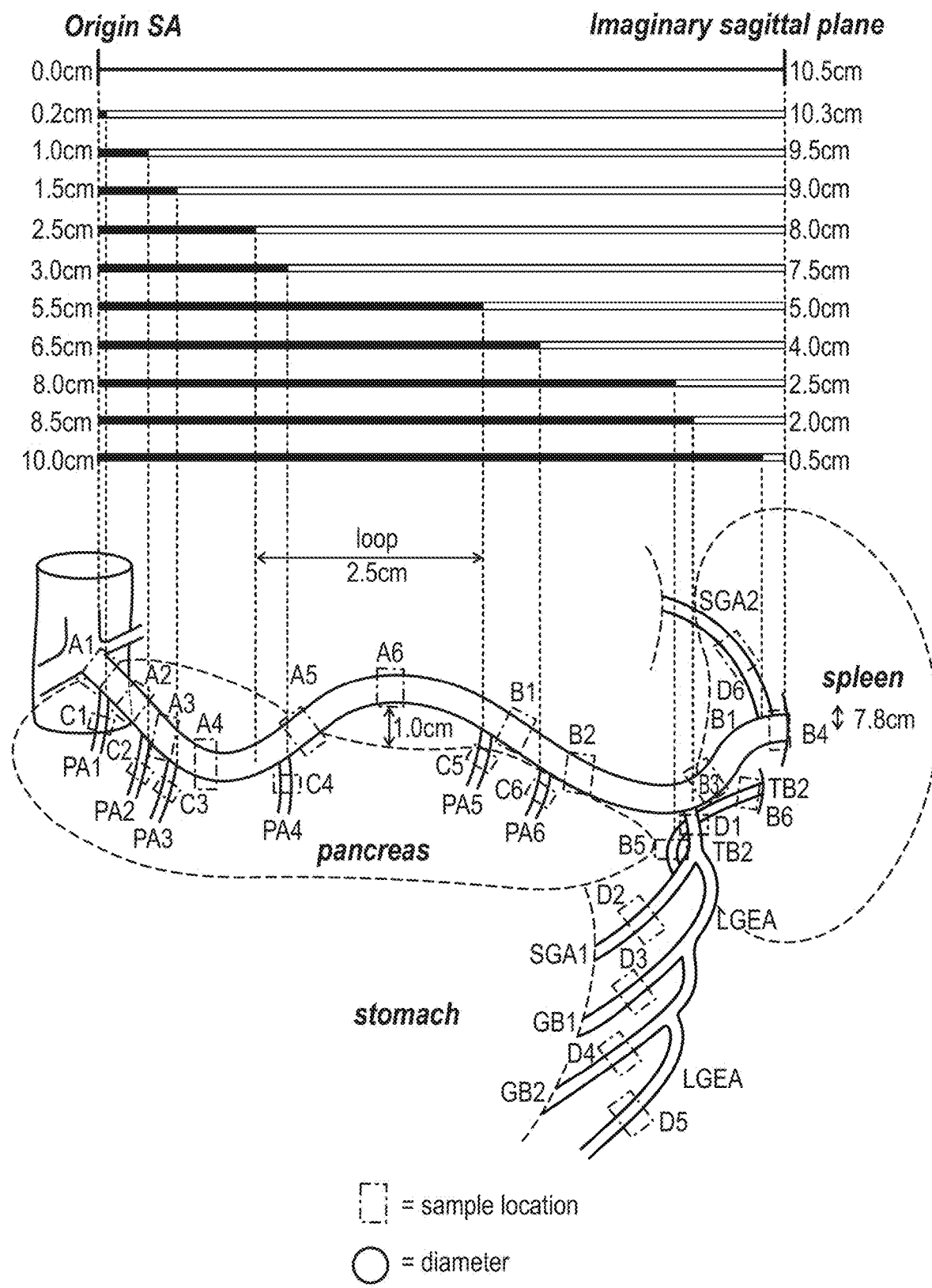
FIGS. 13A-C show the anatomical analysis of the splenic artery from Cadaver III.
Figure 13B:
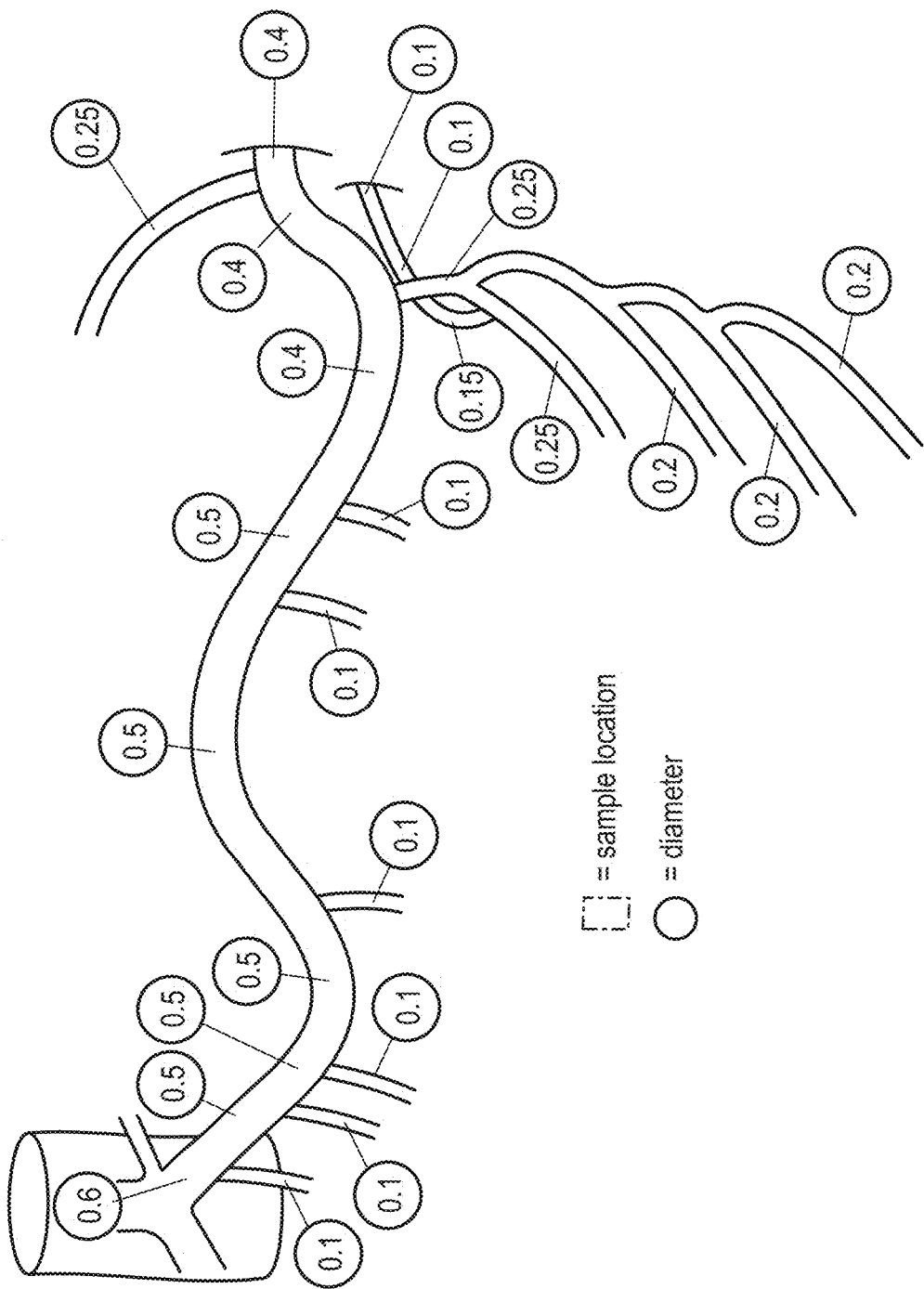
Figure 13C:
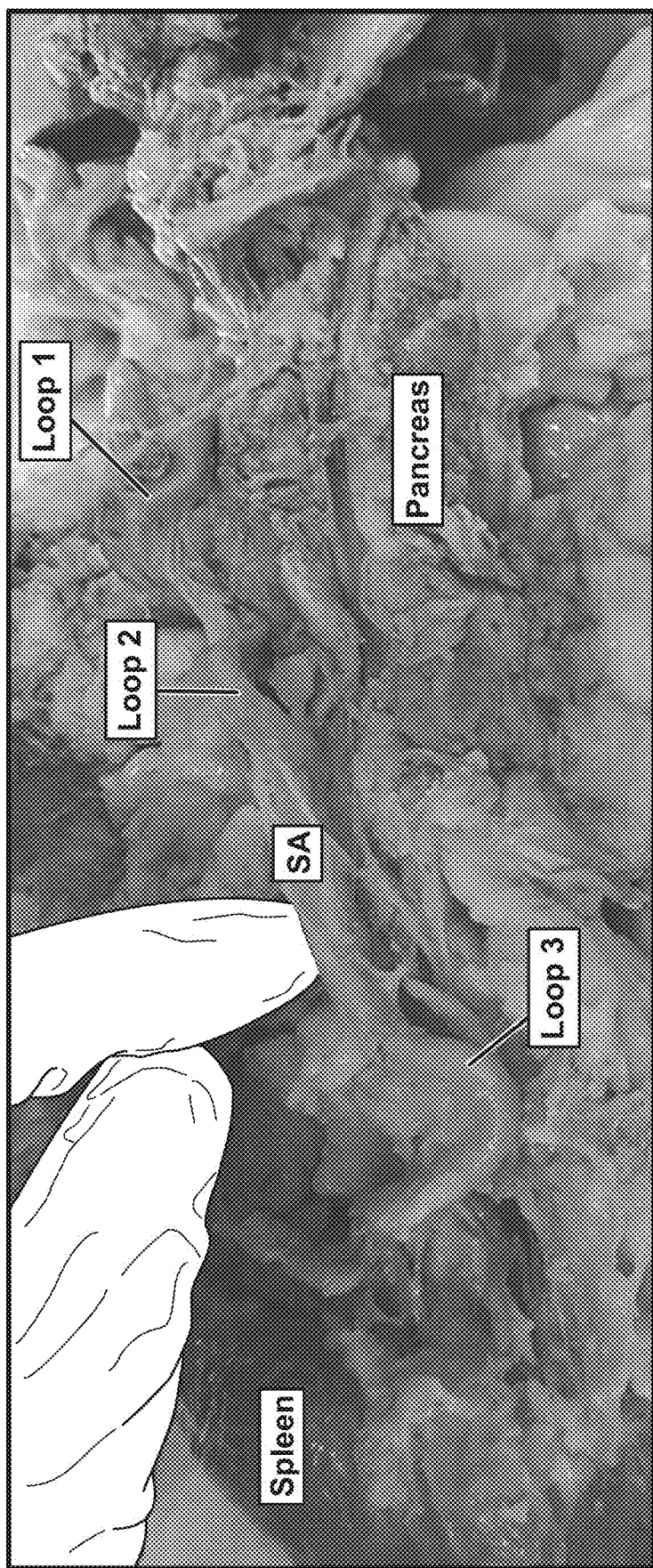

FIG. 13A shows an overview of the splenic artery and its branches of cadaver III. Distances from each branch to the origin of the SA and to the imaginary sagittal plane of the spleen are shown. In addition, the location and dimensions of the loop can be seen. The boxes show the location of the samples removed for microscopy. In FIG. 13B, the diameter of certain points along the splenic artery and its branches are depicted.

Splenic Arterial Loops

In the context of this example, a splenic arterial loop is defined as a section of the splenic artery separated from the surface of the pancreas by a distance of at least 1.0 cm. This distance is calculated from the inner curvature of the splenic artery to the surface of the pancreas.

The average number of "loops" observed across the analyzed sample pool was 1.34. One cadaver did not present any loops, three cadavers presented one loop, one cadaver presented two loops and one cadaver presented three loops. The average loop neck (the distance between the inside curvature of both legs of the loop) was 1.99 cm. The average distance from the outside of the first leg of the loop to the splenic arterial origin was 6.48 cm. The average distance from the outside of the second leg of the loop to the imaginal sagittal plane of the spleen was 4.34 cm. Both these distance were highly variable. The average loop height (the distance between the inner curvature on top of the loop, and the surface of the pancreas) was 1.29 cm. The average diameter of the splenic artery preceding the first leg of the loop and succeeding the second leg of the loop were 0.46 cm and 0.41 cm, respectively. The individual and average splenic arterial loop parameters of each cadaver are shown in Table 2.

TABLE 2

Quantitative data on dissection parameters concerning the loop(s) of each cadaver, followed by the average value.

| | Cadaver. | | | | | | | |
|---|---|---|---|---|---|---|---|---|
| | III | IV | VII | VIII | IX | X | | Average |
| Loop number. | 1 | 1 | 2 | 3 | 1 | 1 | 2 | — | 1 | 1.34 (0.0-3.0) |
| Loop neck (cm) | 2.5 | 1.5 | 1.1 | 2.3 | 2.0 | 2.0 | 1.5 | — | 3.0 | 1.99 (1.1-3.0) |
| Distance loop to origin SA (cm) | 2.5 | 5.0 | 8.5 | 12.5 | 8.0 | 3.2 | 7.1 | — | 5.0 | 6.48 (2.5-12.5) |
| Distance loop to spleen (cm) | 5.0 | 8.5 | 6.5 | 1.5 | 2.0 | 6.2 | 2.5 | — | 2.5 | 4.34 (1.5-8.5) |
| Loop height (cm) | 1.0 | 1.0 | 1.0 | 1.8 | 1.7 | 1.5 | 1.3 | — | 1.0 | 1.29 (1.0-1.8) |
| Diameter SA before loop (cm) | 0.5 | 0.5 | 0.5 | 0.4 | 0.6 | 0.4 | 0.4 | — | 0.4 | 0.46 (0.4-0.6) |
| Diameter SA first leg loop (cm) | 0.5 | 0.5 | 0.5 | 0.4 | 0.5 | 0.4 | 0.4 | — | 0.3 | 0.44 (0.3-0.5) |
| Diameter SA second leg loop (cm) | 0.5 | 0.5 | 0.5 | 0.4 | 0.5 | 0.4 | 0.3 | — | 0.3 | 0.43 (0.3-0.5) |
| Diameter SA after loop (cm) | 0.5 | 0.5 | 0.4 | 0.4 | 0.5 | 0.4 | 0.3 | — | 0.3 | 0.41 (0.3-0.5) |

Immunohistochemical Staining.

Results of the Immunohistochemical analysis of nerve bundles surrounding splenic arterial loops is shown in Table 3. The average number of nerve bundles around a splenic arterial loop was 25. The average diameter of nerve bundles was 119 μm. The average total area of sympathetic (TH-IR) nervous tissue was 196986 μm$^2$ (12645-815135), which is on average 0.54% (0.10-1.50) of the total tissue area. The diameter of the neurovascular bundle (the splenic artery and the surrounding tissue), was an average of 8553 µm (5177-12447). The distance of the nerve bundles to the location of the cuff (the outer lining of the tissue) was on average 628 µm (32-2678).

TABLE 3

Average values of all sample locations of loops of the SA for each image analysis parameter.

| | Average nerve bundle parameters of the splenic arterial loop |
|---|---|
| Number of nerve bundles | 25 (11-45) |
| Diameter nerve bundle (µm) | 119 (25-996) |
| Total TH-IR tissue (µm$^2$) | 196986 (12645-815135) |
| % TH-IR of total tissue | 0.54 (0.01-1.50) |
| Diameter neurovascular bundle (µm) | 8553 (5177-12447) |
| Distance to cuff (µm) | 628 (32-2678) |

In general, total PGP-IR (general nervous tissue) and TH-IR (sympathetic neural tissue) staining was comparable in nervous bundles surrounding splenic arterial loops. There was minimal staining of CGRP-IR (afferent nervous tissue). A sample of the total area of PGP-IR, TH-IR, and CGRP-IR nervous tissue calculated for three samples obtained from separate cadavers in shown in Table 5.

TABLE 4

Results first image analysis performed on three sample locations of the splenic loop of different cadavers, comparing the amount (and percentage) of PGP-IR, TH-IR, and CGRP-IR nervous tissue.

| | Cadaver III (A5) | Cadaver IV (A5) | Cadaver VII (A6) |
|---|---|---|---|
| Total area PGP-IR nervous tissue (µm$^2$) | 247505 | 192682 | 530856 |
| Total area TH-IR nervous tissue (µm$^2$) | 301675 (121.89%) | 171133 (88.82%) | 516263 (97.25%) |
| Total area CGRP-IR nervous tissue (µm$^2$) | 1.581 (0.64%) | 3692 (1.92%) | 4354 (0.82%) |

Discussion

The analysis performed here shows that the splenic arterial loop is a commonly observed feature of the splenic artery. The loops are generally characterized by have a separating distance from the surface of the spleen to the inside curvature of the splenic artery of about 1 cm. This separating distance makes these sites useful targets for the surgical implantation of neural stimulation systems for neuromodulation of the splenic arterial nerve. The splenic arterial loops are more accessible, and carry less risk associated with surgical-induced trauma, by negating the need to excise the splenic artery from the surface of the pancreas.

Effects of Splenic Arterial Nerve Stimulation Before and after the Onset of Disease in Mice with Collagen-Induced Arthritis Materials and Methods Implantation and Stimulation For splenic nerve implantation, one mm length 100 µm-sling bipolar micro-cuff electrodes (CorTec) were implanted onto the splenic arterial nerve. Mice were anesthetized and Cortec electrodes were implanted onto the arterial splenic nerves. Five days following surgery, stimulation was started in the prophylactic treatment groups, either 1× or 6× a day, and at day 28, ×6 a day in the treatment group with active disease (rectangular charged-balanced biphasic pulses with 650 µA pulse amplitude, 2 ms pulse width (positive and negative) at 10 Hz frequency for 2 minutes.

Induction of Collagen-Induced Arthritis and Clinical Score

Bovine type II collagen (2 mg/ml in 0.05M acetic acid; Chondrex, Redmond, Wash.) was mixed in an equal volume of Freund's complete adjuvant (2 mg/ml of *Mycobacterium tuberculosis*; Chondrex). The mice were immunized intradermally at the base of the tail with 100 µl of emulsion (100 µg collagen) on day 0. On day 21, mice received an IP booster injection of 100 µg type II collagen in phosphate buffered saline (PBS). At day 11, mice were anaesthetized with isoflurane and the spleen area was exposed. One mm length 100 µm-sling micro-cuff electrode (CorTec) was implanted onto the apical splenic nerve. At day 16, mice were placed in individual cage and connected to a PlexStim V2.3 (Plexon) stimulator and stimulation was started on the indicated days. The severity of arthritis was assessed using an established semiquantitative scoring system (for example clinical score) of 0-4, where 0=normal, 1=swelling in 1 joint, 2=swelling in ≥1 joint, 3=swelling in the entire paw, and 4=deformity and/or ankylosis. The cumulative score for all 4 paws of each mouse (maximum possible score 16) was used to represent overall disease severity and progression. For the evaluation of incidence, mice were considered to have arthritis if the clinical arthritis score was at least at 1 point for three consecutive days.

Discussion

The splenic arterial nerve (SpN) stimulation was investigated in a more chronic setting, the collagen-induced arthritis model (CIA) in mice. The mice were electrically stimulated 6 times a day (every 4 hours), or once a day starting on day 16 and followed for clinical symptoms until 45 days (FIG. 14A). While all SHAM mice and developed arthritis within 40 days, mice which were stimulated 6 times a day were complete protected throughout the stimulation period (up to day 45), with the exception of one animal (FIG. 14B). Stimulating 6 times was more effective as stimulating only 1 time a day, however, one time a day reduced disease severity compared to the sham group. In a pilot experiment starting stimulation 6 times a day after onset of disease (day 28) an increase in clinical scores (FIG. 15) was prevented.

In the prophylactic treatment group (stim start day 16), stimulation was stopped after day 45. It was evaluated if a 30 day stimulation could result in a long-term decrease in disease development or even prevent onset of disease in the animals which still did not show clinical signs of arthritis. All animals, except one, developed arthritis although the clinical scores are on average lower compared to sham implanted animals.

Electrophysiological Characterization of Human Splenic Nerves:

Materials and Methods

Human SpN Specimens

One fresh harvested tissue from a donor patient containing the splenic neurovascular bundle NVB was preserved in organ transplant-suitable solution on ice for transportation. Upon arrival the specimen was placed in ice-cold Kreb's solution under a dissecting microscope, and a minimum of one discrete SpN fascicle per sample was carefully separated from the SpA and subsequently instrumented with two bipolar circumferential cuff electrodes (0.65 mm diameter, 5.5 mm length; CorTec GmbH) placed approximately 10 mm apart, to evoke and record CAPs. Fascicle electrode coverage was estimated to be 100% in all implantations.

Recordings

Nerve activity was continuously monitored using an oscilloscope, and digitally recorded via a 1401 digital acquisition system and Spike2 software (Cambridge Electronic Design Ltd), with the sampling rate set at 20 kHz. Evoked CAPs were averaged (8 pulses) and the peak-to-peak amplitude of the averaged response quantified. The conduction velocity of the eCAP components was calculated from the measured distance between the stimulation site and the recording site and the latency of the eCAP signal (measured from the peak of the stimulation artefact to the peak of the eCAP).

Results

Figure 16B:
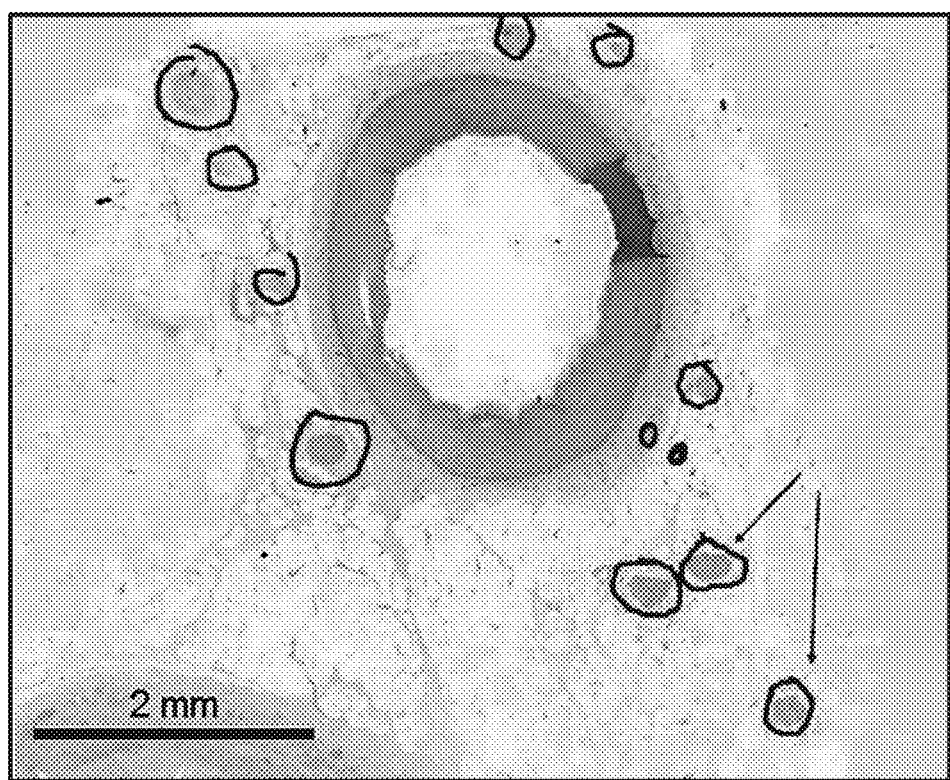
FIG. 16B shows a section of the human NVB stained with Haematoxylin and Eosin (H&E). The SpN fascicles are encircled.
Figure 16C:
FIG. 16C shows a section of the stimulated fascicles that were isolated for electrophysiological study. The section was stained with H&E and shows the nerve fascicles (encircled) and fat/connective tissue.
Figure 16D:
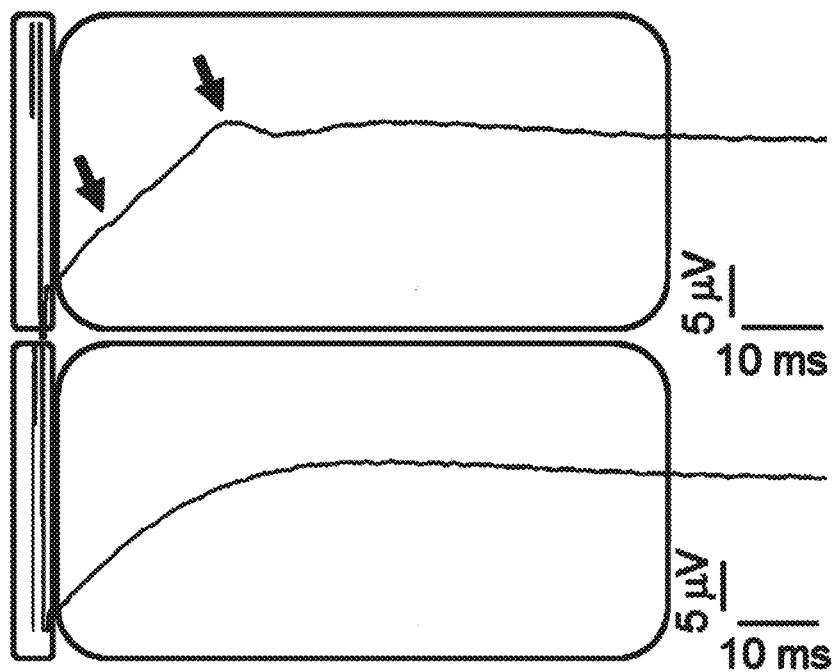
FIG. 16D shows eCAP recorded when applying monopolar, monophasic stimulation of the human SpN at 1 Hz and 400 μs PW prior (top panel) and after (bottom panel) crushing the nerve between the stimulating and recording cuff. The left box indicates the stimulation artefact while the larger box on the right indicates the area in which eCAP should be observed, with the arrows indicating the eCAP.
Figure 16E:
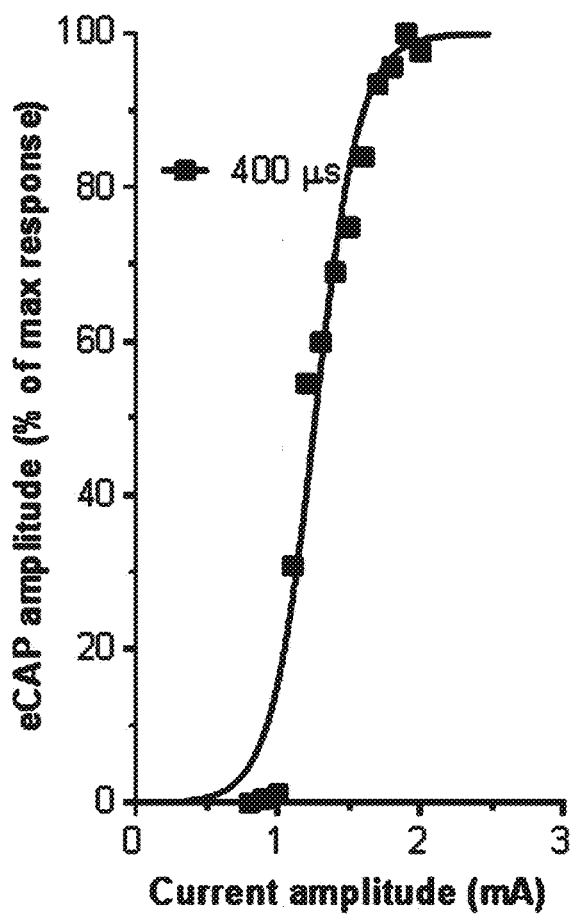
FIG. 16E shows a recruitment curve of the human SpN quantifying the eCAP amplitude (expressed as % of the maximum response) vs the stimulation amplitude. Each point represents the average amplitude of 8 consecutive monopolar, monophasic pulses delivered at 1 Hz and 400 μs PW.

Compared to the porcine samples, the human SpA presented with a more convoluted course as previously described (Michels 1942). Furthermore, the splenic NVB was embedded in extensive amounts of connective tissue and fat (FIG. 16A), making recordings from the entire circumference of the structure challenging. However, using a dissecting microscope, several nerve fascicles were visible and later confirmed as such by histological sections of the specimens (FIG. 16B). After instrumenting some of these fascicles with stimulating and recording cuff electrodes (FIG. 16A, upper and lower image), stimulation generated clear eCAPs (FIG. 16D, upper trace). To confirm the validity of the recording at the end of the experiment the fascicles were crushed between the stimulating and recording electrodes and attempts to re-record were made (FIG. 16D, lower trace). Typical recruitment curves were obtained when applying stimulations at specific pulse durations (e.g. 100, 200, 400, 800 and 1000 μs; PW) and increasing amplitude (FIG. 16E).

Figure 16G:
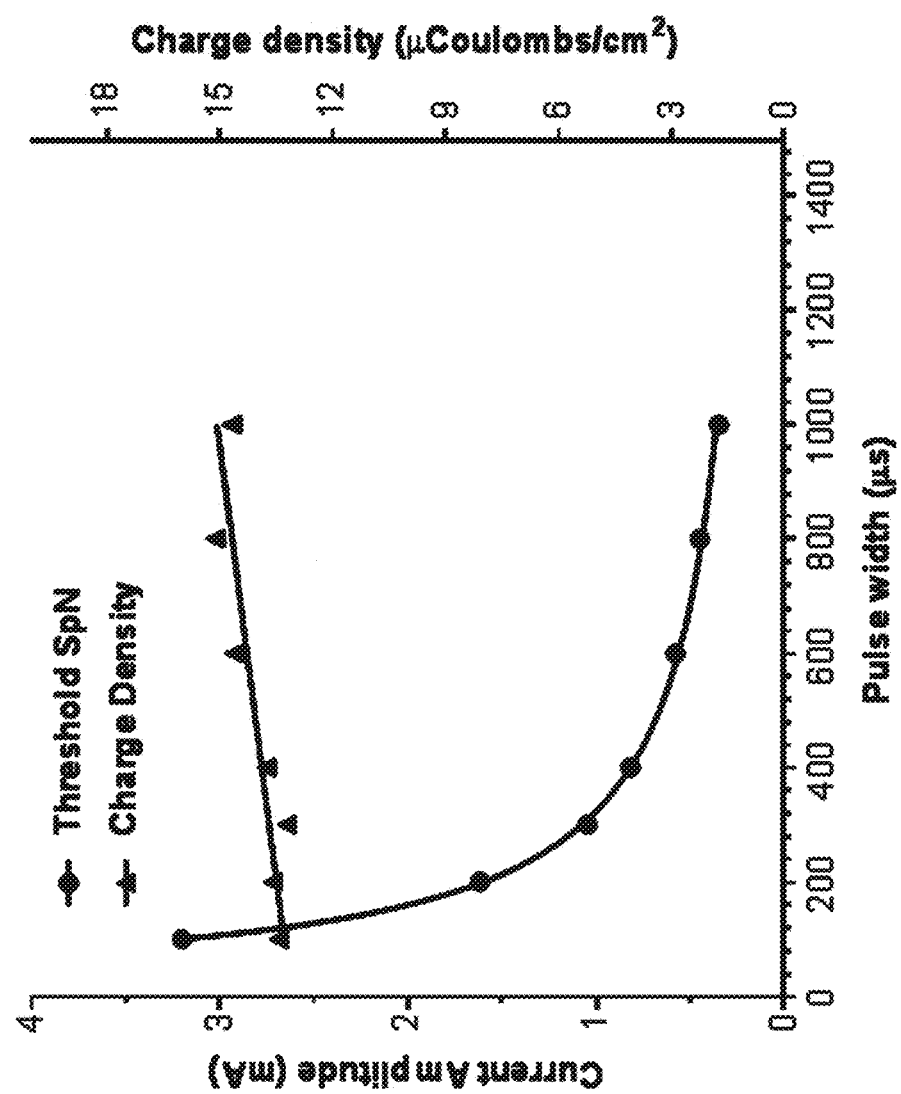
FIG. 16G shows the strength-duration relationship (black circles) of the human SpN obtained by stimulating the dissected fascicles. The data represent the minimum current needed to trigger a detectable eCAP at the different PW tested. The graphs also show the corresponding charge density (black triangles) of the different stimulations (referred to the right Y axis). Least squares regression curves were plotted against the strength-duration and charge density data.
Figure 16F:
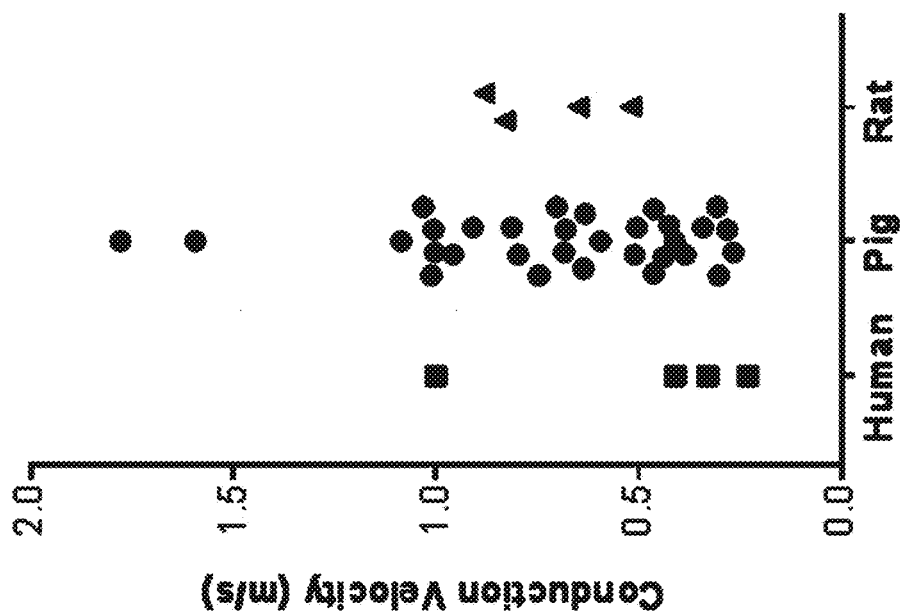
FIG. 16F shows conduction velocities of all the eCAP components recorded from the human, porcine (pig) and rat SpN.

Calculated conduction velocities demonstrated typical values for unmyelinated fibres, where the range and average conduction velocity was 0.49 m/s, compared to porcine (0.7 m/s) and rat (0.72 m/s) SpN (FIG. 16F). In addition, the eCAP recordings of the human SpN showed a typical strength-duration relationship between current amplitude for nerve recruitment and pulse duration (FIG. 16G). Linear regression of the calculated charge density value for eCAP threshold recording showed slopes significantly different from zero (P=0.0084), with the lowest PW (100 μs) requiring 13.44 μC/cm$^2$, and the longest PW (2000 μs) requiring 14.7 μC/cm$^2$. Importantly, the slope in the charge density for the human SpN fascicles was found to be similar to the slope of the charge density for the porcine fascicles (FIG. 16H). In addition, the charge density requirement for nerve activation of the dissected human fascicles was about 1.5-2 times higher than the charge density required for activation of the porcine SpN fascicles at any PW (FIG. 16H).

Discussion

The human SpN has anatomical, morphological and electrophysiological characteristics similar to other mammals (porcine and rodent). The human SpN are composed of unmyelinated axons as confirmed by conduction velocities. It is therefore appropriate to assume that the stimulation parameters (frequency and waveform) optimized in the pig will be also suitable for the human splenic nerve. However, requirements for charge need to be calculated from the entire NVB.

Histomorphometric Characterization of Human Splenic Anatomy

The objective of this study was to develop an understanding of the human splenic anatomy and estimate the approximate values of splenic neurovascular bundle (NVB) using histology (see Table 2). The study was performed on the splenic tissue received from transplant patients. Histomorphometric estimations for lumen diameter, arterial wall, fascicle diameter (mean Feret diameter) and the approximate distance of each fascicle from adventitia (outer splenic arterial wall) were calculated.

Figure 17A:
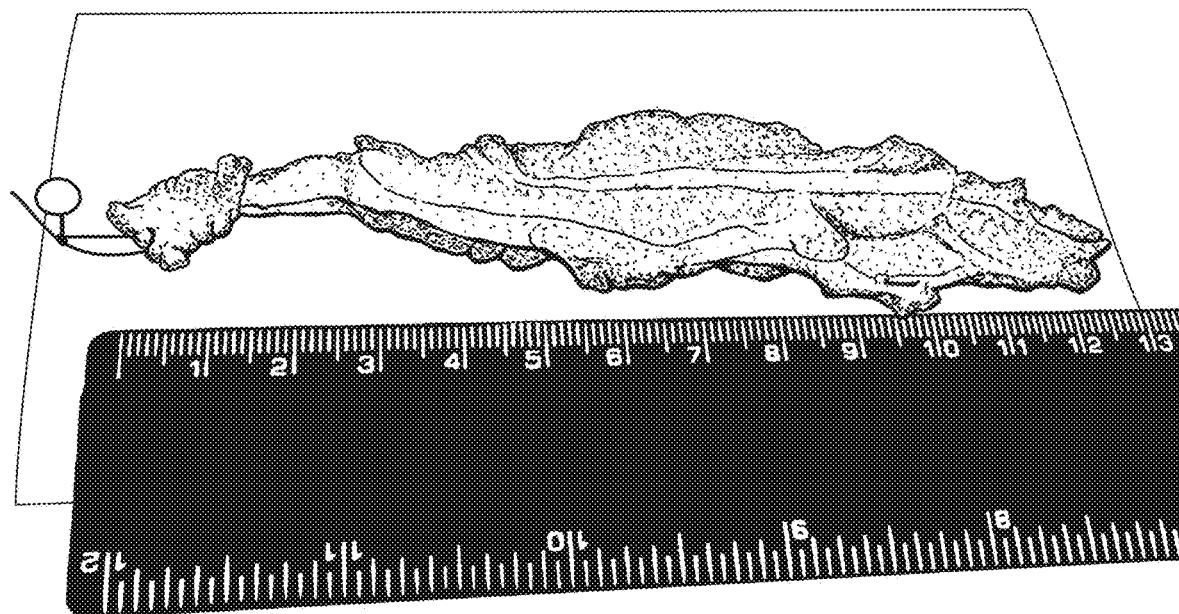
FIG. 17A shows an example of a human splenic sample with suture indicating the proximal end close to celiac.
Figure 17B:
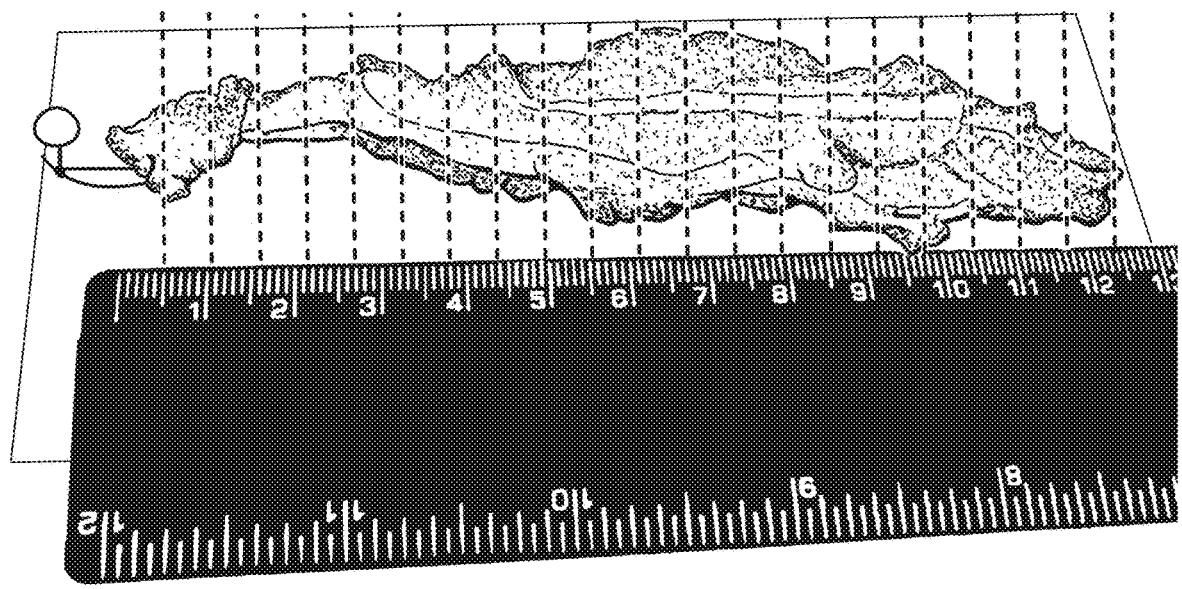
FIG. 17B shows conceptual representation of slicing of tissue in blocks for histology.
Figure 17C:
FIG. 17C shows Haematoxylin and Eosin (H&E) stained slide from one of the blocks.
Figure 17D:
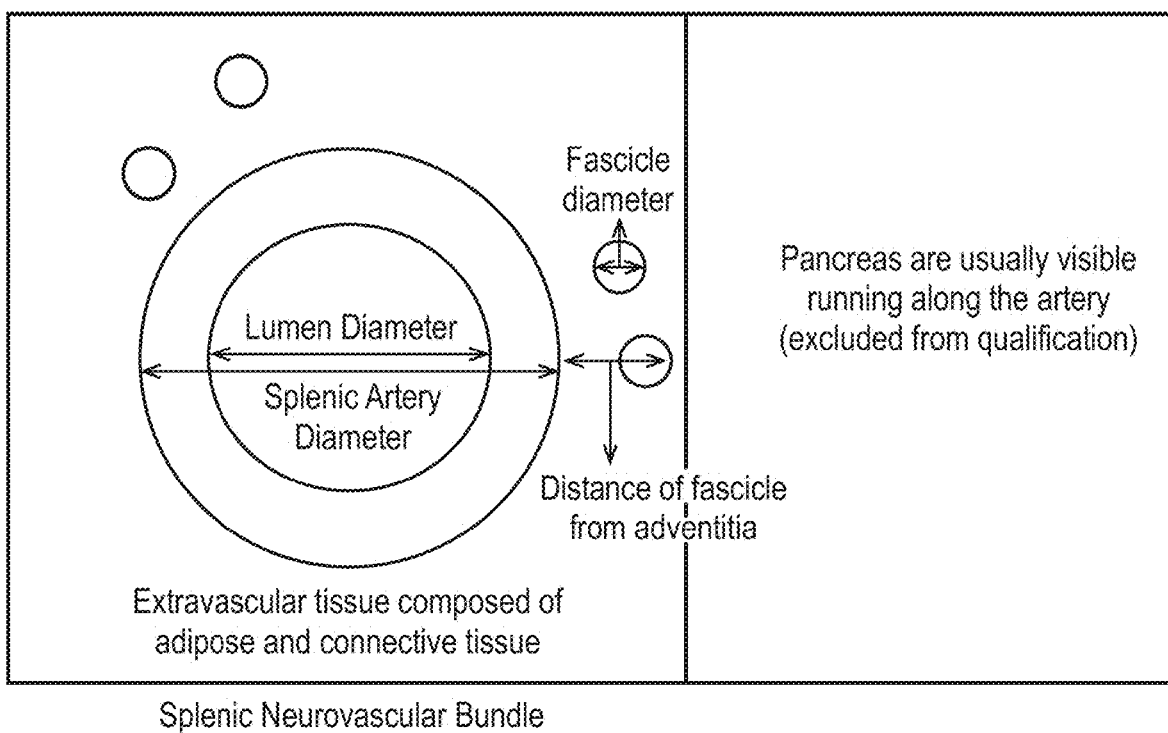
FIG. 17D shows methodology for histomorphometric estimations.

Materials and Methods:

Five human splenic NVBs were provided from transplant patients at Addenbrooke's hospital, Cambridge, UK. The tissue was immersed in 10% neutral buffered formalin (NBF) as soon as possible post-excision. Photographs of the tissue were taken, with a ruler present for gross measurements (see FIG. 17A). The samples were divided in sequential blocks of 0.5 cm-1.5 cm for histology (see FIG. 17B). The tissue around the artery was retained for inclusion in the block. The sections were embedded and sectioned such that the same face of each block (i.e. proximal or distal to spleen) was sampled each time. The sections were usually 4-5 um thick and were stained with hematoxylin and eosin stain (H&E) (see FIG. 17C). Finally, a quality check of the tissue was performed by a pathologist and the glass slides were scanned at ×20. It should be noted that, as per literature, 10% of tissue shrinkage is accounted for. However, the artery diameter is representative of zero pressure. High amounts of adipose tissue was noted in all the samples received from transplant patients and the fascicles were found to be buried in a thick layer of adipose tissue.

TABLE 2

Estimated range for human splenic neurovascular bundle (~7 mm to 10 mm)

| Sample Number | Lumen Diameter | Lumen Wall + Arterial wall | Accounting for shrinkage of the tissue (+10%) | Range of extravascular tissue (based on middle splenic arterial loop) | Total NVB (*Does not account for pulsatile nature of the artery) |
|---|---|---|---|---|---|
| Sample 308B X91165 | 3.01 mm | 5.02 mm | 5.5 mm | 3.5 mm | 9 mm |
| Sample 359B X91252 | 3.92 mm | 5.2 mm | 5.72 mm | 2.4 mm | 8.12 mm |

TABLE 2-continued

Estimated range for human splenic neurovascular bundle (~7 mm to 10 mm)

| Sample Number | Lumen Diameter | Lumen Wall + Arterial wall | Accounting for shrinkage of the tissue (+10%) | Range of extravascular tissue (based on middle splenic arterial loop) | Total NVB (*Does not account for pulsatile nature of the artery) |
|---|---|---|---|---|---|
| Sample 377C X91287 | 3.3 mm | 4.93 mm | 5.42 mm | 3.8 mm | 9.2 mm |
| Sample 380C X91291 | 2.76 mm | 4.72 mm | 5.192 mm | 4.9 mm | 10 mm |
| Sample 382B X91299 | 2.57 mm | 4 mm | 4.4 mm | 2.5 mm | 6.9 mm |

For quantification purposes, the splenic tissue was divided into three parts: proximal, middle and distal. Each of these parts consisted of several sections. The proximal end is close to the celiac indicated with a suture in FIG. 17A and distal is close to the spleen. Both of these are unlikely to be the intervention site for neural interface placement. The middle part with loops would be the likely intervention site.

To summarise, as shown in FIG. 18, fascicle diameters are in the range of 20-400 um. For the fascicle spread approximately half of the nerve fibres were found in 0-1 mm region, 30% in 1-2 mm, 15% in 2-3 mm and the remaining in about 3-4 mm region.

Translational Charge Requirements from Porcine to Human Splenic Neurovascular Bundle Materials and Methods:

3D Finite Element Model computer simulations were created using histology data from porcine and human splenic histology. This essentially comprised of splenic artery (lumen+arterial wall) and extravascular tissue. The 'extravascular tissue' is composed of 'adipose tissue' and 'connective tissue', with nerves embedded in the tissue. For porcines, a model with a split in the Cortec cuff (representing the in-vivo cuff) was used. For human models, cuffs with three arms structure were used. The diameter of the used cuff was 9 mm.

Considering the differences between porcine and human histology: the fascicles in porcine are evenly distributed around the artery and are in close proximity, whereas the fascicles in humans appear more dispersed; and b) the histology in porcine indicates negligible adipose tissue extravascularly, converse to substantial amounts in humans.

To translate the estimation of stimulation parameters from porcine to human, modeling was performed in the following two phases:

Phase (a): Development of 3D Finite Element Models (FEM) in Sim4Life simulation tool.

Sim4Life was used to develop representative nerve and artery models (based on histology and image quantification), cuff and electrodes (specifications defined by CAD) and 3D voltage fields.

Phase (b): Analysis of FEM solutions in the same tool. Sim4Life was used to interpolate voltage along axons using Sundt nerve model [24], and axon simulations estimated the strength-duration and population recruitment curves.

Results

Figure 19B:
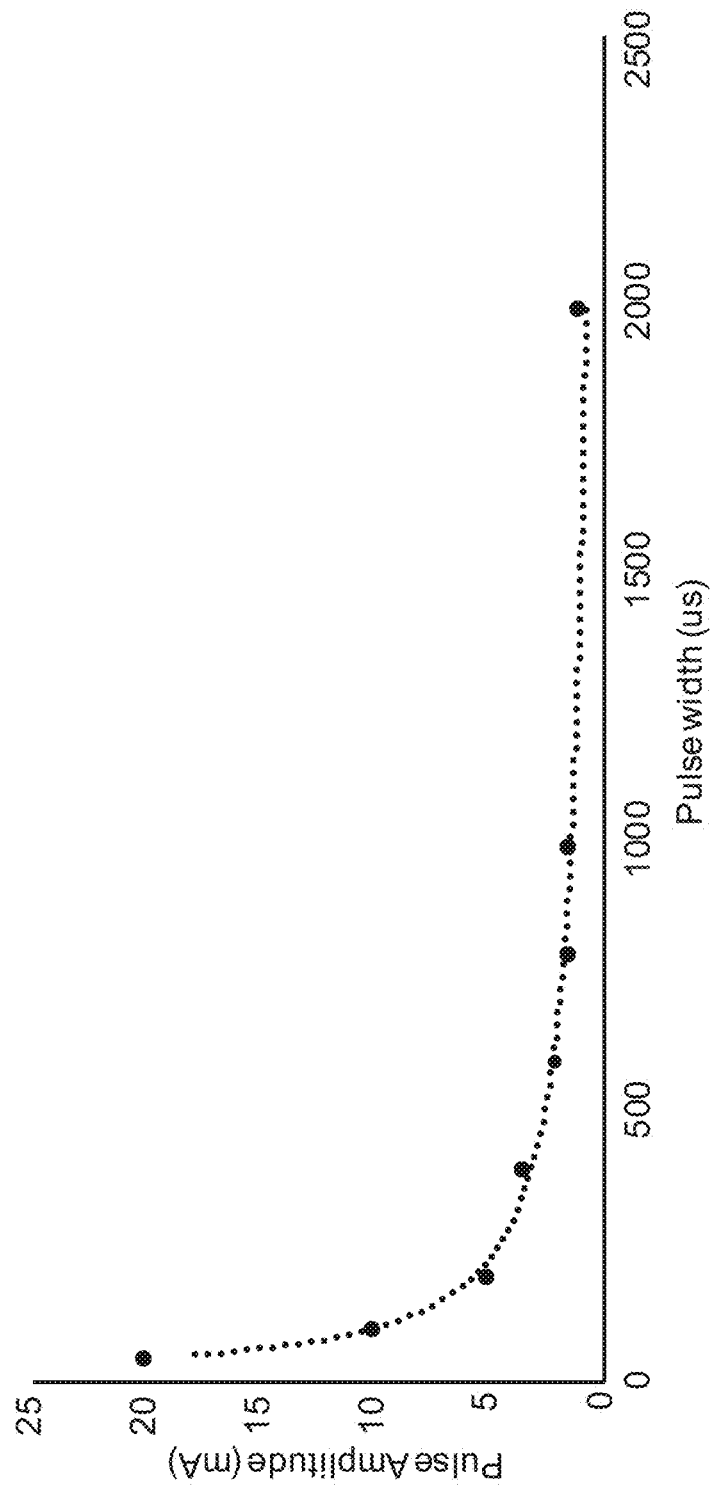
FIG. 19B shows a strength-duration curve for in-vivo data from porcine splenic neurovascular bundle stimulation.
Figure 20A:
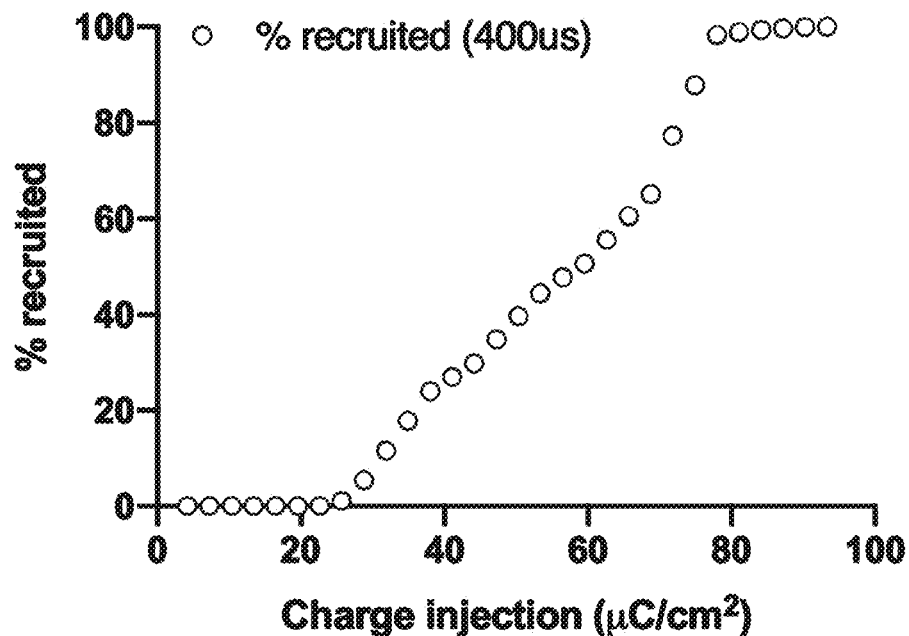
FIG. 20A shows a recruitment curve from in-silico modelling in porcines with x-axis representing charge injection estimates at 400 μs pulses.
Figure 20B:
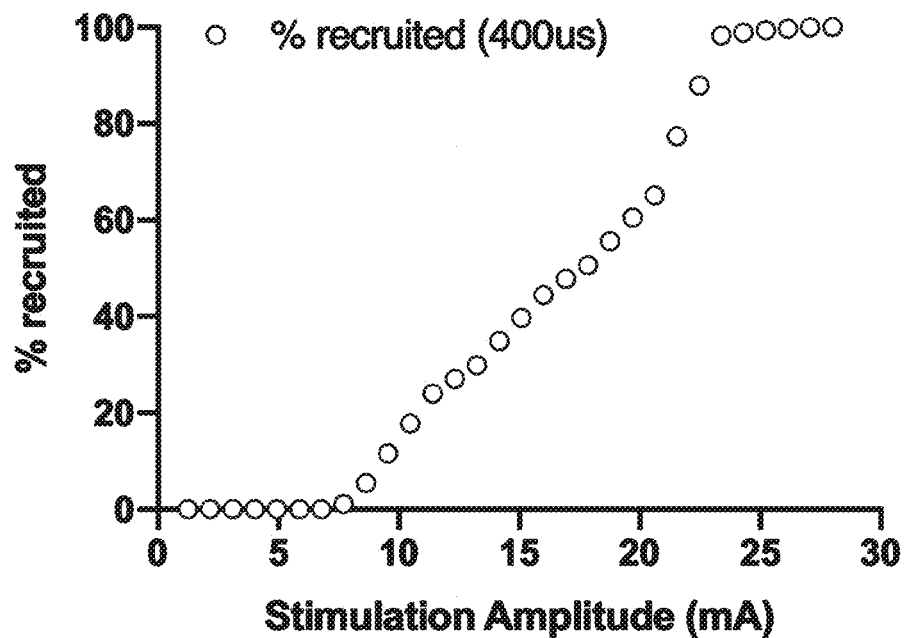
FIG. 20B shows the same but with x-axis reflecting stimulation amplitude.
Figure 20C:
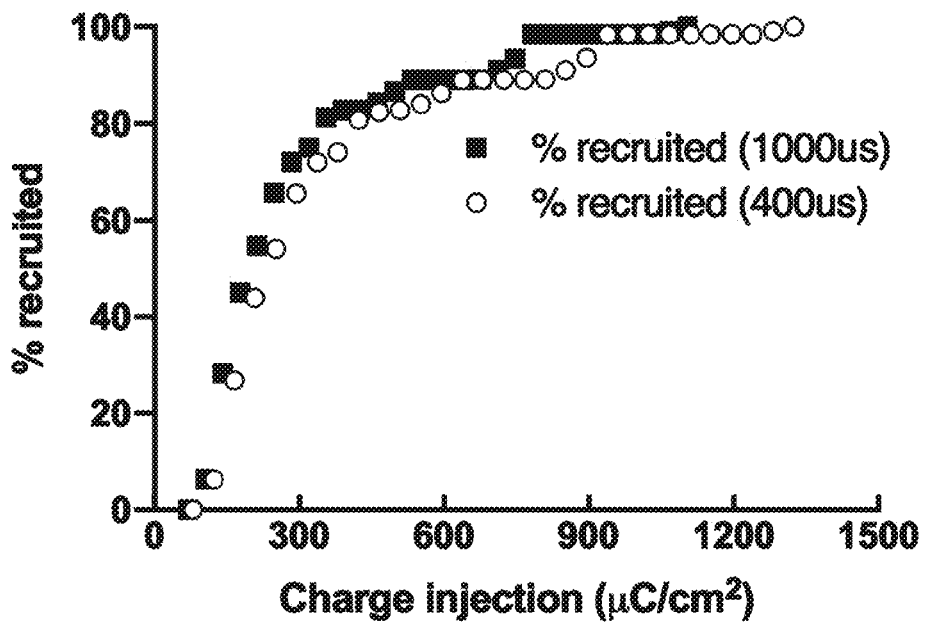
FIG. 20C shows a recruitment curve from in-silico modelling in humans with x-axis representing charge injection estimates at 400 μs (blue) and 1 ms pulses (red).
Figure 20D:
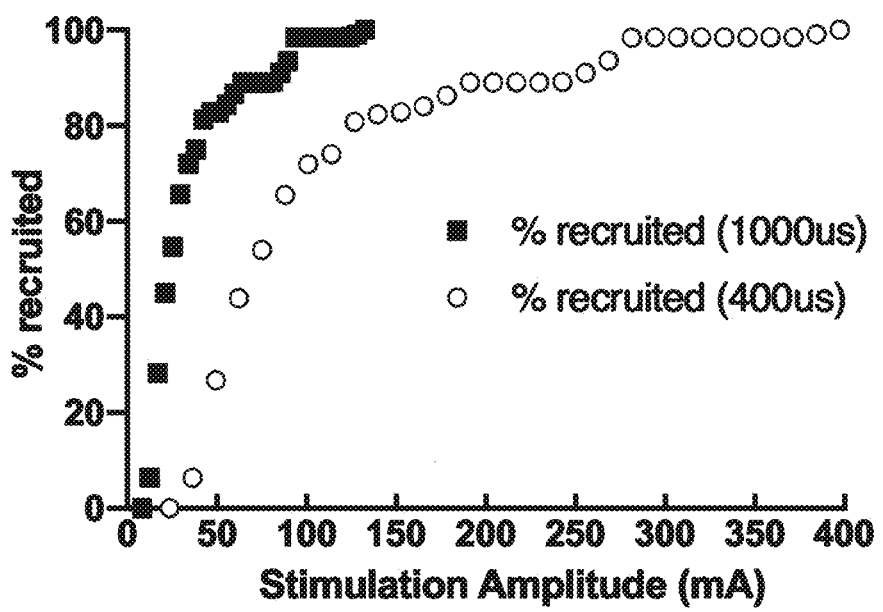
FIG. 20D shows the same but with x-axis reflecting stimulation amplitude (mA).

FIG. 19A represents the in-vivo acute data from porcine splenic neurovascular bundle from five animals. The range from five animals for charge requirements is estimated to be approximately 20-160 uC/cm$^2$ at ≤50 mA, 400 us and 10 Hz. For the third animal represented in grey the charge requirements are approximately 100 uC/cm$^2$ at 30 mA, 400 us and 10 Hz, which correlates well with the simulated data in-silico (see FIG. 20A). Using the correlation of in-silico vs in-vivo as a validation for the computational model in porcine, the charge requirements were translated to human splenic neurovascular bundle using histology sections for two pulse widths. The data is presented in FIGS. 20C-D and Table 3.

TABLE 3

Charge estimates for human models for two pulse widths i.e. 400 us and 1 ms pulses

| Pulse Width % recruited | Charge estimates 400 us (μC/phase/cm$^2$) (Approx.) | Charge estimates 1000 us (μC/phase/cm$^2$) (Approx.) |
|---|---|---|
| Threshold | 79 | 70 |
| 10 | 130 | 110 |
| 30 | 170 | 150 |
| 50 | 225 | 200 |
| 80 | 422.8 | 335 |
| 80-100 | 450-1300 | 350-1100 |

It is estimated that the charge requirements in human acute models for a recruitment of 100% can potentially vary from approximately 80-1300 μC/cm$^2$ (using 400 uS pulse widths, 12 mm$^2$ surface area) and 70-1100 μC/cm$^2$ (using 1 ms pulse widths). Approximately 70% of the recruitment is indicated under 350 μC/cm$^2$. The additional 30% recruitment requires exponential increase in charge requirements beyond what is likely accommodated for by an implantable device. For example, it can be seen that a recruitment of 100% can potentially vary between 70-1300 μC/cm$^2$, between 70-450 μC/cm$^2$ for 80% recruitment, between 70-250 μC/cm2 for 50% recruitment, and between 70-170 μC/cm$^2$ for 30% recruitment.

Discussion

The nerves fibres in the humans are more dispersed in comparison to porcines. The range of the fascicle spread around splenic artery as indicated by histology profiling can be in the range of approximately 1-3 mm. The histomorphomteric data was further used to optimise the stimulation parameters and translate the charge requirements from porcines to humans using computational modelling tools. Using Sundt c-fibre model the charge requirements for humans is indicated to be in range of approximately 70-1000 µC/cm² for hundred percent recruitment.

REFERENCES

[1] Medzhitov, Nature 454, 428-435 (24 Jul. 2008).
[2] J. M. Huston et al., J Exp Med 203, 1623.
[3] D. M. Nance, V. M. Sanders, Brain Behav Immun 21, 736.
[4] H. H. Dale, H. W. Dudley, J Physiol 68, 97.
[5] C. Cailotto et al., Neurogastroenterol Motil 24, 191.
[6] M. Rosas-Ballina, K. J. Tracey, Neuron 64, 28.
[7] G. Vida, G. Pena, E. A. Deitch, L. Ulloa J Immunol 186, 4340.
[8] B. O. Bratton et al., Exp Physiol 97, 800.
[9] D. Martelli, S. T. Yao, M. J. McKinley, R. M. McAllen, J Physiol 592(7), 1677.
[10] D. Martelli, S. T. Yao, J. Mancera, M. J. McKinley, R. M. McAllen, Am J Physiol Regul Integr Comp Physiol 307, R1085.
[11] D. Martelli, M. J. McKinley, R. M. McAllen, Auton Neurosci. 182, 65.
[12] Koopman F A et al., Proc Natl Acad Sci USA, 19; 60(29):8284.
[13] Greenway et al., J. Physiol. (1968), 194, 421-433.
[14] US 2006/0287678. [0418]
[15] US 2005/0075702.
[16] US 2005/0075701.
[17] Schafer, E. A. and Moore, B., J Physiol, 1896.
[18] G. L. Brown, J. S. Gillespie J S, J Physiol, 138:81-102, 1957.
[19] A. G. Garcia, et al., J Physiol, 261:301-317, 1976.
[20] Gee, M. D., Lynn, B., Cotsell, B., Neuroscience, 1996, 73, 3, 667-675.
[21] Weidner, C., et al., J of Physiol 2000, 527, 185-191.
[22] Lin, C. S., Mogyoros, I., Burke, D., Muscle Nerve, 2000, 23, 5, 763-770. [0426]
[23] Stohr, M., J of Neurol Sci 1981, 49, 1, 47-54. [0427]
[24] Sundt D, et al., Journal of neurophysiology. 114:3140-53, 2015. Electrical Stimulation of the Splenic Arterial Nerve in Pig (Study 1)

The invention claimed is:

1. A system for stimulating the neural activity of a splenic arterial nerve, the system comprising:
at least one electrode in signaling contact with the nerve at a site where the splenic artery is not in direct contact with the pancreas; and
at least one controller electrically coupled to the at least one electrode, the at least one controller configured to control the operation of the least one electrode to apply an electrical signal to the nerve, wherein a charge density per phase applied to the nerve by the electrical signal is between 5 µC to 1100 µC per cm2 per phase, wherein the electrical signal produces an improvement in a physiological parameter in a subject, and wherein the improvement in the physiological parameter is one or more of a group consisting of: a reduction in a pro-inflammatory cytokine, an increase in an anti-inflammatory cytokine, an increase in a catecholamine, a change in an immune cell population, a change in an immune cell surface co-stimulatory molecule, a reduction in a factor involved in the inflammation cascade, a change in a level of an immune response mediator, and a decrease in splenic blood flow.

2. The system of claim 1, wherein the site is a position of the splenic artery separated from the surface of the pancreas by a distance in a range of from 0.5 cm to 4 cm.

3. The system of claim 1, wherein the site is at a splenic arterial loop.

4. The system of claim 1, wherein the electrical signal comprises a pulse train, the pulse train comprising a plurality of pulses.

5. The system of claim 4, wherein the pulses are charge-balanced and biphasic.

6. The system of claim 1, further comprising at least one detector configured to detect one or more of a group consisting of: systemic arterial blood pressure, blood flow rate in the spleen, blood flow rate in the splenic artery, blood flow rate in the splenic vein, spleen volume, splenic tissue perfusion, neural activity in the nerve, impedance of the at least one electrode, and stimulator voltage compliance.

7. The system of claim 6, wherein the at least one controller is further configured to apply an electrical signal to the nerve for determining correct placement of the neural interface in signaling contact with the nerve prior to applying the electrical signal to the nerve, wherein the electrical signal has a frequency of ≤300 Hz and is applied continuously for a duration of ≥3 hours.

8. The system of claim 7, wherein the at least one detector is further configured to detect spleen volume, and wherein the at least one controller is further configured to determine if the detected spleen volume is lower than baseline spleen volume and, if so, to indicate to an operator that the neural interface has been placed in signaling contact with the nerve correctly.

9. The system of claim 8, wherein the at least one detector is further configured to measure spleen volume using ultrasound.

10. The system of claim 6, wherein the at least one detector is further configured to detect one or more of a group consisting of: systemic arterial blood pressure, blood flow rate in the spleen, blood flow rate in the splenic artery, and blood flow rate in the splenic vein, and wherein the at least one controller is further configured to determine if a detected blood pressure or blood flow rate is different than a baseline blood pressure or blood flow rate and, if so, to indicate to an operator that the neural interface has been placed in signaling contact with the nerve correctly.

11. The system of claim 10, wherein the at least one detector is further configured to detect impedance of the at least one electrode, and wherein the at least one controller is further configured to determine if the detected impedance is different than baseline impedance and, if so, to indicate to an operator that the neural interface has been placed in signaling contact with the nerve correctly.

12. A method of reversibly stimulating neural activity in a nerve supplying the spleen, the method comprising:
providing the system of claim 1;
positioning at least one electrode in signaling contact with the nerve adjacent to a splenic arterial loop; and
controlling the operation of the least one electrode with at least one controller to apply an electrical signal to the nerve to reversibly stimulate neural activity.

13. The method of claim 12, wherein the method is for treating a disorder associated with inflammation in a subject.

14. A method of determining whether a neural interface is correctly placed in signaling contact with a splenic arterial nerve at a site where the splenic artery is not in direct contact with the pancreas, the method comprising:
providing the system of claim 1;
positioning the neural interface around a nerve at a site where the splenic artery is not in direct contact with the pancreas;

controlling the operation of the least one electrode with at least one controller to apply an electrical signal to the nerve;

determining one or more of a: a change in blood flow rate or pressure in the spleen, splenic artery, or splenic vein, a decrease in spleen volume, an increase in neural activity in the nerve, a change of heart rate, a change of systemic arterial blood pressure, a decrease in impedance of the at least one electrode, and a decrease in a stimulator voltage compliance; and indicating to an operator that the neural interface had been placed correctly in signaling contact with the nerve.

15. The method of claim 14, wherein the site is at a position of the splenic artery separated from the surface of the pancreas by a distance in a range of 0.5 cm to 4 cm.

16. The method of claim 15, wherein the site is at a splenic arterial loop.

* * * * *